(12) United States Patent
Stamler et al.

(10) Patent No.: US 7,033,999 B2
(45) Date of Patent: Apr. 25, 2006

(54) NITROSATED AND NITROSYLATED HEME PROTEINS

(75) Inventors: Jonathan Stamler, Chapel Hill, NC (US); Joseph Loscalzo, Dover, MA (US)

(73) Assignee: Brigham and Women's Hospital, Boston, MA (US)

( * ) Notice: Subject to any disclaimer, the term of this patent is extended or adjusted under 35 U.S.C. 154(b) by 444 days.

(21) Appl. No.: 10/413,220

(22) Filed: Apr. 15, 2003
(Under 37 CFR 1.47)

(65) Prior Publication Data

US 2003/0211977 A1 Nov. 13, 2003

Related U.S. Application Data

(60) Division of application No. 09/835,038, filed on Apr. 16, 2001, now Pat. No. 6,583,113, which is a division of application No. 09/092,622, filed on Jun. 5, 1998, now Pat. No. 6,291,424, which is a continuation-in-part of application No. 08/409,720, filed on Mar. 24, 1995, now abandoned, which is a continuation-in-part of application No. 08/198,854, filed on Feb. 17, 1994, now abandoned, which is a division of application No. 07/943,835, filed on Sep. 14, 1992, now abandoned, which is a continuation-in-part of application No. 07/791,668, filed on Nov. 14, 1991, now abandoned.

(51) Int. Cl.
*A61K 38/16* (2006.01)
*A61K 38/48* (2006.01)
*A61K 31/445* (2006.01)
*A61K 31/16* (2006.01)
*C07K 14/805* (2006.01)

(52) U.S. Cl. .................... 514/6; 514/2; 514/7; 514/19; 514/21; 514/183; 514/185; 530/385

(58) Field of Classification Search ............... 514/2, 514/6, 19, 21, 183, 185; 530/385
See application file for complete search history.

(56) References Cited

U.S. PATENT DOCUMENTS

| | | | |
|---|---|---|---|
| 4,703,039 A | 10/1987 | Hawiger et al. | |
| 4,900,719 A | 2/1990 | Means et al. | |
| 5,002,964 A | 3/1991 | Loscalzo | |
| 5,025,001 A | 6/1991 | Loscalzo et al. | |
| 5,116,861 A | 5/1992 | Goto et al. | |
| 5,187,183 A | 2/1993 | Loscalzo et al. | |
| 5,356,890 A | 10/1994 | Loscalzo et al. | |
| 5,380,758 A | 1/1995 | Stamler | |
| 5,525,357 A | 6/1996 | Keefer et al. | |
| 5,545,614 A | 8/1996 | Stamler | |
| 5,574,068 A | 11/1996 | Stamler | |
| 5,583,101 A | 12/1996 | Stamler et al. | |
| 5,593,876 A * | 1/1997 | Stamler et al. | 435/188 |
| 5,840,851 A * | 11/1998 | Plomer et al. | 530/385 |
| 5,863,890 A * | 1/1999 | Stamler et al. | 514/2 |
| 6,197,745 B1 | 3/2001 | Stamler | |
| 6,291,424 B1 * | 9/2001 | Stamler et al. | 514/6 |

OTHER PUBLICATIONS

European Search Report for European Application No. 00108906.9-2107—(Sep. 26, 2000).
McNamara et al, Canadian Journal of Physiology and Pharmacology, 58 (12):1446-1456 (1980) (Abstract).
Gruetter et al, Journal of Pharmacology and Experimental Therapeutics, 214(1):9-15 (1980) (Abstract).
Jansen et al, Journal of Pharmacology and Experimental Therapeutics, 261(1):154-160 (1992) (Abstract).
Stamler et al, Biology of Nitric Oxide, 1:20-23 (1992).
Buga et al, European Journal of Pharmacology, 161:61-72 (1989).
Chong et al, Drug Metabolism and Disposition, 18(1):61-67 (1990).
Edwards et al, Biochemical Pharmacology, 30 (18):2531-2538 (1981).
Forstermann et al, Molecular Pharmacology, 38:7-13 (1990).
Ignarro, Circulation Research, 65(1):1-21 (Jul. 1989).

(Continued)

*Primary Examiner*—Herbert J. Lilling
(74) *Attorney, Agent, or Firm*—Wilmer Cutler Pickering Hale and Dorr LLP

(57) ABSTRACT

Nitrosylation of proteins and amino acid groups enables selective regulation of protein function, and also endows the proteins and amino acids with additional smooth muscle relaxant and platelet inhibitory capabilities. Thus, the invention relates to novel compounds achieved by nitrosylation of protein thiols. Such compounds include: S-nitroso-heme proteins, S-nitroso-t-PA, S-nitroso-cathepsin; S-nitroso-lipoproteins; and S-nitroso-immunoglobulins. The invention also relates to therapeutic use if S-nitroso-protein compounds for regulating protein function, cellular metabolism and effecting vasodilation, platelet inhibition, relaxation of non-vascular smooth muscle, and increasing blood oxygen transport by hemoglobin and myoglobin. The compounds are also used to deliver nitric oxide in its most bioactive form in order to achieve the effects described above, or for in vitro nitrosylation of molecules present in the body. The invention also relates to the nitrosylation of oxygen, carbon and nitrogen moieties present on proteins and amino acids, and the use thereof to achieve the above physiological effects.

5 Claims, 41 Drawing Sheets

OTHER PUBLICATIONS

Ignarro et al, The Journal of Pharmacology and Experimental Therapeutics, 218(3):739-749 (1981).
Jia et al, Nature, 380:221-226 (Mar. 1996).
Kosaka et al, Free Radical Biology & Medicine, 7:653-658 (1989).
Loscalzo et al, The Journal of Pharmacology and Experimental Therapeutics, 249(3):726-729 (1989).
Loscalzo et al, The New England Journal of Medicine, 319(14):925-931 (Oct. 1988).
Loscalzo, J. Clin. Invest., 76:703-708 (Aug. 1985).
Mahley et al, JAMA, 265(1):78-83 (Jan. 1991).
Mellion et al, Molecular Pharmacology, 23:653-664 (1983).
Myers et al, Nature, 345:161-163 (May 1990).
Stamler et al, Proc. Natl. Acad. Sci. USA, 89:8087-8091 (Sep. 1992).
Stamler et al, Proc. Natl. Acad. Sci. USA, 89:7674-7677 (Aug. 1992).
Stamler et al, Proc. Natl. Acad. Sci. USA, 89:444-448 (Jan. 1992).
Stamler et al, Circulation Research, 65 (3):789-795 (Sep. 1989).
Umemoto et al, Biochemical and Biophysical Research Communications, 151 (3):1326-1331 (Mar. 1988).

* cited by examiner

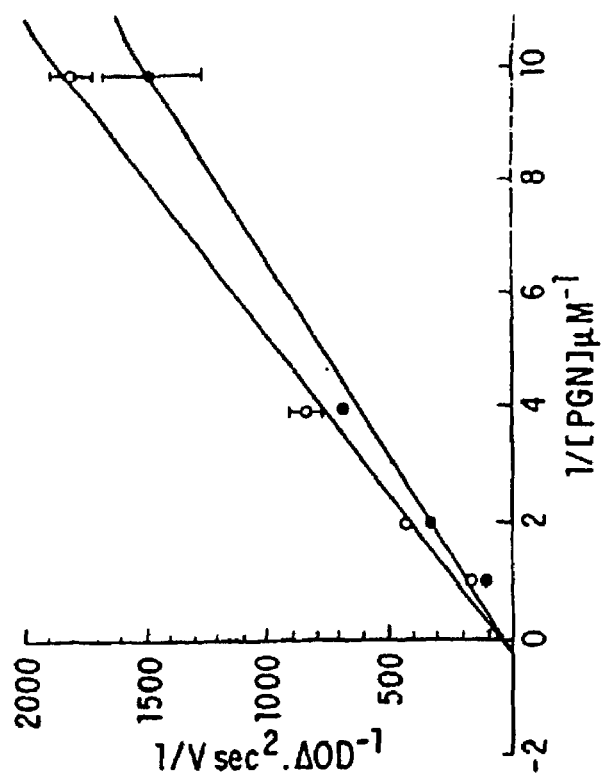
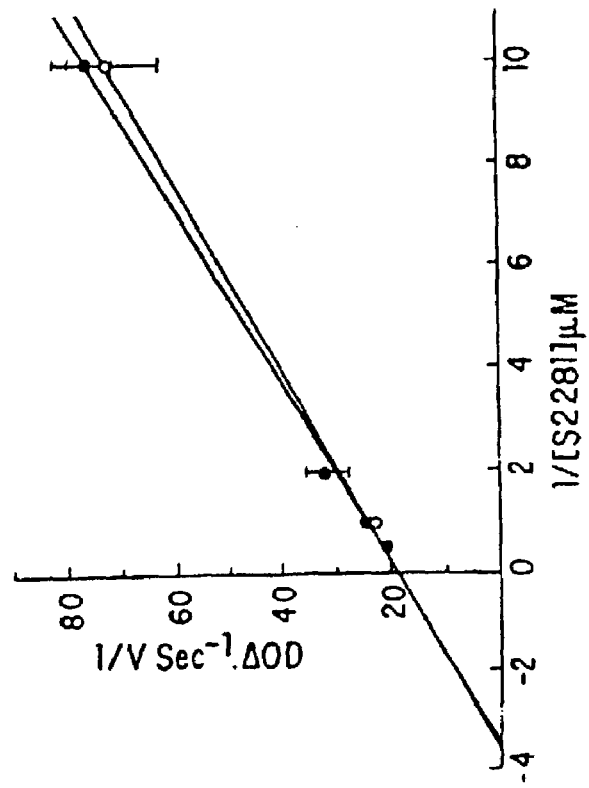
FIG. 5B
FIG. 5A

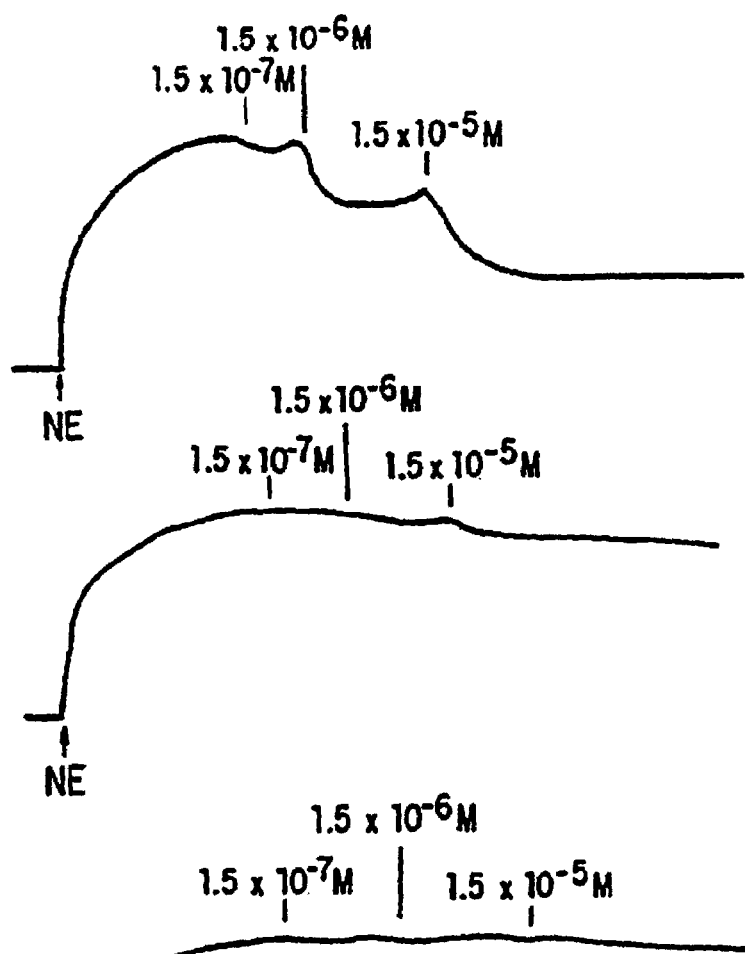
FIG. 11B-(1)
FIG. 11B-(2)
FIG. 11B-(3)

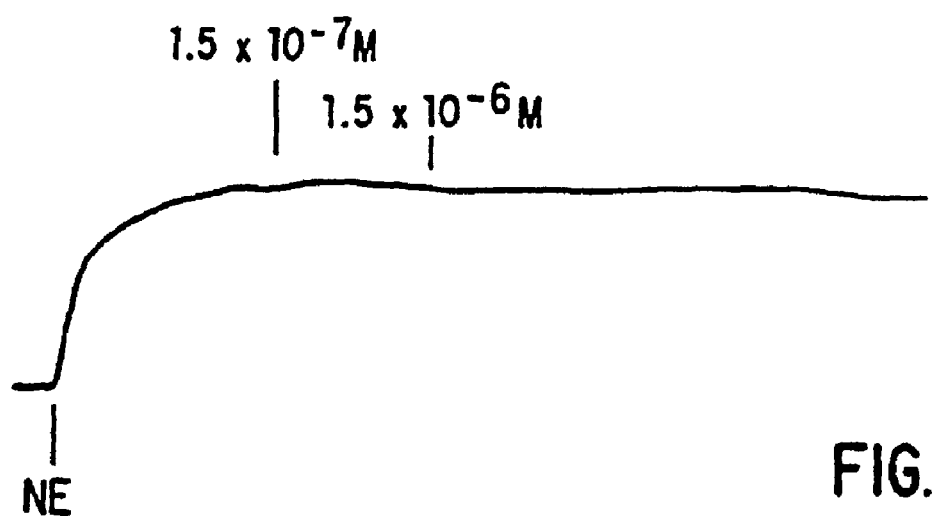
FIG. 11B-(4)

*1 DOSE-RESPONSE TO S-NITROSO-CATHEPSIN

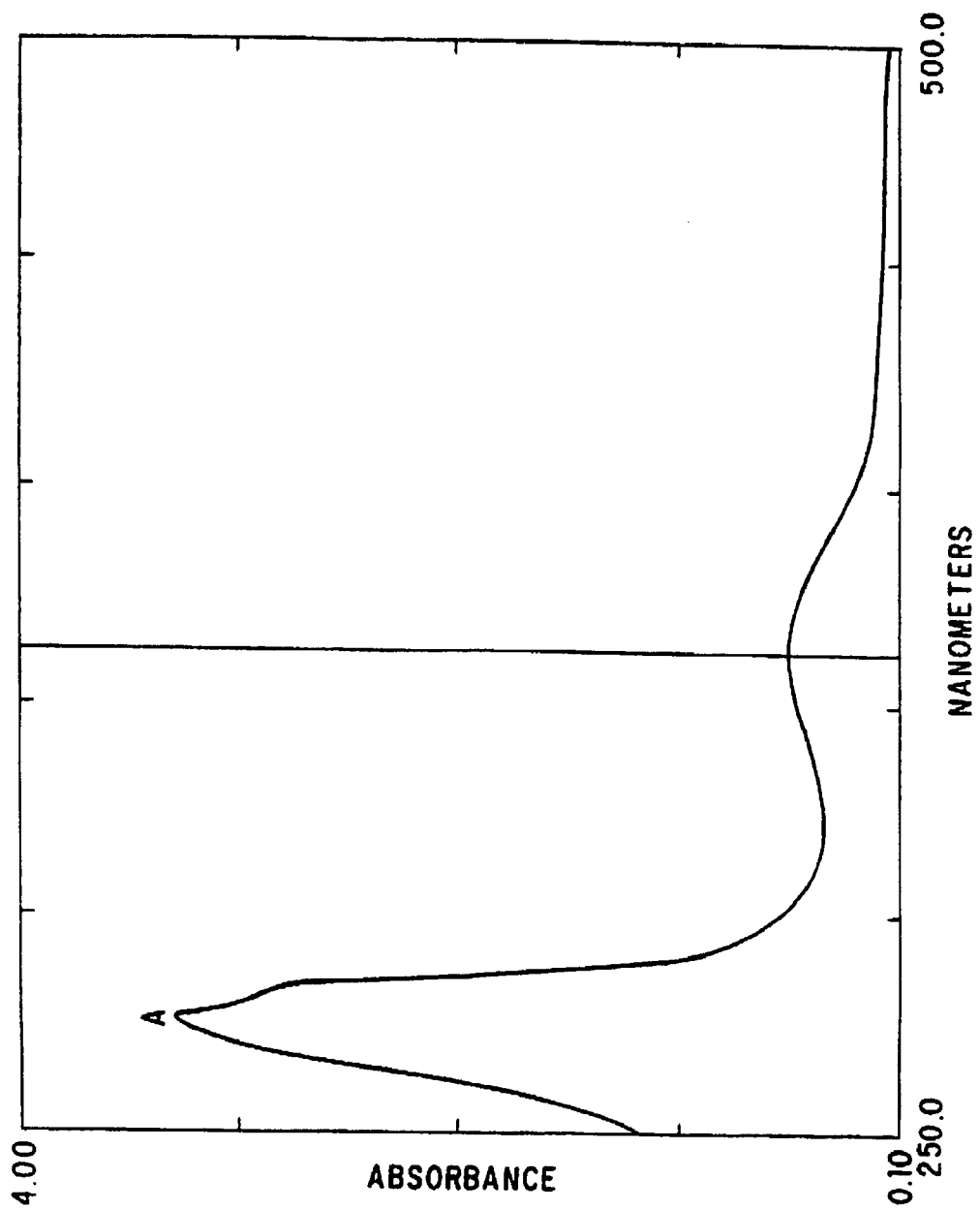

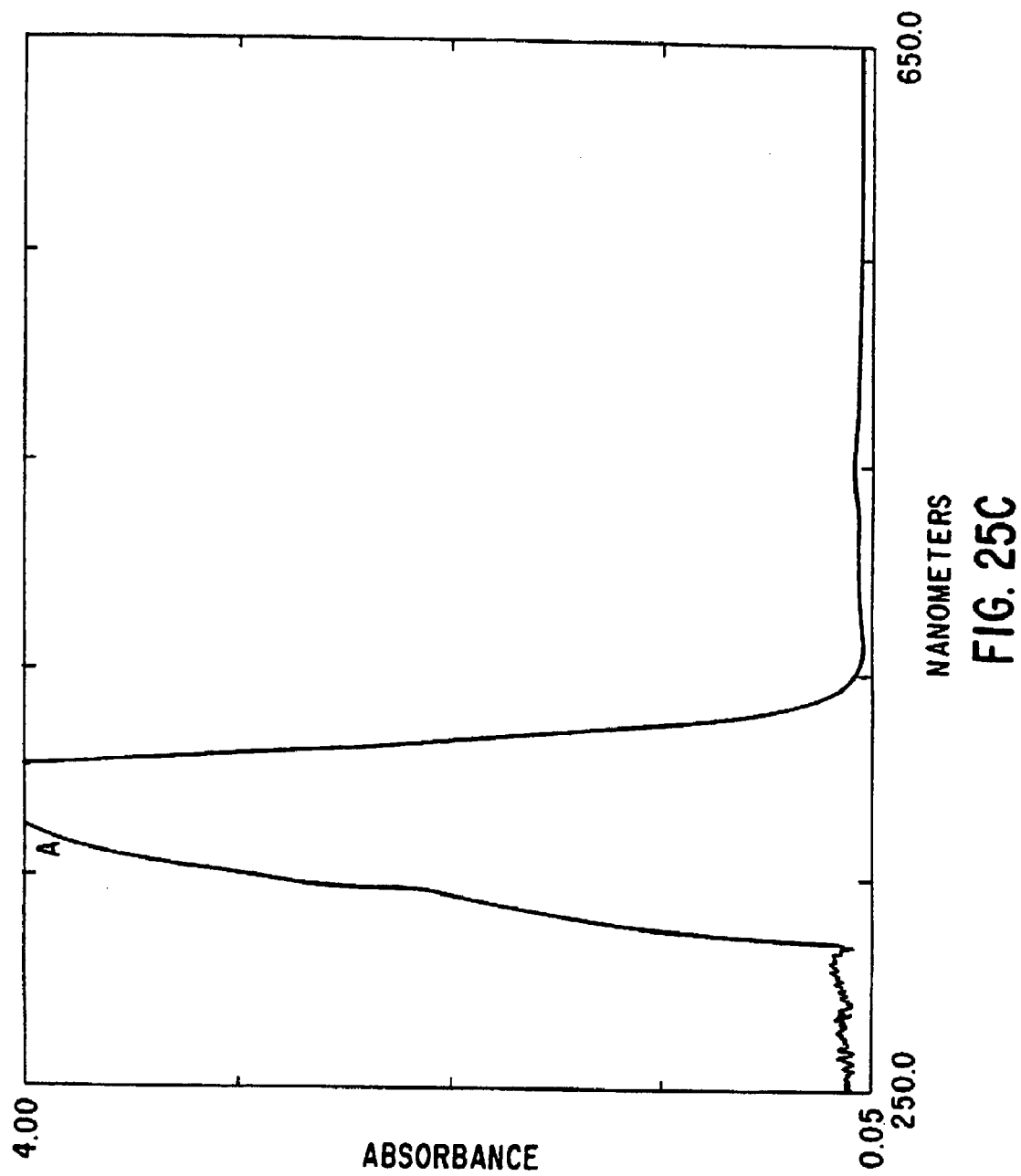

NITROSATED AND NITROSYLATED HEME PROTEINS

RELATED APPLICATIONS

This application is a divisional of U.S. application Ser. No. 09/835,038, filed Apr. 16, 2001, now U.S. Pat. No. 6,583,113; which is a divisional of U.S. application Ser. No. 09/092,622 filed Jun. 5, 1998, issued as U.S. Pat. No. 6,291,424; which is a continuation-in-part of U.S. application Ser. No. 08/409,720, filed Mar. 24, 1995, abandoned; which is a continuation-in-part of U.S. application Ser. No. 08/198,854, filed Feb. 17, 1994, abandoned; which is a divisional of U.S. application Ser. No. 07/943,835, filed Sep. 14, 1992, abandoned; which is a continuation-in-part of U.S. application Ser. No. 07/791,668, filed Nov. 14, 1991, abandoned.

This invention was made with government support under RO1-HL40411, H143344 and RR04870 awarded by the National Institutes of Health. The government may have certain rights in this invention

FIELD OF THE INVENTION

This invention relates to nitrosylation of proteins and amino acids as a therapeutic modality. In particular, the invention relates to S-nitroso-protein compounds and their use as a means to selectively regulate specific protein functions, to selectively regulate cellular function, to endow the protein with new smooth muscle relaxant and platelet inhibitory properties and to provide targeted delivery of nitric oxide to specific bodily sites.

Additionally, the invention relates to nitrosylation of additional sites such as oxygen, carbon and nitrogen, present on proteins and amino acids, as a means to achieve the above physiological effects. The therapeutic effects may be achieved by the administration of nitrosylated proteins and amino acids as pharmaceutical compositions, or by nitrosylation of proteins and amino acids in vivo through the administration of a nitrosylating agent, perhaps in the form of a pharmaceutical composition.

BRIEF DESCRIPTION OF THE BACKGROUND ART

The reaction between low molecular weight thiols, such as cysteine, homocysteine, and N-acetylcysteine, and nitric oxide (NO) has been studied in biological systems. NO has been shown to induce relaxation of vascular smooth muscle, and inhibition of platelet aggregation, through activation of guanylate cyclase and elevation of cyclic GMP levels. Evidence exists that low molecular weight thiols react readily with NO to form S-nitrosothiols, which are significantly more stable than NO itself, and act as potent vasodilators and platelet inhibitors. The adducts have also been proposed as biologically active intermediates in the metabolism of organic nitrates (Ignarro et al., J. Pharmacol. Exp. Ther. 218:739 (1981); Mellion, et al., Mol. Pharmacol. 23:653 (1983); Loscalzo, et al, J. Clin. Invest. 76:966 (1985)).

Many proteins of physiological significance possess intramolecular thiols in the form of cysteine residues. These thiol groups are often of critical importance in the functional properties of such proteins. These sulfhydryl groups are highly specialized and utilized extensively in physiological processes such as metabolic regulation, structural stabilization, transfer of reducing equivalents, detoxification pathways and enzyme catalysis (Gilbert, H. F., "Molecular and Cellular Aspects of Thiol-Disulfide Exchange", Advances in Enzymology, A. Miester, J. Wiley & Sons, Eds. New York 1990, pages 69–172.)

Thiols are also present on those proteins the function of which is to transport and deliver specific molecules to particular bodily tissues. For example, lipoproteins are globular particles of high molecular weight that transport nonpolar lipids through the plasma. These proteins contain thiols in the region of the protein which controls cellular uptake of the lipoprotein (Mahley et al. JAMA 265:78–83 (1991)). Hyper-liproteinemias, resulting from excessive lipoprotein (and thus, lipid) uptake, cause life-threatening diseases such as atherosclerosis and pancreatitis.

The thiol contained in hemoglobin regulates the affinity of hemoglobin for oxygen, and thus has a critical role in the delivery of oxygen to bodily tissues. The reaction between the free NO radical occurs at the iron-binding site of hemoglobin, and not the thiol. As a result, methemoglobin is generated, which impairs oxygen-hemoglobin binding, and thus, oxygen transport. Other proteins such as thrombolytic agents, immunoglobulins, and albumin, possess free thiol groups that are important in regulating protein function.

Protein thiols may, under certain pathophysiological conditions, cause a protein to exert a detrimental effect. For example, cathepsin, a sulfhydryl enzyme involved in the breakdown of cellular constituents, is critically dependent upon sulfhydryl groups for proteolytic activity. However, uncontrolled proteolysis caused by this enzyme leads to tissue damage; specifically lung damage caused by smoking.

The reaction between NO and the thiols of intact protein molecules has previously been studied only to a very limited extent. There is some evidence for the reaction between proteins and nitro(so)-containing compounds in vivo. Investigators have observed that the denitrification of nitroglycerin in plasma is catalyzed by the thiol of albumin (Chong et al., Drug Met. and Disp. 18:61 (1990), and these authors suggest an analogy between this mechanism and the thiol-dependent enzymatic denitrification of nitroglycerin with glutathione S-transferase in a reaction which generates thionitrates (Keene et al., JBC 251:6183 (1976)). In addition, hemeproteins have been shown to catalyze denitrification of nitroglycerin, and to react by way of thiol groups with certain nitroso-compounds as part of the hypothesized detoxification pathway for arylhydroxylamines (Bennett et al., J. Pharmacol. Exp. Ther. 237:629 (1986); Umemoto et al., Biochem. Biophys. Res. Commun. 151:1326 (1988)). The chemical identity of intermediates in these reactions is not known.

Nitrosylation of amino acids can also be accomplished at sites other than the thiol group. Tyrosine, an aromatic amino acid, which is prevalent in proteins, peptides, and other chemical compounds, contains a phenolic ring, hydroxyl group, and amino group. It is generally known that nitration of phenol yields ortho-nitrophenyl and para-nitrophenyl C-nitrosylation products. Nitrosylation of tyrosine, using nitrous acid, has been shown to yield C-nitrosylated tyrosine (Reeve, R. M., Histochem. Cytochem. 16(3):191–8 (1968)), and it has been suggested that this process produces O-nitroso-tyrosine as a preliminary product which then rearranges into the C-nitrosylated product. (Baliga, B. T., Org. Chem. 35(6):2031–2032 (1970); Bonnett et al., J. C. S. Perkin Trans. I; 2261–2264 (1975)).

The chemistry of amino acid side chains, such as those found on tyrosine and other aromatic amino acids, has a critical role in ensuring proper enzymatic function within the body. In addition, the hydroxyl group of tyrosine plays a central role in a variety of cell regulatory functions, with phosphorylation of tyrosine being one such critical cell regulatory event. In addition to possessing bioactive side chains, these aromatic amino acids serve as precursors to numerous important biomolecules such as hormones, vitamins, coenzymes, and neurotransmitters.

The current state of the art lacks chemical methods for modifying the activity and regulating the intermediary cellular metabolism of the amino acids and proteins which play a critical role in biological systems. Moreover, the ability to regulate protein function by nitrosylation was, prior to the present invention, unappreciated in the art.

It is appreciated in the art that, as a result of their increased molecular weight and tertiary structure, protein molecules differ significantly from low molecular weight thiols. Furthermore, because of these differences, it would not be expected that protein thiols could be successfully nitrosylated in the same manner as low molecular weight thiols, or that, if nitrosylated, they would react in the same manner. Furthermore, it would be equally unexpected that nitrosylation of additional sites such as oxygen, carbon and nitrogen would provide a means for regulation of protein function.

Because of the great importance of diverse proteins and amino acids in all biological systems, it would be extremely desirable to have a method for achieving selective regulation of protein and amino acid function. There are virtually unlimited situations in which the ability to regulate amino acid or protein function by nitrosylation would be of tremendous therapeutic significance. Examples of ways in which regulation of modification of function could be achieved would be the following: (1) To enhance or prolong the beneficial properties of the protein or amino acid; (2) to imbue the protein or amino acid with additional beneficial properties; (3) to eliminate detrimental properties of a protein or amino acid; and (4) to alter the metabolism or uptake of proteins or amino acids in physiological systems.

The present invention represents a novel method for achieving these therapeutically significant objectives by regulation of protein and amino acid function with either of the following methods: (1) administration of particular nitrosylated proteins or amino acids to a patient; and (2) nitrosylation of a protein or amino acid in vivo by the administration of a nitrosylating agent to a patient. In addition, the invention represents the discovery of exemplary S-nitroso-proteins and amino acids of great biological and pharmacological utility.

SUMMARY OF THE INVENTION

This invention is based on the discovery by the inventors that nitrosylating thiols, as well as oxygen, carbon and nitrogen present on proteins and amino acids provides a means for achieving selective regulation of protein and amino acid function. This concept can be employed to generate S-nitroso-protein compounds, as well as other nitrosylated proteins and amino acids, which possess specific properties, and can be directly administered to a patient. In the alternative, the invention provides a means for in vivo regulation of protein or amino acid function by nitrosylation. The invention is therefore directed to novel S-nitroso-proteins and the therapeutic uses thereof, as well as the nitrosylation of proteins in vivo, as a therapeutic modality. The invention is also directed to nitrosylation of oxygen, carbon and nitrogen sites of proteins and amino acids, as a therapeutic modality.

In particular, this invention is directed to compounds comprising an S-nitroso-enzyme. Enzymes contained in this compound include tissue-type plasminogen activator, streptokinase, urokinase and cathepsin.

This invention is also directed to compounds comprising S-nitroso-lipoprotein. Lipoproteins which may be contained in the compound include chylomicrons, chylomicron remnant particles, very low-density lipoprotein (VLDL), intermediate-density lipoprotein (IDL), low-density lipoprotein (LDL) high-density lipoprotein (HDL) and lipoprotein (a).

This invention is also directed to compounds comprising S-nitroso-immunoglobulin. Immunoglobulins contained in this compound include IgG, IgM, IgA, IgD, IgE.

The invention is also directed to the compound S-nitroso-hemoglobin.

The invention is also directed to the compound S-nitroso-myoglobin.

The invention is also directed to pharmaceutical compositions containing the compounds of the invention, together with a pharmaceutically acceptable carrier.

The invention is also directed to a method for regulating oxygen delivery to bodily sites by administering pharmaceutical compositions containing S-nitroso-hemoglobin and S-nitroso-myoglobin.

The invention also relates to methods for effecting vasodilation, platelet inhibition, and thrombolysis; and for treating cardiovascular disorders, comprising administering the pharmaceutical compositions of the invention to an animal.

This invention is also directed to a method for effecting platelet inhibition, comprising administering a pharmaceutical composition comprised of S-nitroso-albumin. An additional embodiment of the invention comprises the method for causing relaxation of airway smooth muscle and for the treatment or prevention of respiratory disorders, comprising administering a pharmaceutical composition containing S-nitroso-albumin.

This invention also is directed to a method for causing vasodilation, platelet inhibition and thrombolysis, comprising administering a nitrosylating agent to an animal.

This invention also is directed to a method for regulation of protein function in vivo, comprising administering a nitrosylating agent to an animal.

The invention is directed to a method for preventing the uptake of a protein by cells, comprising administering a nitrosylating agent to a patient.

The invention is also directed to a method for causing relaxation of non-vascular smooth muscle, comprising administering the pharmaceutical compositions of the invention to an animal.

The invention is also directed to a method for regulating the function of proteins in which the thiol is bound to a methyl group, comprising the steps of removing the methyl groups from the protein by selective de-methylation, and reacting the free thiol group with a nitrosylating agent.

The invention is also directed to a method for regulating the function of a protein which lacks a free thiol group, comprising the steps of adding a thiol group to the protein, and reacting the thiol group with a nitrosylating agent.

The invention is also directed to a method for regulating cellular function, comprising the S-nitrosylation of a protein which is cellular component or which affects cellular function.

The invention is also directed to a method for delivering nitric oxide to specific, targeted sites in the body comprising administering an effective amount of the pharmaceutical compositions of the invention to an animal.

The invention is also directed to a method for inhibiting platelet function, comprising the nitrosylation of a protein or amino acid at other sites, in addition to thiol groups, which are present on said protein or amino acid.

The invention is also directed to a method for causing vasodilation, comprising the nitrosylation of a protein or amino acid at other sites, in addition to thiol groups, which are present on said protein or amino acid.

The invention is also directed to a method for relaxing smooth muscle, comprising the nitrosylation of a protein or amino acid at other sites, in addition to thiol groups, which are present on said protein or amino acid.

The invention is also directed to a method for regulating cellular function, comprising the nitrosylation of a protein or amino acid at other sites, in addition to thiol groups, which are present on said protein or amino acid.

The invention is also directed to a method for delivery of nitric oxide to specific, targeted sites in the body, comprising the nitrosylation of a protein or amino acid at other sites, in addition to thiol groups, which are present on said protein or amino acid.

The sites which are nitrosylated are selected from the group consisting of oxygen, carbon and nitrogen.

The invention is also directed to a method for inhibiting platelet function, comprising administering a pharmaceutical composition comprised of a compound selected from the group consisting of any S-nitroso-protein.

The invention is also directed to a method for causing vasodilation, comprising administering a pharmaceutical composition comprised of a compound selected from the group consisting of any S-nitroso-protein.

The invention is also directed to a method for treatment or prevention of cardiovascular disorders, comprising administering a pharmaceutical composition comprised of a compound selected from the group consisting of any S-nitroso-protein.

The invention is directed to a method for relaxing non-vascular smooth muscle, comprising administering a pharmaceutical composition comprised of a compound selected from the group consisting of any S-nitroso-protein.

The invention is also directed to a method for treatment or prevention of respiratory disorders, comprising administering a-pharmaceutical -composition comprised of a-compound selected from the group consisting of any S-nitroso-protein.

The invention is also directed to a method for delivering nitric oxide to specific, targeted sites in the body, comprising administering a pharmaceutical composition comprised of a compound selected from the group consisting of any S-nitroso-protein.

BRIEF DESCRIPTION OF THE DRAWINGS

FIG. 1. S—NO-t-PA spectroscopy.

FIG. 5. Double reciprocal plots for S—NO-t-PA. Results are expressed as mean±S. D. (n=3).

FIG. 5a: Double reciprocal plot 1/v versus 1/s for t-PA and S—NO-t-PA generated against the chromogenic substrate S2288.

FIG. 5b: The curves for activation of glu-plasminogen (0.1–10 μM) by t-PA and S—NO-t-PA, generated using the plasmin-specific chromogenic substrate S2251.

FIGS. 11A–11B. Representative tracings of vessel relaxation and platelet inhibition caused by S-nitroso-BSA (S—NO-BSA).

FIG. 11a: Illustrative tracings comparing the platelet inhibitory effects of (a) S—NO-BSA; (b) NaNO$_2$ ; (c) BSA; (d) iodoacetamide-treated BSA exposed to NO generated from acidified NaNO$_2$.

FIG. 11b: Illustrative tracings comparing the vasodilatory effects of (a) BSA (1.4 μM); (b) iodoacetamide-treated BSA treated with NO generated from acidified NaNO$_2$ as described in FIG. 3a; (c) S—NO-BSA (1.4 μM) after platelets were pretreated with 1 μM methylene blue for ten minutes; (d) S—NO-BSA (1.4 μM).

| 21a: | [$^{15}$N]-NMR spectrum. |
| 21b: | [$^1$H]-NMR spectrum. |
| 21c: | FTIR spectrum |
| 21d: | UV spectrum for 1.8 mM of tyrosine. |
| 21e: | UV spectrum for 34 mM of tyrosine. |

Figure 22:
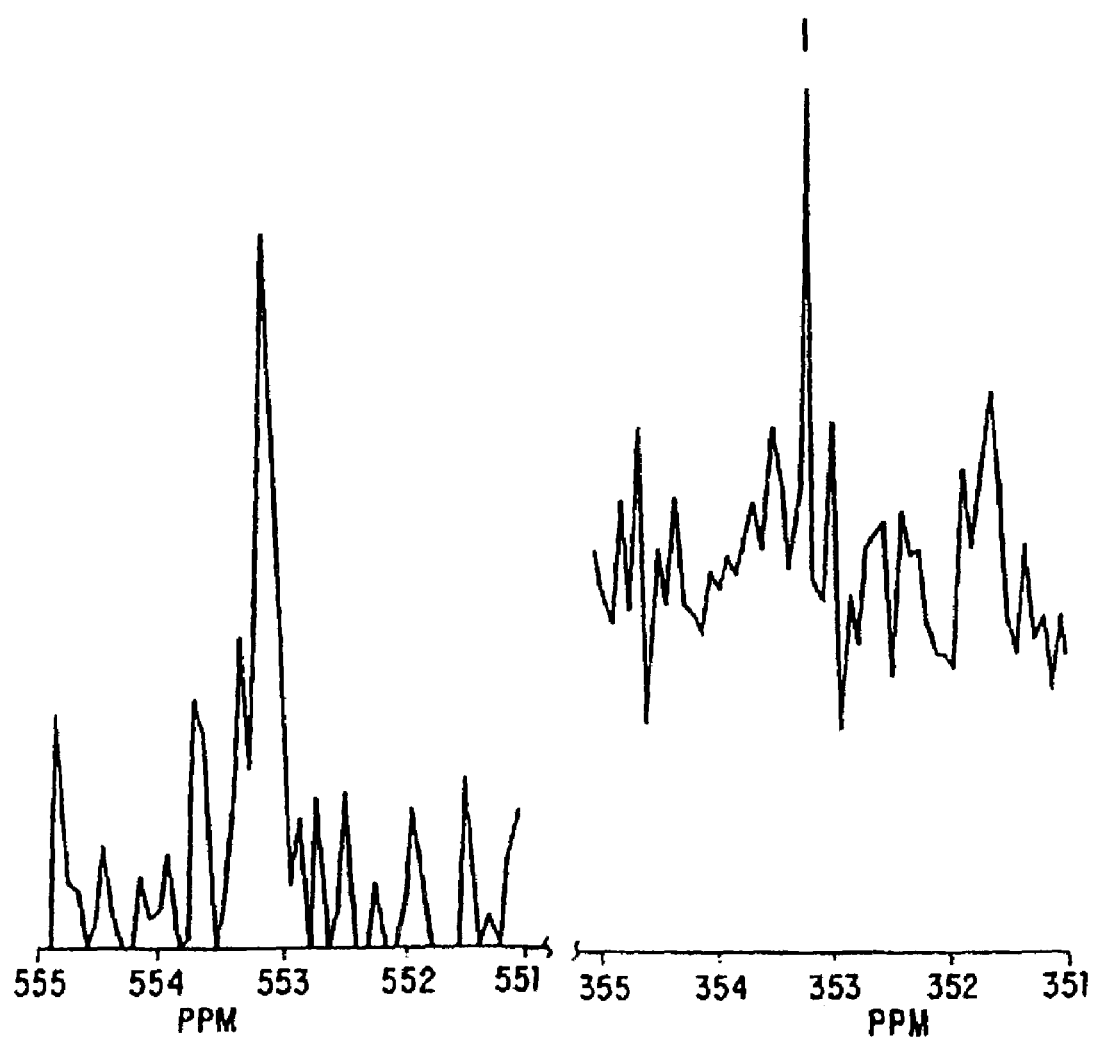
Figure 23A:
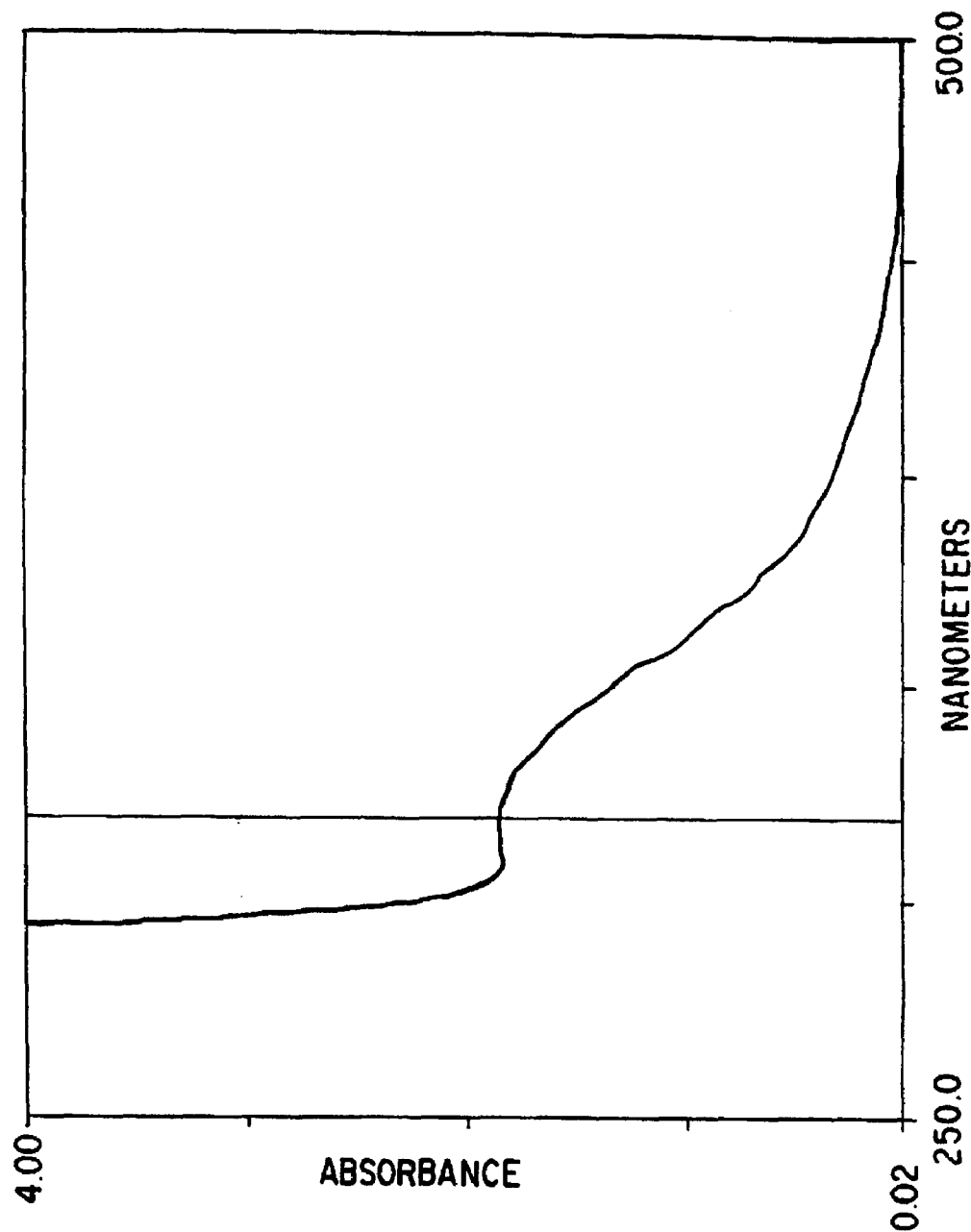
Figure 23B:
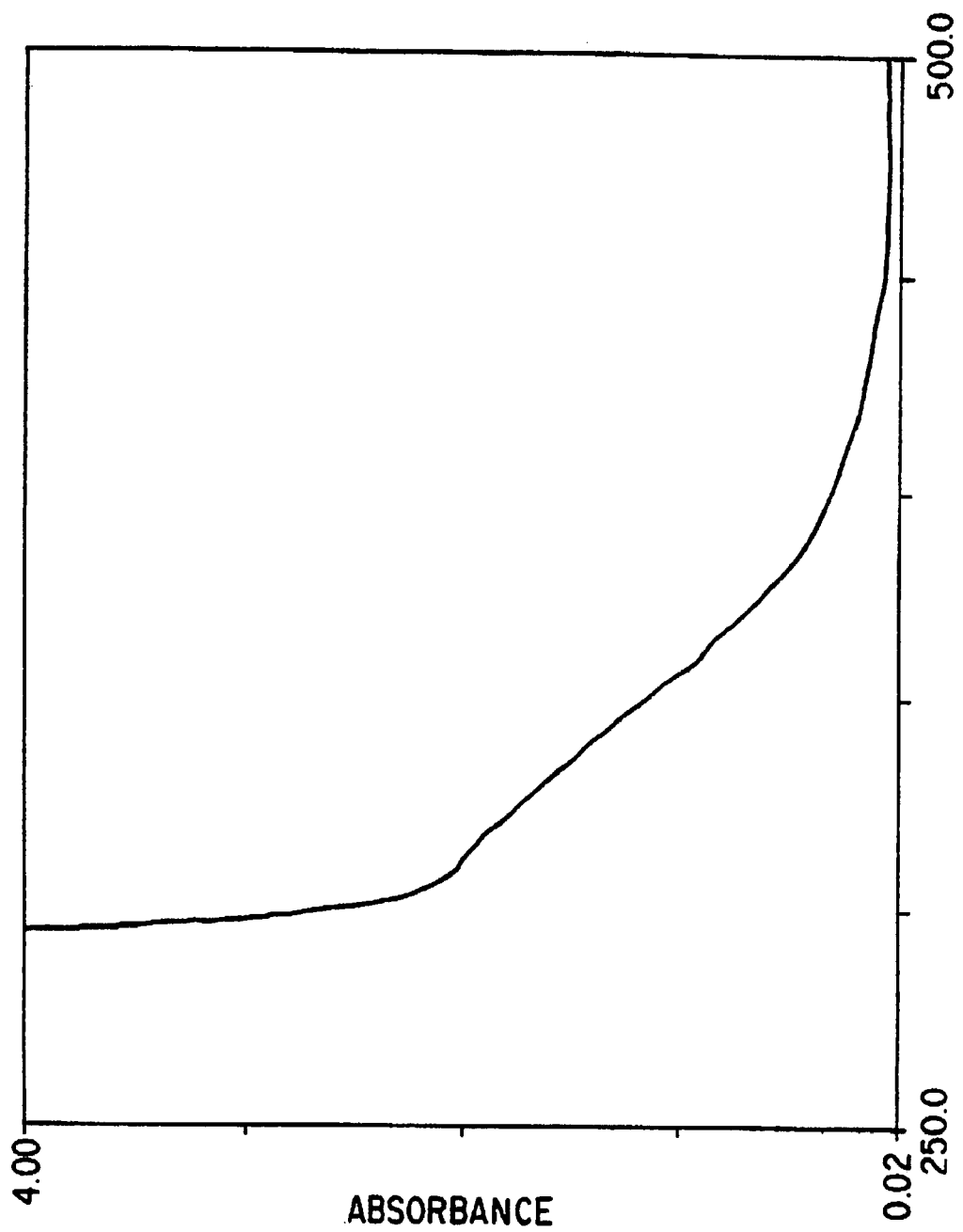
Figure 23C:
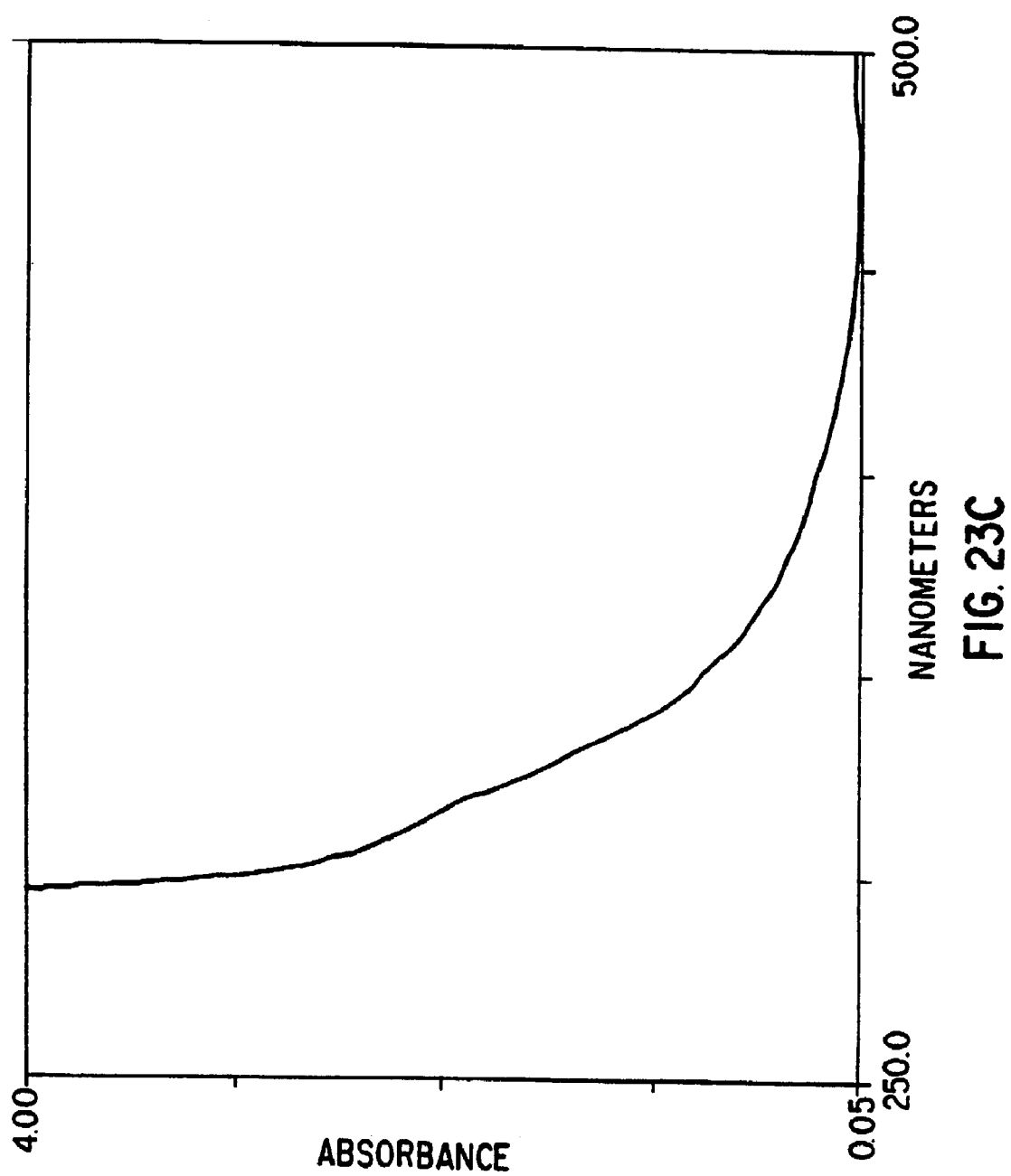
Figure 23D:
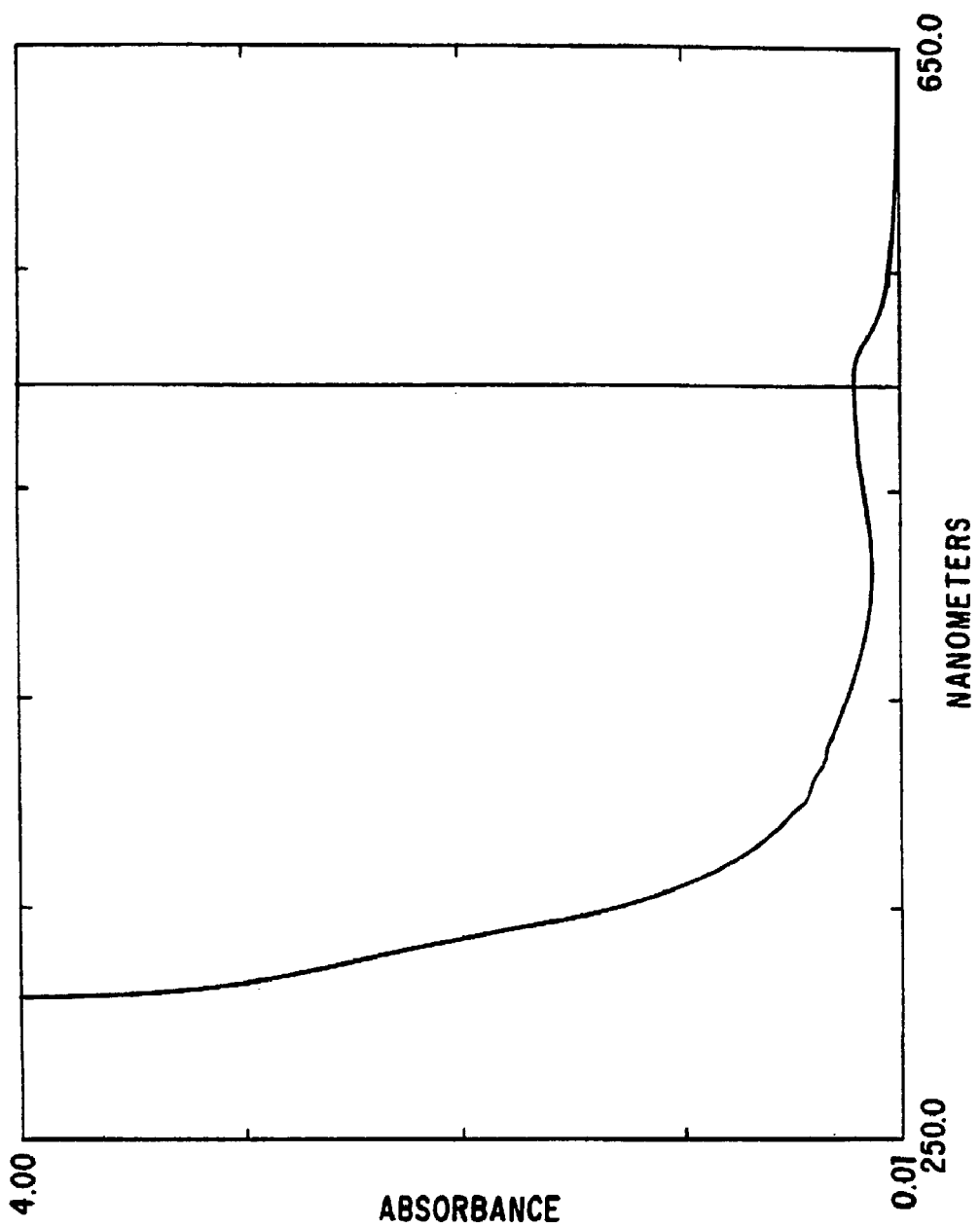
Figure 23E:
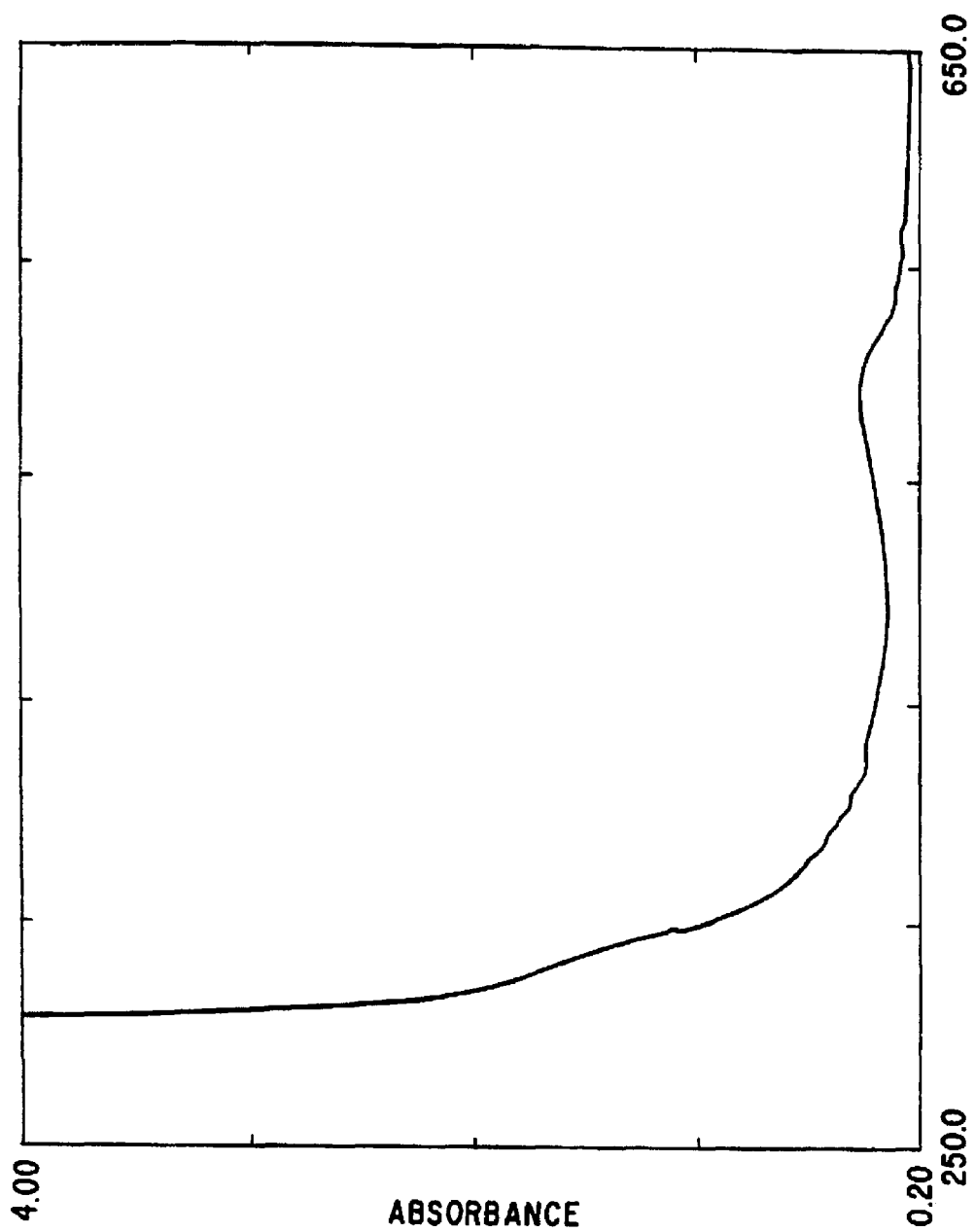

FIG. 22. Nitrosylation of L-phenylalanine; [$^{15}$N]-NMR spectrum.

FIG. 23. UV spectrum for nitrosylation of tryptophan.

| | |
|---|---|
| 23a: | 5 minute reaction time. |
| 23b: | 10 minute reaction time. |
| 23c: | 15 minute reaction time. |
| 23d: | 30 minute reaction time. |
| 23e: | 60 minute reaction time. |

Figure 24:
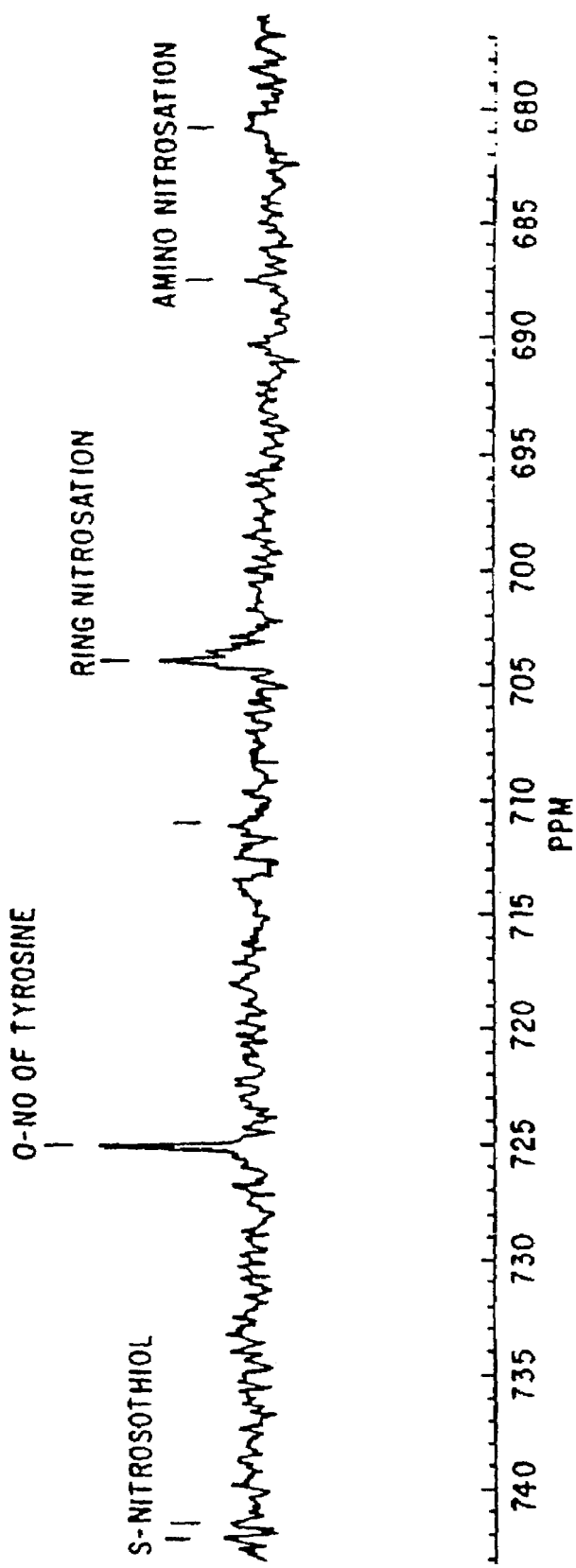

FIG. 24. [$^{15}$N] NMR for nitrosylated bovine serum albumin.

Figure 25A:
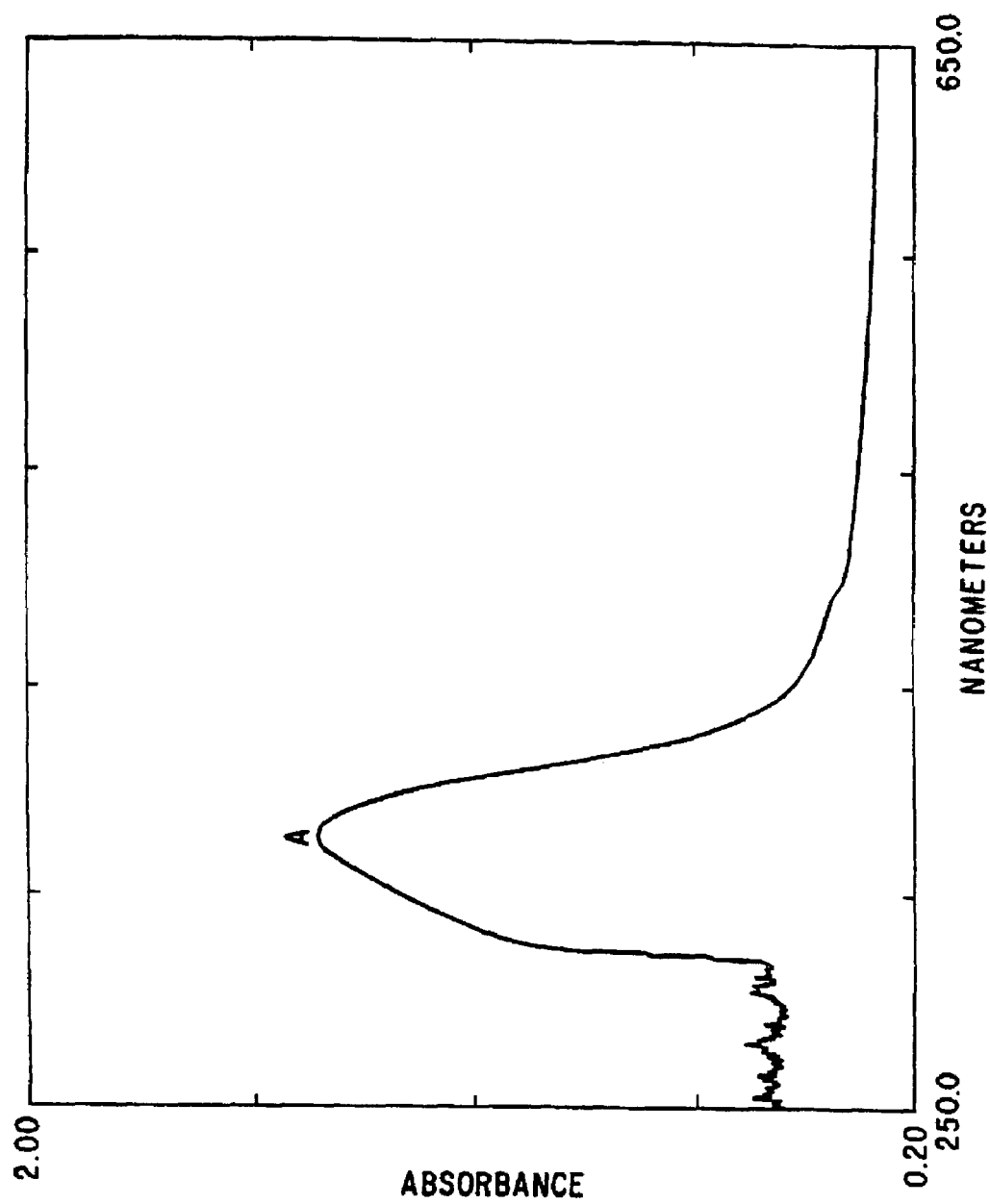
Figure 25B:
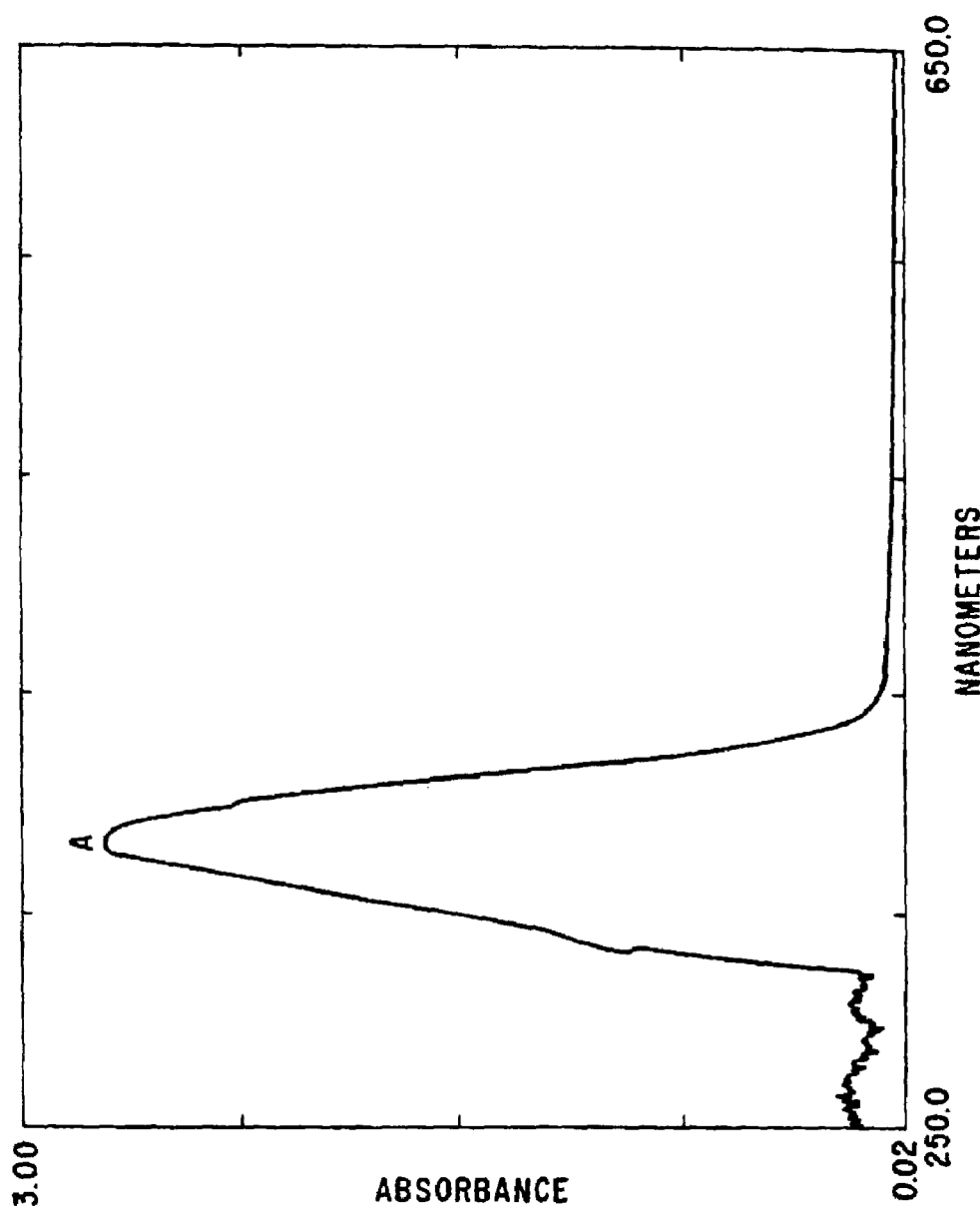

FIG. 25. UV spectrum for time-dependent NO loading of BSA.

| | |
|---|---|
| 25a: | 1 minute reaction time. |
| 25b: | 5 minute reaction time. |
| 25c: | 30 minute reaction time. |

Figure 26:
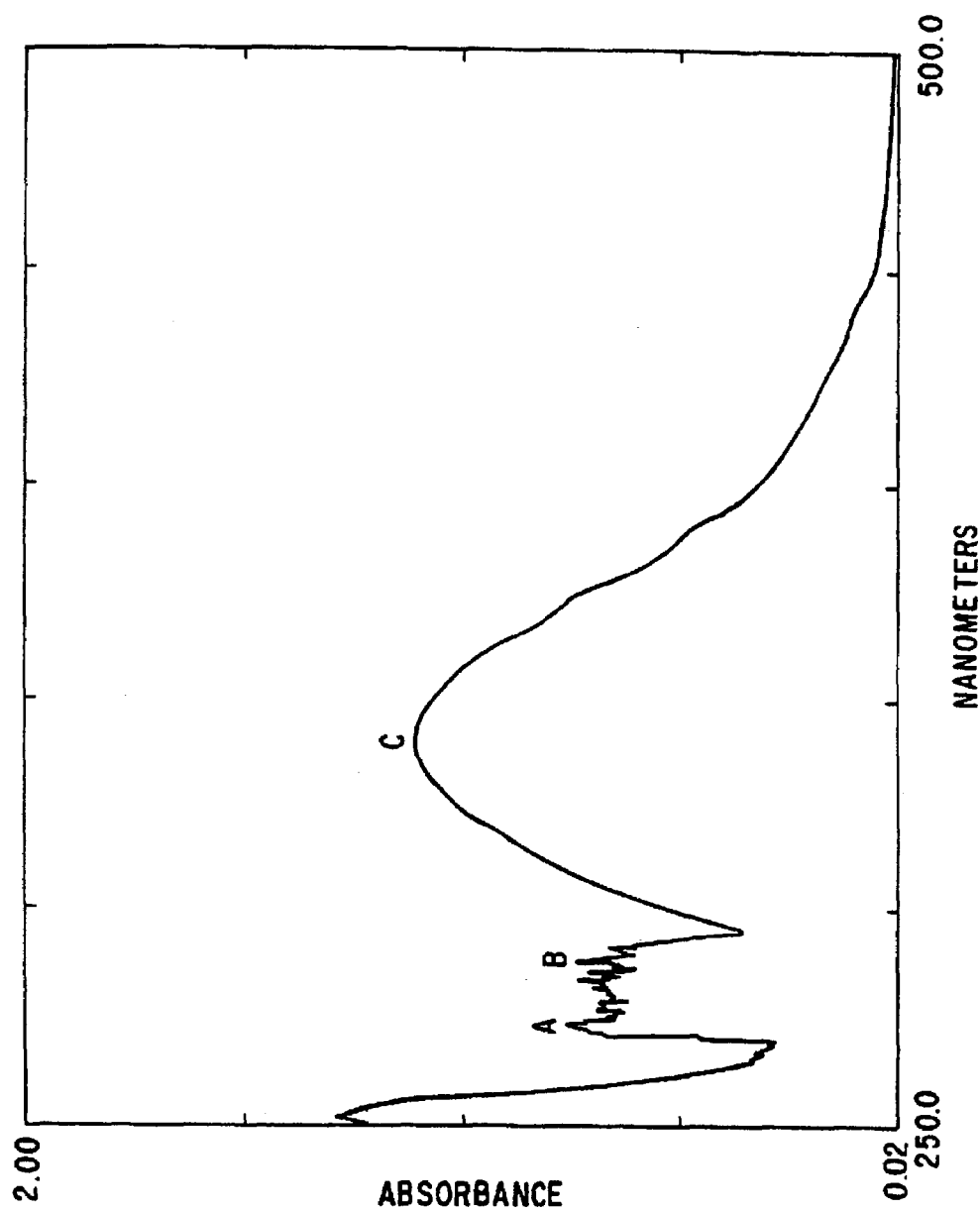
Figure 27:
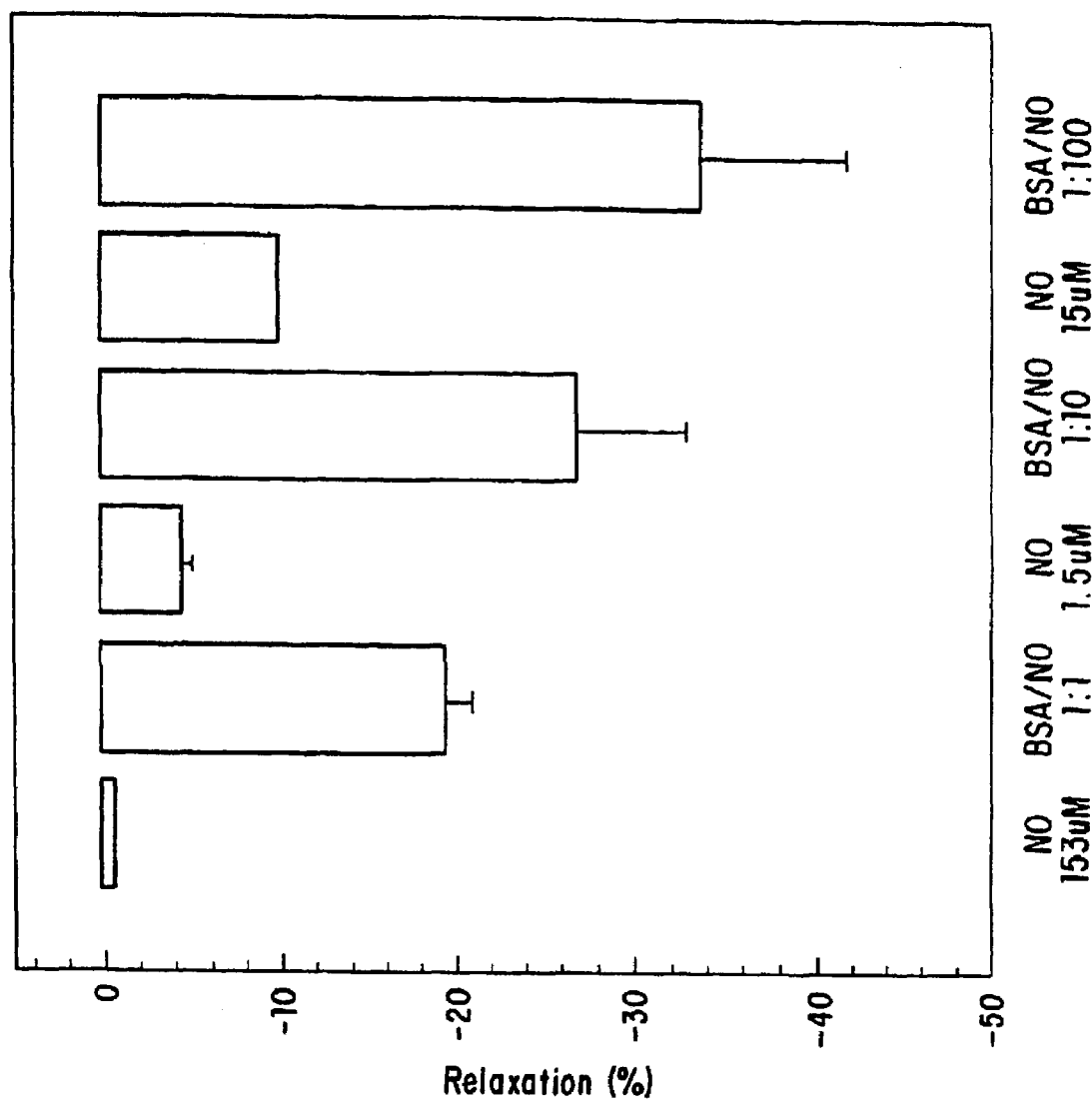
Figure 28:
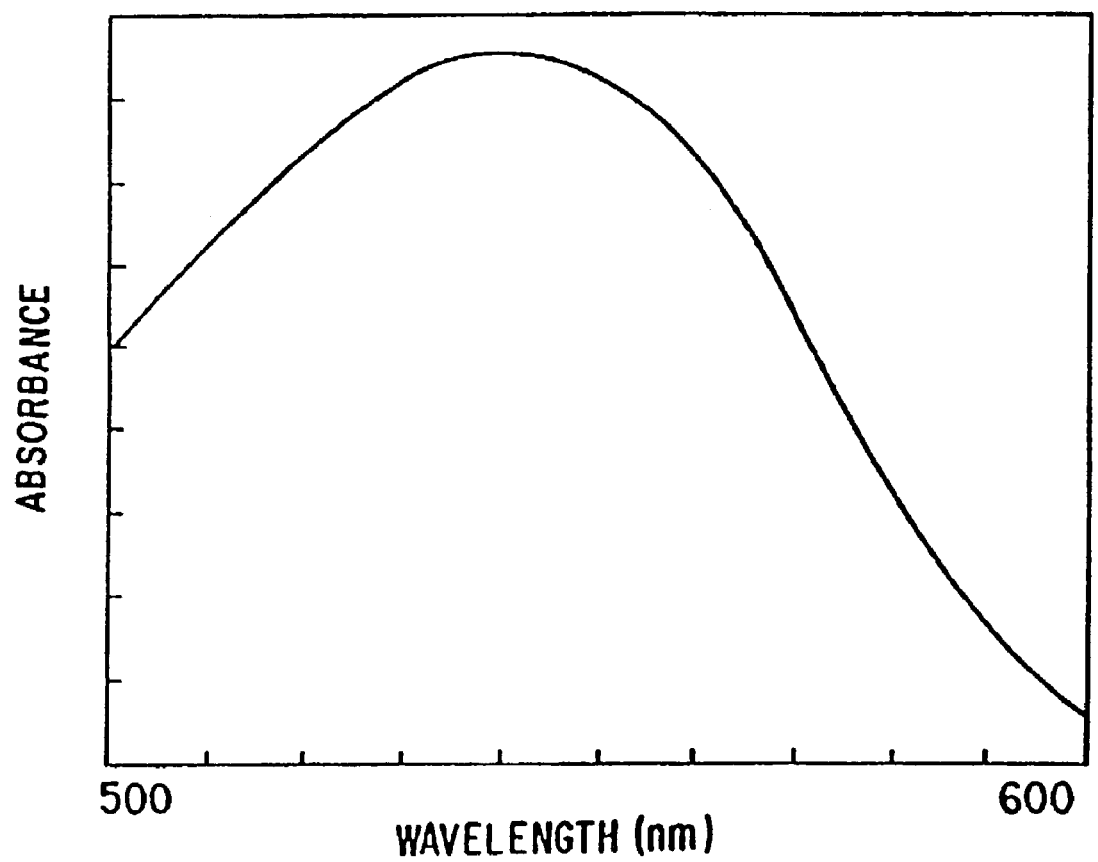
Figure 29:
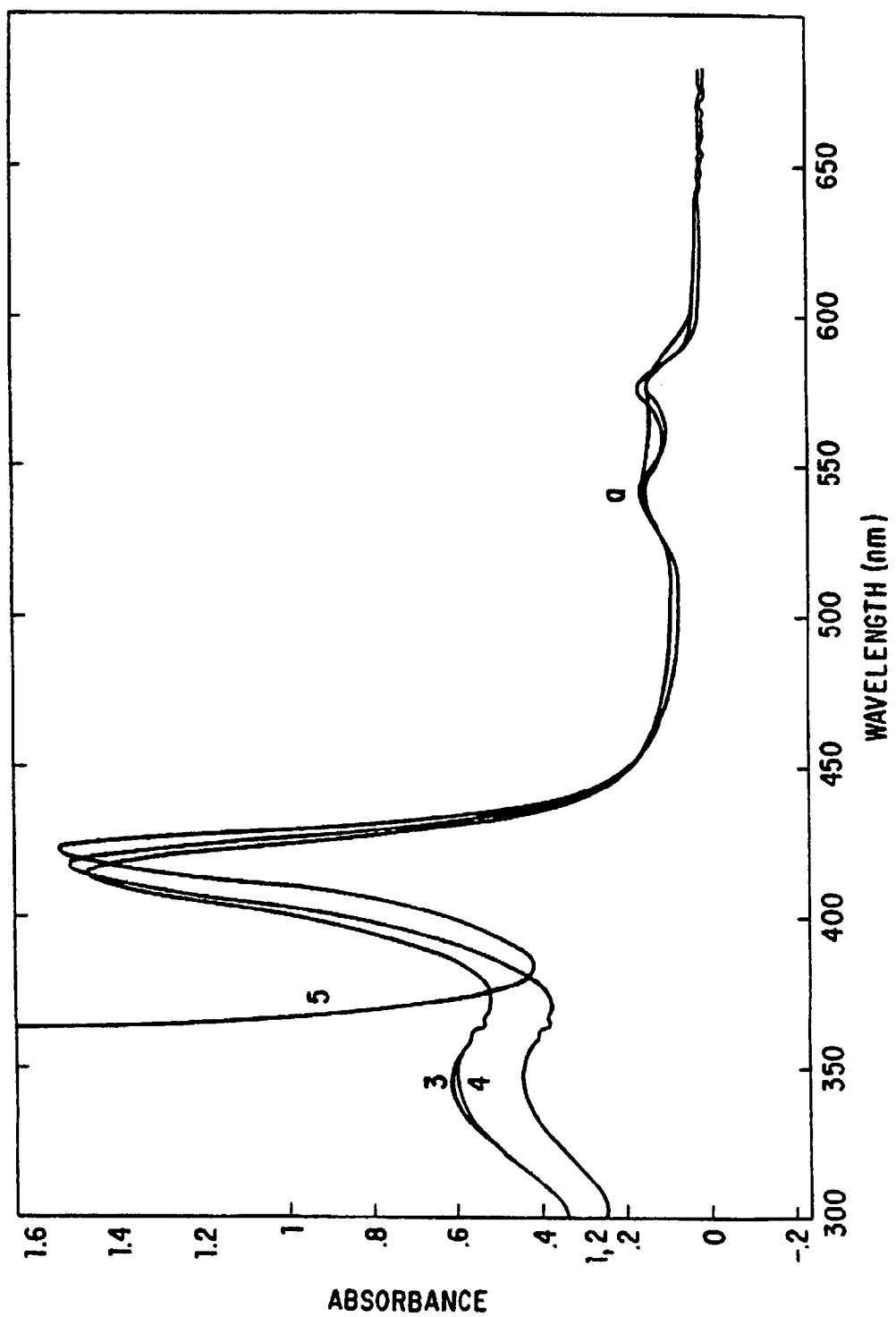
Figure 30:
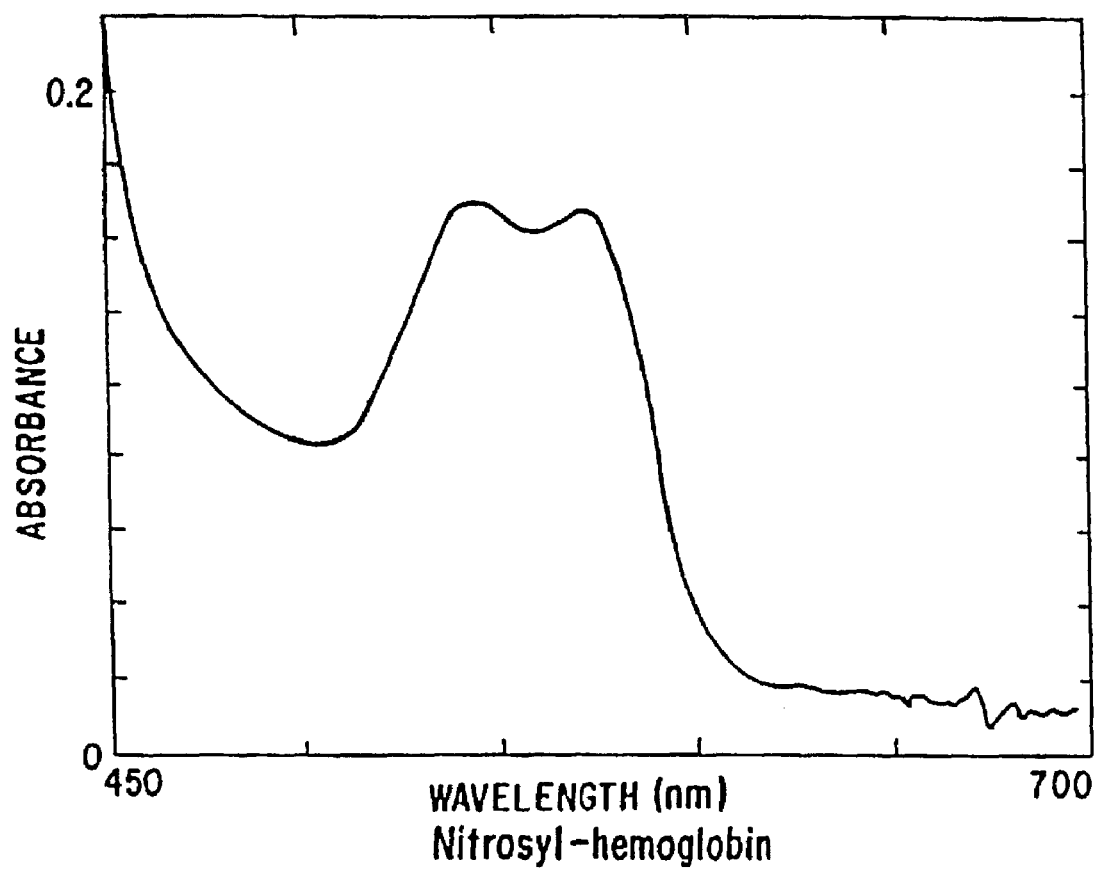

FIG. 26. Nitrosylation of t-PA.
FIG. 27. Vasodilatory effects of NO-loaded BSA.
FIG. 28: S-nitrosylation of hemoglobin.
FIG. 29: UV spectrum of hemoglobin incubated with S-nitroso-N-acetylcysteine.
FIG. 30: Reaction of nitric oxide at the iron-binding site of hemoglobin.

DETAILED DESCRIPTION OF THE PREFERRED EMBODIMENTS

The invention is based on the discovery by the inventors that nitrosylation of proteins and amino acids provides a means by which protein and amino acid function may be selectively regulated, modified or enhanced. The term "nitrosylation" refers to the addition of NO to a thiol group (SH), oxygen, carbon or nitrogen by chemical means. The source of NO may be endogenous NO or endothelium-derived relaxing factor, or other nitrosylating agents, such as nitroglycerin, nitroprusside, nitrosothiols, nitrous acid or any other related compound.

The term "regulated" means effective control of the activity of a protein or amino acid, in a selective manner so as to cause the protein or amino acid to exert a desired physiological effect.

The term "modified" means to effectively alter the activity of a protein or amino acid in a selective manner, so as to cause the protein or amino acid to exert a desired physiological effect. The term "enhanced" means to alter effectively the activity of a protein or amino acid in a selective manner, so as to cause an increase or improvement in the activity of the protein or amino acid, or endow the protein or amino acid with additional capabilities. The term "activity" refers to any action exerted by the protein or amino acid which results in a physiological effect.

The inventors have investigated to reaction of NO with protein thiols and have demonstrated that a variety of proteins of biological significance and relative abundance can be S-nitrosylated. S-nitrosylation of proteins endows these molecules with potent and long-lasting NO-like effects of vasodilation and platelet inhibition, mediated by guanylate cyclase activation, and also provides a means for achieving selective regulation of particular protein functions.

To develop the S-nitroso-protein compounds of the invention, certain thiol-containing proteins which are representative of various functional classes were nitrosylated. Such proteins include enzymes, such as tissue-type plasminogen activator (t-PA) and cathepsin B; transport proteins, such as lipoproteins, hemoglobin, and serum albumin; and biologically protective proteins, such as immunoglobulins.

The data demonstrate that 1) NO can react with thiol groups in proteins to form S-nitrosothiols; 2) this reaction occurs under physiological conditions; 3) these compounds are biologically active, exhibiting vasodilatory and antiplatelet properties that are independent of their method of synthesis; 4) the long chemical half-lives of S-nitroso-proteins vis-a-vis the half life of NO is reflected in their different relaxation kinetics; S-nitroso-proteins, through activation of guanylate cyclase, is fully consistent with that of other nitroso-compounds; although the possibility of other mechanisms by which S—NO-proteins can produce biologic effects cannot be excluded, such as the transfer of NO to another protein thiol, the function of which is thereby modulated. (Craven et al. J. Biol. Chem. 253:8433 (1978); Katsuki et al. J. Cyc. Nuc. Prot. Phos. Res. 3:23 (1977); Osborne et al., J. Clin. Invest. 83:465 (1989)).

One embodiment of the invention relates to S-nitroso-enzyme compounds, derived from nitrosylation of enzymatic proteins.

A particular aspect of this embodiment relates to the compound, S-nitroso-t-PA (S—NO-t-PA), derived from the nitrosylation of tissue-type plasminogen activator (t-PA).

Acute occlusive events are precipitated by thrombogenic stimuli and alterations in flow dynamics within the vessel. Platelet activation, augmented local vasoconstriction, and recruitment of the coagulation system each plays a major role in the subsequent development of a thrombus (Marder et al., New Engl. J. Med. 318:1512,1520 (1988)). t-PA is one of the products secreted by blood vessel endothelium, which specifically counteracts these thrombogenic mechanisms. t-PA, a serine protease, converts plasminogen to plasmin on fibrin and platelet thrombi, which in turn induces fibrinolysis and platelet disaggregation. Loscalzo et al., New Engl. J. Med. 319(14):925–931 (1989); Loscalzo et al., J. Clin. Invest. 79:1749–1755 (1987).

Attempts have been made to improve the thrombolytic, efficacy and pharmacological properties of plasminogen activators, such as t-PA. In light of the role of platelets in clot formation and in reocclusive vascular events, one major focus has involved the use of ancillary antiplatelet therapy. Some success has been achieved with aspirin (ISIS-2 Lancet 2:349–360 (1988)), and other benefits are reported for several newer antiplatelet compounds (Gold, H. K. New Engl. J. Med. 323:1483–1485 (1990)). Attempts have also been made to improve the functional properties of the plasminogen activator itself through site-directed mutagenesis and synthesis of hybrid molecules and biochemical conjugates (Runge et al., Circulation 79:217–224 (1989); Vaughan et al., Trends Cardiovasc. Med. January/February: 1050–1783 (1991)).

Motivated by the need for a plasminogen activator with improved thrombolytic efficacy and anti-thrombogenic properties, the inventors discovered that nitrosylation of t-PA creates a new molecule (S—NO-t-PA) which has improved thrombolytic capability, (e.g., the enzymatic activity of the enzyme is enhanced) as well as vasodilatory and platelet inhibitory effect. The inventors demonstrated that S-nitrosylation significantly enhances the bioactivity of t-PA, without impairing the catalytic efficiency or other domain-specific functional properties of the enzyme.

In particular, S-nitrosylation of t-PA at the free cysteine, cys 83, confers upon the enzyme potent antiplatelet and vasodilatory properties, without adversely affecting its catalytic efficiency or the stimulation of this activity by fibrin (ogen). In addition, the S-nitrosothiol group does not appear to alter the specific binding of t-PA to fibrin(ogen) or the interaction of t-PA with its physiological serine protease inhibitor, PAI-1. The proteolytic activity, fibrin(ogen)-binding properties are regions for interaction with PAI-1 reside in several functional domains of the molecule that are linearly separate from the probable site of S-nitrosylation in the growth factor domain (cys 83). Thus, chemical modification of t-PA by NO does not markedly alter functional properties of t-PA residing in other domains. In addition, S-nitrosylation enhances the catalytic efficiency of t-PA against plasminogen, and increases its stimulation by fibrinogen.

NO is highly labile and undergoes rapid inactivation in the plasma and cellular milieu. This suggests that the reaction between NO and the protein thiol provides a means of stabilizing NO in a form in which its bioactivity is preserved. Specifically, S—NO-t-PA is a stable molecule under physiologic conditions and, much like NO, is capable of vasodilation and platelet inhibition mediated by cyclic GMP. Stabilizing NO in this uniquely bioactive form creates a molecule with intrinsic vasodilatory, antiplatelet, and fibrinolytic properties, which enable it to counteract each of the major thrombogenic mechanisms.

Another aspect of this embodiment relates to the administration of S—NO-t-PA as a therapeutic agent to an animal for the treatment and prevention of thrombosis. Current thrombolytic strategies are based on the understanding of the endogenous mechanisms by which the endothelium protects against thrombogenic tendencies. In particular, platelet inhibition and nitrovasodilation are frequently used concomitant therapies with which to enhance reperfusion by plasminogen activators as well as to prevent rethrombosis (Gold, H. K. New Engl. J. Med. 323:1483–1485 (1990); (Marder et al., New Engl. J. Med. 318:1512–1520 (1988)).

Administration of S—NO-t-PA to a patient in need thereof provides a means for achieving "fibrin-selective" thrombolysis, while simultaneously attenuating the residual thrombogenicity resulting from simultaneous platelet activation and thrombin generation during thrombolysis. Furthermore, by virtue of its fibrin binding properties, S—NO-t-PA provides targeted delivery of the antiplatelet effects of NO to the site of greatest platelet activation, the actual fibrin-platelet thrombus. S—NO-t-PA has therapeutic application in the treatment or prevention of conditions which result from, or contribute to, thrombogenesis, such as atherothrombosis, myocardial infarction, pulmonary embolism or stroke.

In summary, S—NO-t-PA possesses unique properties that facilitate dispersal of blood clots and prevent further thrombogenesis. The discovery of this unique molecule provides new insight into the endogenous mechanism(s) by which the endothelium maintains vessel patency and offers a novel, and beneficial pharmacologic approach to the dissolution of thrombi.

Another aspect of this embodiment relates to the compounds derived from the nitrosylation of other thrombolytic agents, such as streptokinase, urokinase, or a complex containing one or more thrombolytic agents, such as streptokinase, urokinase, or t-PA. These compounds may also be administered to an animal, in the same manner as S—NO-t-PA for the treatment and prevention of thrombosis.

An additional aspect of this embodiment relates to compounds derived from the nitrosylation of other enzymes. One particular compound is S—NO-cathepsin, derived from the nitrosylation of cathepsin B, a lysosomal cysteine protease. The inventors have demonstrated that S—NO cathepsin exerts a vasodilatory and platelet inhibitory effect. Thus, this compound may be administered as a therapeutic agent to an animal, to promote vasodilation and platelet inhibition, and to treat or prevent cardiovascular disorders.

Another embodiment of the invention relates to S-nitroso-lipoprotein compounds derived from the nitrosylation of lipoproteins. Such lipoproteins include chylomicrons, chylomicron remnant particles, very low-density lipoprotein (VDL), low-density lipoprotein (LDL), intermediate-density lipoprotein (IDL), and high density lipoprotein (HDL) and lipoprotein (a). The inventors have demonstrated that S-nitroso-lipoproteins exert vasodilatory and platelet inhibitory effect. Thus, these compounds may be administered as a therapeutic agent, to an animal, to promote vasodilation and platelet inhibition, and to treat or prevent cardiovascular disorders.

An additional embodiment of the invention involves the in vivo nitrosylation of lipoproteins as a means for regulating cellular uptake of lipoproteins. Consequently, nitrosylation provides a means for regulating lipid uptake, and treating or preventing disorders associated with hyperlipidemias, such as atherosclerosis.

Another embodiment of the invention relates to the S-nitroso-immunoglobulin compounds derived from the nitrosylation of immunoglobulins. Such immunoglobulins may include IgG, IgM, IgA, IgD, or IgE. The inventors have demonstrated that these compounds exert vasodilatory and platelet inhibitory effect. Thus, these compounds may be administered as therapeutic agents, to an animal, to promote vasodilation and platelet inhibition, and to treat or prevent cardiovascular disorders. The half lives of these compounds, in the order of one day, produce unique, long-lasting vasodilatory effects which are notably different from those of low molecular weight nitroso-compounds.

An additional embodiment of the invention is the compound S-nitroso-hemoglobin, derived from the nitrosylation of hemoglobin. This compound may be used as therapeutic agent to promote vasodilation and platelet inhibition, and to treat or prevent cardiovascular disorders.

As demonstrated by the inventors, S-nitrosylation of hemoglobin increases its oxygen-binding capacity. Hemoglobin is a globular protein, which binds reversibly to blood oxygen through passive diffusion from entry of air into the lungs. Hemoglobin-oxygen binding greatly increases the capacity of the blood to transport oxygen to bodily tissues; thus, the binding affinity between hemoglobin and oxygen is a critical factor in determining the level of oxygen transport to the tissues. The thiol group on the hemoglobin molecule regulates the affinity of hemoglobin for oxygen. The inventors have demonstrated that some S-nitrosothiols, such as S-nitroso-proteins do not react with the iron-binding site of hemoglobin, as does NO., but instead, bind to the thiol group. Thus, methemoglobin formation is prevented and hemoglobin-oxygen binding is unimpaired.

Furthermore, the inventors have also demonstrated that S-nitrosylation of hemoglobin not only prevents impairment of binding, but actually increases hemoglobin-oxygen binding. Therefore, another embodiment of the invention involves the administration of S——NO-hemoglobin or the in vivo nitrosylation of hemoglobin, to increase the oxygen-carrying capacity of the blood, and oxygen transport to bodily tissues. As a result, these compounds may be useful in the treatment of disorders which are associated with insufficient oxygen transport, or in clinical situations in which increased oxygen transport is needed. Examples of such clinical situations include, but are not limited to, hypoxic disorders resulting from pneumothorax, airway obstruction, paralysis or weakness of the respiratory muscles, inhibition of respiratory centers by drug or other agents, or other instances of decreased pulmonary ventilation. Additional clinical indications include impaired alveolar gas diffusion such as occurs in interstitial fibrosis, bronchiole constriction, pulmonary edema, pneumonia, hemorrhage, drowning, anemias, arteriovenous shunts, and carbon monoxide poisoning.

In addition, S——NO-hemoglobin may also be used to modulate the delivery of carbon monoxide or nitric oxide (bound to hemoglobin) to bodily tissues.

In addition, any thiol-containing heme proteins may be nitrosylated and used to enhance the oxygen-carrying capacity of the blood.

An additional embodiment of the invention is the compound S-nitroso-myoglobin, derived from the nitrosylation of myoglobin, a protein which also transports oxygen. This compound may be used as a therapeutic agent to promote vasodilation and platelet inhibition, and to treat or prevent cardiovascular disorders.

Another embodiment of the invention relates to a method for using S-nitroso-proteins as a means for providing targeted delivery of NO. The term "targeted delivery" means that NO is purposefully transported and delivered to a specific and intended bodily site. In the same manner as S—NO-t-PA, S—NO-immunoglobulin can be modified, by cationic modification of the heavy chain, to provide targeted delivery of NO to the basement membrane of the glomerulus in the kidney. Successful delivery of four NO molecules per immunoglobulin have been directed to the kidney basement membrane in this matter. Targeted delivery of NO provides a means for achieving site-specific smooth muscle relaxation, or other NO-mediated effects. In addition, delivery may be for the purpose of nitrosylation of various molecules present in the body. For example, S-nitroso-proteins would deliver NO, and thus nitrosylate hemoglobin or myoglobin in order to increase oxygen binding.

A significant advantage of S-nitroso-proteins is that they deliver NO in its most biologically relevant, and non-toxic form. This is critical, because the pharmacological efficacy of NO depends upon the form in which it is delivered. This is particularly true in airways, where high levels of $O_2$ and $O_2$ reactive species predispose to rapid inactivation of the NO moiety. As demonstrated by the inventors, S-nitroso-proteins deliver NO as the charged species, nitrosonium ($NO^+$) or nitroxyl ($NO^-$), and not the uncharged NO radical (NO.). This is important because the charged species behave in a very different manner from NO. with respect to chemical reactivity.

In contrast to NO., nitrosonium and nitroxyl do not react with $O_2$ or $O_2$ species, and are also resistant to decomposition in the presence of redox metals. Consequently, administration of NO equivalents does not result in the generation of toxic by-products or the elimination of the active NO moiety. By delivering nitrosonium or nitroxyl, S-nitroso-proteins provide a means for achieving the smooth muscle relaxant and anti-platelet effects of NO, and at the same time, alleviate significant adverse effects previously associated with NO therapy.

Another embodiment of the invention relates to the administration of S-nitroso-albumin as a therapeutic agent to promote platelet inhibition, or to cause relaxation of airway smooth muscle. The inventors have demonstrated that S-nitroso-BSA exerts a platelet inhibitory effect, and also promotes long-acting vasodilatory effect, which can be distinguished from that of NO or the low molecular weight thiols.

The inventors have also demonstrated that S-nitroso-BSA relaxes human airway smooth muscle. As discussed above, by delivering NO in the form of charged NO equivalents, such as nitrosonium, S-nitroso-proteins cause airway relaxation, and also eliminate the adverse effects which occur with administration of other NO species. Thus, S-nitroso-albumin may be administered for the treatment or prevention of respiratory disorders including all subsets of obstructive lung disease, such as emphysema, asthma, bronchitis, fibrosis, excessive mucous secretion and lung disorders resulting from post surgical complications. In addition these compounds may be used as antioxidants, and thus, in the treatment of diseases such as acute respiratory distress syndrome (ARDS).

Another embodiment of the invention relates to a method for nitrosylation of those proteins which lack free thiols. The method involves thiolating the protein by chemical means, such as homocysteine thiolactone (Kendall, B B A 257:83 (1972)), followed by nitrosylation in the same manner as the compounds discussed above. Recombinant DNA methods may also be used to add or substitute cysteine residues on a protein.

Another embodiment of the invention relates to a method for nitrosylation of those proteins in which the thiol is blocked by a methyl group. The method involves selective de-methylation of the protein by chemical means, such as reacting with methyl transferase, followed by nitrosylation in the same manner as the compounds discussed above.

Another embodiment of the invention involves the use of S-nitroso-protein compounds to relax non-vascular smooth muscle. Types of smooth muscle include, but are not limited to, bronchial, tracheal, uterine, fallopian tube, bladder, urethral, urethral, corpus cavemosal, esophageal, duodenal, ileum, colon, Sphincter of Oddi, pancreatic, or common bile duct.

An additional embodiment of the invention involves the in vivo nitrosylation of protein thiols, by administration of a nitrosylating agent as a pharmaceutical composition. In vivo nitrosylation provides a means for achieving any of the physiological effects discussed above, or for regulation of additional protein functions.

In addition to thiol groups, proteins and amino acids possess other sites which can be nitrosylated. For example, such sites may include, but are not limited to, oxygen, nitrogen, and carbon. Thus, an additional embodiment of the invention relates to the nitrosylation of additional sites, such as oxygen, nitrogen, and carbon which are present on proteins and amino acids, as a means for achieving any of the physiological effects discussed above, or for regulation of additional protein or amino acid functions. The inventors have shown that aromatic amino acids, such as tyrosine, phenylalanine and tryptophan can be nitrosylated at the hydroxyl, and amino groups, as well as on the aromatic ring, upon exposure to nitrosylating agents such as $NaNO_2$, NOCl, $N_2O_3$, $N_2O_4$ and $NO^+$. Other amino acids, such as serine and threonine may also be nitrosylated in the same manner.

The ability to bind NO to a variety of different sites on an amino acid or protein provides a greater concentration of NO, and thus may enhance regulation of protein function, as well as other NO-mediated effects such as smooth muscle relaxation and platelet inhibition. Thus, another embodiment of the invention relates to the use of amino acids and proteins which contain numerous NO molecules, to regulate protein or amino acid function and to effect smooth muscle relaxation and platelet inhibition. Additional therapeutic uses of these compounds include the treatment or prevention of such disorders as heart failure, myocardial infarction, shock, renal failure, hepatorenal syndrome, post-coronary bypass, gastrointestinal disease, vasospasm of any organ bed, stroke or other neurological disease, and cancer.

Another embodiment of the invention relates to a method for using these nitrosylated proteins and amino acids as a means for providing targeted delivery of NO to specific and intended bodily sites. These compounds have the capacity to deliver charged NO equivalents. For example, alkyl nitrites having the formula X—CONO and containing a beta-election withdrawing group would be able to deliver these charged NO equivalents.

The hydroxyl group of tyrosine also plays a central role in a variety of cell regulatory functions. For example, phosphorylation of tyrosine is a critical cell regulatory event. In addition, serine residues also provide phosphorylation sites. Thus, a particular aspect of this embodiment relates to the nitrosylation of amino acids such as tyrosine and serine, to regulate cellular process such as, but not limited to, phosphorylation.

Another embodiment of the invention relates to the use of O-nitrosylation of tyrosine residues on bovine serum albumin as a method for achieving smooth muscle relaxation and platelet inhibition.

Another embodiment of the invention relates to the nitrosylation of t-PA at additional sites, such as oxygen. For example, O-nitrosylation of t-PA, in addition to conferring vasodilatory and platelet inhibitory properties, alters the pharmokinetics of t-PA in such a way as to make it unavailable as a substrate for its natural inhibitor, PA-I.

Another embodiment of the invention relates to the administration of a pharmaceutical composition comprised of any S-nitroso-protein, to inhibit platelet function, cause vasodilation, relax smooth muscle, deliver nitric oxide to specific targeted bodily sites, or for the treatment or prevention of cardiovascular or respiratory disorders.

An additional application of the present invention relates to the nitrosylation of additional compounds such as peptides, neurotransmitters, pharmacologic agents and other chemical compounds, as a therapeutic modality. For example, nitrosylation of dopamine, a neurotransmitter improves the cardiac profile of the drug, by enhancing afterload reduction and scavenging free radicals, while simultaneously inhibiting platelets and preserving renal blood flow. Nitrosylation of epinephrine and related sympathomimetic drugs alters the half-life of the drug and affects its .beta.-agonist selectivity.

The nitrosylated proteins and amino acids of the present invention, or the nitrosylating agents may be administered by any means that effect thrombolysis, vasodilation, platelet inhibition, relaxation of non-vascular smooth muscle, other modification of protein functions or treatment or prevention of cardiovascular disorders, or any other disorder resulting from the particular activity of a protein or amino acid. For example, administration may be by intravenous, intraarterial, intramuscular, subcutaneous, intraperitoneal, rectal, oral, transdermal or buccal routes.

According to the present invention, a "therapeutically effective amount" of therapeutic composition is one which is sufficient to achieve a desired biological effect. Generally, the dosage needed to provide an effective amount of the composition, in which can be adjusted by one of ordinary skill in the art, will vary, depending on the age, health, condition, sex, weight, and extent of disease, of the recipient. In addition, the dosage may also depend upon the frequency of treatment, and the nature of the effect desired.

Composition within the scope of this invention include all compositions wherein the S-nitroso-protein or the nitrosylating agent is contained in an amount effective to achieve its intended purpose. While individuals needs vary, determination of optimal ranges of effective amounts of each component is within the skill of the art. Typical dosage forms contain 1 to 100 mmol/kg of the S-nitroso-protein. The dosage range for the nitrosylating agent would depend upon the particular agent utilized, and would be able to be determined by one of the skill in the art.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain preferably, about 0.01 to 5 percent, preferably from about 0.1 to 0.5 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tables or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, cross-linked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Having now generally described the invention, the same will be more readily understood through reference to the following examples which are provided by way of illustration, and are not intended to be limiting of the present invention.

EXAMPLES

Example 1

Synthesis of S-Nitroso-t-PA

A. Nitrosylation of t-PA
1. Materials t-PA was kindly provided by Genentech, Inc. San Francisco, Calif. Reactivated purified plasminogen activator inhibitor-1 (PAI-1) and a panel of six murine anti-t-PA monoclonal antibodies were kindly provided by Dr. Douglas E. Vaughan. Horse-Radish Peroxidase linked-sheep antimurine antibodies were purchased from Amersham Corp., Arlington, Ill. Sodium nitrite was purchased from Fisher Scientific, Fairlawn, N.J. H-D-isoleucyl-L-prolyl-L-arginyl-p-nitroanilide (S2288) and H-D-valyl-L-leucyl-L-lysyl-p-nitroanilide (S2251) were purchased from Kabi Vitrum, Stockholm, Sweden. Human fibrinogen purified of plasminogen and von Willebrand factor, was obtained from Enzyme Research Laboratories, South Bend, Ind. Epinephrine, ADP and iodoacetamide were purchased from Sigma Chemical Co., St. Louis, Mo. Bovine thrombin was obtained from ICN, ImmunoBiologicals (Lisle, Ill.) Radioimmunoassay kits for the determination of cGMP were purchased from New England Nuclear, Boston, Mass.

2. Plasminogen Preparation

Glu-plasminogen was purified from fresh frozen plasma thawed at 37° C. using a modification of the method of Deutsch and Mertz (Deutsch et al., Science 170:1095–1096 (1970), herein incorporated by reference). Plasma was passed over a lysine-Sepharose column and the column washed with 0.3 M sodium phosphate, pH 7.4, 3 mM EDTA. Plasminogen was eluted from the column with 0.2 M epsilon-aminocaproic acid, 3 mM EDTA, pH 7.4 Contaminant plasmin was removed by passing the eluted column over benzamidine sepharose 2B. The plasminogen obtained was subsequently dialyzed before use against 10 mM sodium phosphate, pH 7.4, 0.15 M NaCl.

3. Thiol Derivatization

The free thiol of t-PA was carboxyamidated by exposure of the enzyme to a 10-fold excess of iodoacetamide in the dark for one hour at 37° C. in 10 mM Tris, pH 7.4, 0.15 M NaCl (TBS). t-PA was then dialyzed extensively against 10 mM HCl in order to remove excess iodoacetamide.

4. Microcarrier Endothelial Cell Culture

Endothelial cells were isolated from bovine aorta by established techniques (Schwartz, S. M. In Vitro 14:966–980 (1978), herein incorporated by reference) and cultured on a microcarrier system of negatively charged spherical plastic beads (Biosilon), according to the method of Davies and colleagues (Davies et al., J. Cell Biol. 101: 871–879 (1985), herein incorporated by reference).

5. Nitrosylation t-PA was first dialyzed against a large excess of 10 mM HCl for 24 hours to remove excess L-arginine used to solubilize the protein. t-PA was then exposed to $NO_x$ generated from equimolar $NaNO_2$ in 0.5 N HCl (acidified $NaNO_2$) or in control experiments, to 0.5 N HCl alone, for 30 minutes at 37° C. Solutions were titrated to pH 7.4 with equal volumes of 1.0 N NaOH and Tris Buffered Saline (TBS), pH 7.4, 0.05 M L-arginine. Dilutions were then made as necessary in TBS.

For comparative purposes, and to illustrate the potential biological relevance of S—NO-t-PA, this-compound was synthesized with authentic EDRF in selected experiments. In this method, t-PA was incubated with bovine aortic endothelial cells stimulated by exposure to high shear forces to secrete EDRF, as we have previously described (Stamler et al., Cir. Res. 65:789 (1989), herein incorporated by reference). Owing to the stability of the S—NO bond in S—NO-t-PA under physiologic conditions ($t_{1/2}$>24 hours in TBS, pH 7.4, 20° C.), samples were stored at pH 7.4 on ice throughout the course of the experiments.

S—NO-t-PA has also been synthesized by exposure of t-PA to NO gas bubbled into buffered (TBS) solution of enzyme. This further illustrates the potential for s-nitrosylation, by exposure of proteins to a variety of oxides of nitrogen including NOCl, $N_2O_3$, $N_2O_4$ and other nitroso-equivalents.

B. Confirmation of S—NO bond
1. Methods

The formation of and stability of the S—NO bond were was confirmed by several published analytical methods.

In the first, NO displaced from S-nitrosothiol groups with $Hg^{2+}$ was assayed by diazotization of sulfanilamide and subsequent coupling with the chromophore N-(1-naphthyl-)ethylenediamine (Saville, B. Analyst 83:670–672 (1958), herein incorporated by reference). In the second, the characteristic absorption spectrum of S-nitrosothiols in the range of 320 nm-360 nm was detected (Stamler et al., Proc. Natl. Acad. Sci. USA in press (1991); Oac et al., Org. Prep. Proc. Int. 15(3):165–169 (1983)).

In the third, [$^{15}$N] NMR was used. Measurements of RS—NOs were made according to the method of Bonnett and colleagues (Bonnett et al., JCS Perkins Trans. 1:2261–2264 (1975), herein incorporated by reference). [$^{15}$N]NMR spectra were recorded with a Brucker 500 MHZ spectrometer, Billerica, Mass. Deuterium lock was effected with [D]$_2$O and the spectra referenced to an [$^{15}$N] natural abundance spectrum of a saturated solution of $NaNO_2$ at 587 ppm. Spectra were recorded at 50.68 MHZ and the nine transients of 16 k data points collected with a 30° pulse width and a 10-second relaxation delay. Data were multiplied by a 2-Hz exponential line broadening factor before Fourier transformation.

Confirmation of the above chemical evidence for protein S-nitrosothiol synthesis was obtained by UV, NMR and IR spectroscopy. Previous characterization of S-nitrosothiols, revealed that they passes UV absorption maxima at 320–360 nm, chemical shifts of approximately 750 ppm-relative to nitrite (Bonnett et al., JCS Perkins Trans. 1:2261–2264 (1975)), and IR stretches at approximately 1160 cm$^{-1}$ and 1170 cm. (Loscalzo et al., JPET 249:716–729 (1989)).

2. Results

Figure 1A:
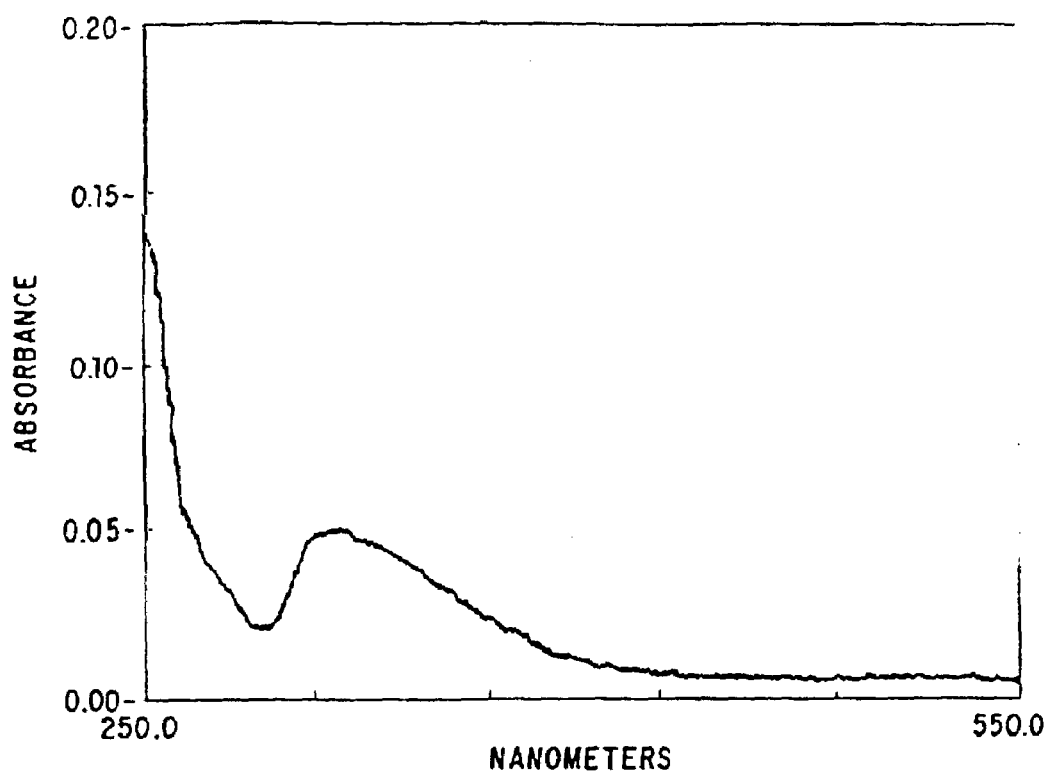
FIG. 1a: The ultraviolet absorption spectrum S—NO-t-PA (15 μM) relative to unmodified t-PA.
Figure 1B:
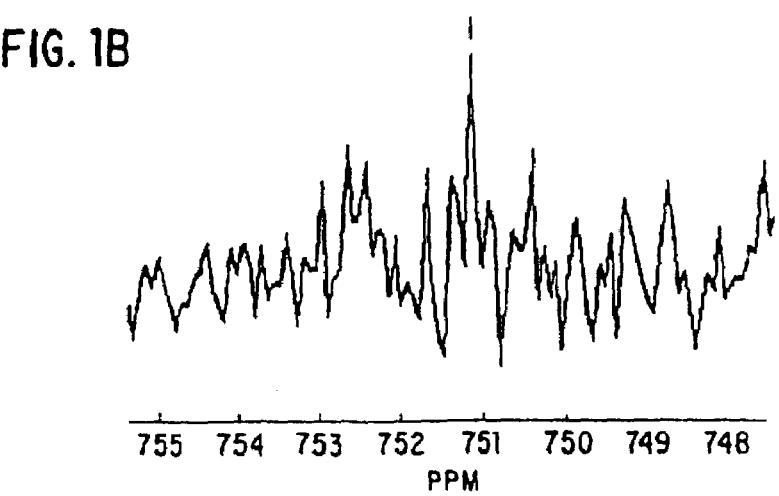
FIG. 1b: The chemical shift of S—[$^{15}$N]O-t-PA (35 μM) at 751 ppm relative to nitrite using [$^{15}$N]NMR.

In accordance with these observations, S—NO-t-PA exhibited an absorption maximum at 322 nm (FIG. 1a), and a chemical shift at 751 ppm (relative to nitrite) (FIG. 1b); elimination of the chemical shift was achieved by sample treatment with excess $HgCl_2$. In addition, the presence of two absorption bands at 1153 cm.sup.−1 and 1167 cm.sup.−1, is entirely consistent with the formation of an S-nitrosothiol bond (Myers et al., Nature 345:161–163 (1990); Oac et al., Org. Prep. Proc. Int. 15(3):165–169 (1983); Bonnett et al., JCS Perkins Trans. 1:2261–2264 (1975). The quantification of NO (Protein-NO+free $NO_x$) in the Saville reaction, and the NMR results demonstrating a single chemical shift, reveal that all NO bound to the protein exists in the form of an S-nitrosothiol.

Figure 2:
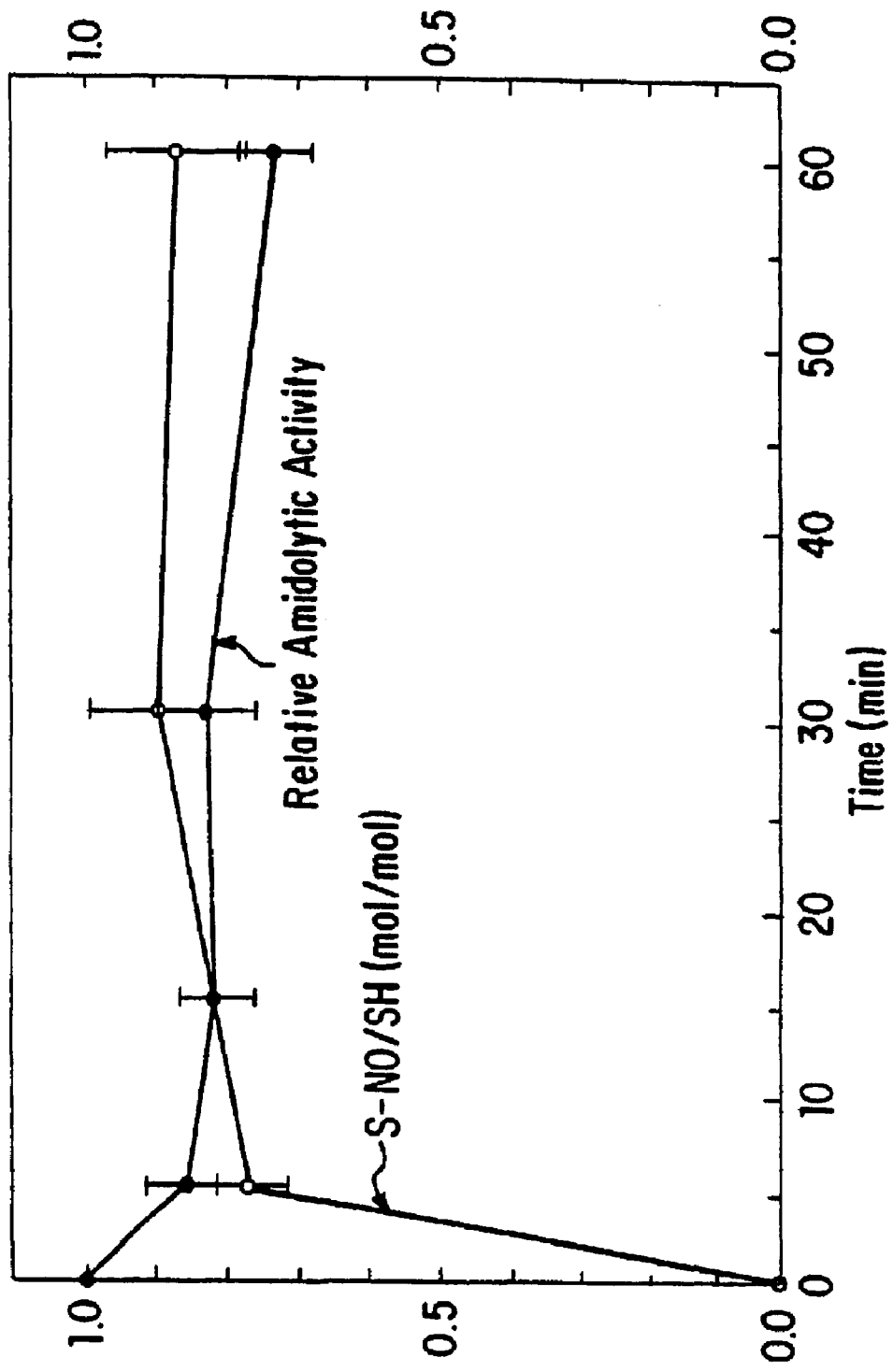
FIG. 2. Determination of S—NO bond formation in the synthesis of S—NO-t-PA.

FIG. 2 illustrates the time-dependent formation of S—NO-t-PA. Aliquots of the solution containing $NaNO_2$ were removed sequentially for determination of —S—NO bond formation (Schwartz, S. M. In Vitro 14:966–980 (1978)). Results are expressed as mean ±S.D. (n=3). By 30 minutes of exposure to acidified $NaNO_2$, S-nitrosylation is essentially complete; the stoichiometry of —S—NO/t-PA (mol/mol) is 0.0±0.1 (n=3) at the completion of the reaction as determined by the method of Saville (Saville, B. Analyst 83:670–672 (1958)). Carboxyamidation of t-PA's free thiol with iodoacetamide completely prevents S-nitrosothiol formation as determined by this chemical method (Saville, B. Analyst 83:670–672 (1958)).

FIG. 2 also illustrates the effect of acid treatment on the amidolytic activity of t-PA. At different intervals, aliquots of the enzyme exposed to 0.5 N HCl alone were neutralized, and amidolytic activity was assayed using the chromogenic substrate S2288. Results are expressed as mean ±S.D. (N=3), relative to t-PA not treated with 0.5 N HCl. At 30 minutes, the duration of exposure subsequently used for S-nitrosothiol synthesis, the enzymatic activity of t-PA is largely preserved. Quantification of S—NO-t-PA synthesis with authentic EDRF was similarly determined by the method of Saville (Saville, B. Analyst 83:670–672 (1958)).

Example 2

Synthesis of S-Nitroso-BSA

A. Nitrosylation

In the first method, nitrosylation of BSA was accomplished by incubating BSA (200 mg/ml with NO generated from equimolar $NaNO_2$ in 0.5N HCl (acidified $NaNO_2$) for thirty minutes at room temperature. Solutions were titrated to pH 7.4 with equal volumes of 1.0 N NaOH and Tris Buffered Saline (TBS), pH 7.4 0.05 M L-arginine. Dilutions were then made as necessary in TBS.

In the second method, nitrosylation was achieved in helium-deoxygenated solutions of 0.1 M sodium phosphate (pH 7.4) by exposing the protein solution in dialysis tubing to authentic NO gas bubbled into the dialysate for fifteen minutes. The proteins were then dialyzed against a large excess of 0.01 M phosphate buffer at pH 7.4 to remove excess oxides of nitrogen.

In the third method, proteins were incubated with bovine aortic endothelial cells stimulated by exposure to high shear forces to secrete EDRF, as in Example 1(A). As a corollary of this method, proteins were also incubated directly with NO synthase purified from bovine cerebellum (Bredt et al., Proc. Natl. Acad. Sci. USA 87:682 (1990), herein incorporated by reference) in the presence of the substrate L-arginine and cofactors required for enzyme activity ($Ca^{++}$, calmodulin, and NADPH).

B. Confirmation of S-Nitroso-Protein Formation

The formation and stability of the S-nitroso-protein was confirmed by several published analytical methods. NO displaced from S-nitrosothiol groups with $Hg^{2+}$ was assayed by diazotization of sulfanilamide and subsequent coupling with the chromophore N-(1-naphthyl-ethylenediamine (Mellion et al., Mol. Pharmacol. 23:653 (1983); Saville, B. analyst 83:670 (1958)). The stoichiometries of S—NO-BSA determined by these chemical methods is shown in Table 1.

Confirmatory evidence for S-nitrosothiol bond formation in proteins was obtained by spectrophotometry; S-nitrosothiols possess dual absorption maxima at 320–360 nm and at approximately 550 nm (Oac et al., Organic Prep. and Proc. Int. 15:165 (1983); Ignarro et al., J. Pharmacol. Exp. Ther. 218:739 (1981); Mellion et al., Mol. Pharmacol. 23:653 (1983); Loscalzo, J., Clin. Invest. 76:966 (1985)).

Figure 3:
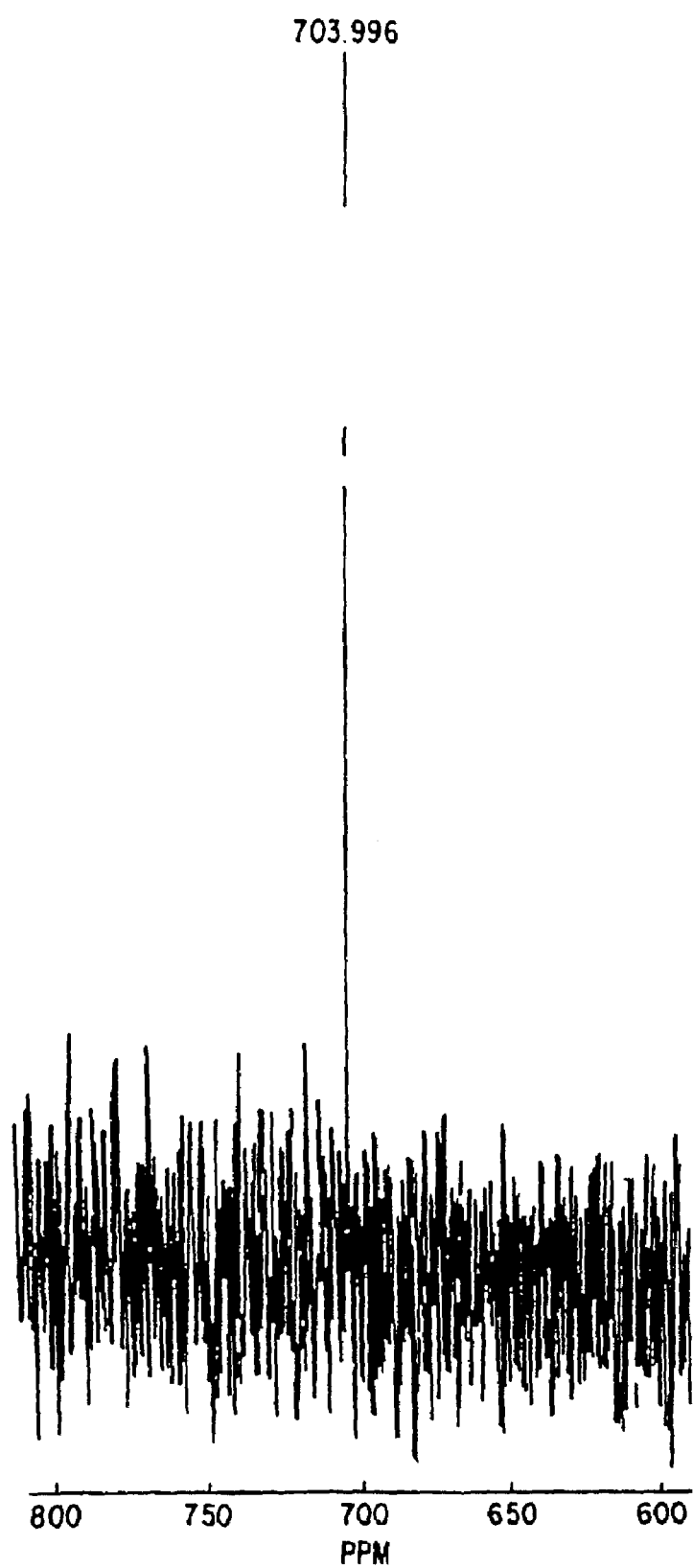
FIG. 3. [$^{15}$N]-NMR Spectrum of [$^{15}$N]-labeled S-nitroso-BSA.

As one additional, more specific measure of protein S-nitrosylation, [$^{15}$N]-NMR spectroscopy was used. BSA was S-nitrosylated with Na[$^{15}$N]$O_2$ and the [$^{15}$N]-NMR spectrum of the resulting species recorded in FIG. 3. FIG. 3 demonstrates the [$^{15}$N]-NMR Spectrum of [$^{15}$N]-labeled S-nitroso-BSA. The chemical shift for S-nitroso-BSA was 703.97, which falls into the same range as other S-nitrosothiols (e.g., S-nitroso-L-cysteine) prepared under similar conditions (Bonnett et al., J. Chem. Soc. Perkins Trans. 1:2261 (1975)). The spectrum was recorded at 50.68 MHZ and the nine transients of 16K data points were collected with a 30.degree. pulse width and a 2.5-sec relaxation delay. Data were multiplied by a 2-Hz exponential line broadening factor before Fourier transformation. The region of 590 to 810 ppm is displayed.

Example 3

Synthesis of S-Nitroso-Cathepsin B

Nitrosylation of cathepsin, and determination of S-nitrosothiol formation, was accomplished according to the methods described in Example 2. The stoichiometry of S-mitrosothiol/protein molecules for cathepsin is shown in Table 1.

Example 4

Synthesis of S-Nitroso-Lipoprotein

Synthesis was accomplished by nitrosylating purified low-density-lipoprotein (LDL) according to the methods described in Example 2. Confirmation of S-nitroso-protein formation was verified according to the methods of Example 2. The stoichiometry of S-nitrosothiol/protein molecules for LDL is shown in Table 1.

Example 5

Synthesis of S-Nitroso-Immunoglobulin

Synthesis was accomplished by nitrosylating purified gamma globulin (Sigma) according to the methods described in Example 2. Confirmation of S-nitroso-protein formation was verified according to the methods of Example 2. The stoichiometry of S-nitrosothiol/protein molecules for immunoglobulin is shown in Table 1.

TABLE I

S-Nitroso-Protein Synthesis

|  | -S-NO/protein (mol/mol) |
|---|---|
| Bovine Serum Albumin | 0.85 ± 0.04 |
| t-PA | 0.88 ± 0.06 |
| Cathepsin B | 0.90 ± 0.02 |
| Human Plasm | 0.87 ± 0.02 |
| Immunoglobulin | 0.35 ± 0.01 |
| Lipoprotein (LDL) | 1.80 |

Legend: The stoichiometries for the individual —S—NO/protein molar ratios are given in the table and represent the mean±SEM of 3 to 6 determinations.

Example 6

Demonstration of Thrombolytic, Anti-Platelet and Vasodilatory Effect of S—NO-t-PA A. Thrombolysis 1. Fibrinogen Binding The binding of t-PA and S——NO-t-PA to fibrinogen was measured using polystyrene microliter wells (flat-bottom, high binding 96-well EIA plates, cat. #3590, Costar, Cambridge, Mass.). Wells were coated with fibrinogen (0.08 ug/ul) and the remaining binding sites with 2% bovine serum albumin. Quantification of t-PA binding was determined using a Horse-Radish Peroxidase linked sheep anti-murine antibody in a colorimetric assay in the presence of O-phenylenediamine, 0.014% $H_2O_2$. Color change was measured spectrophotometrically with a Dynatech MR500 Card Reader (Dynatech, Chantilly, Va.) at 490 nm.

Binding of t-PA is reversible and specific, and saturates at 1500–3000 nM; at saturation, 18 ng of t-PA are bound per well (0105 moles t-PA per mole of fibrinogen) with an estimated $K_D$ in the range of 15–650 nM. Binding of t-PA and S—NO-t-PA was quantified by ELISA over the concentration range of 150–1500 nM using a mixture containing six murine monoclonal anti-t-PA antibodies.

a. Comparison of t-PA and S—NO-t-PA

Figure 4:
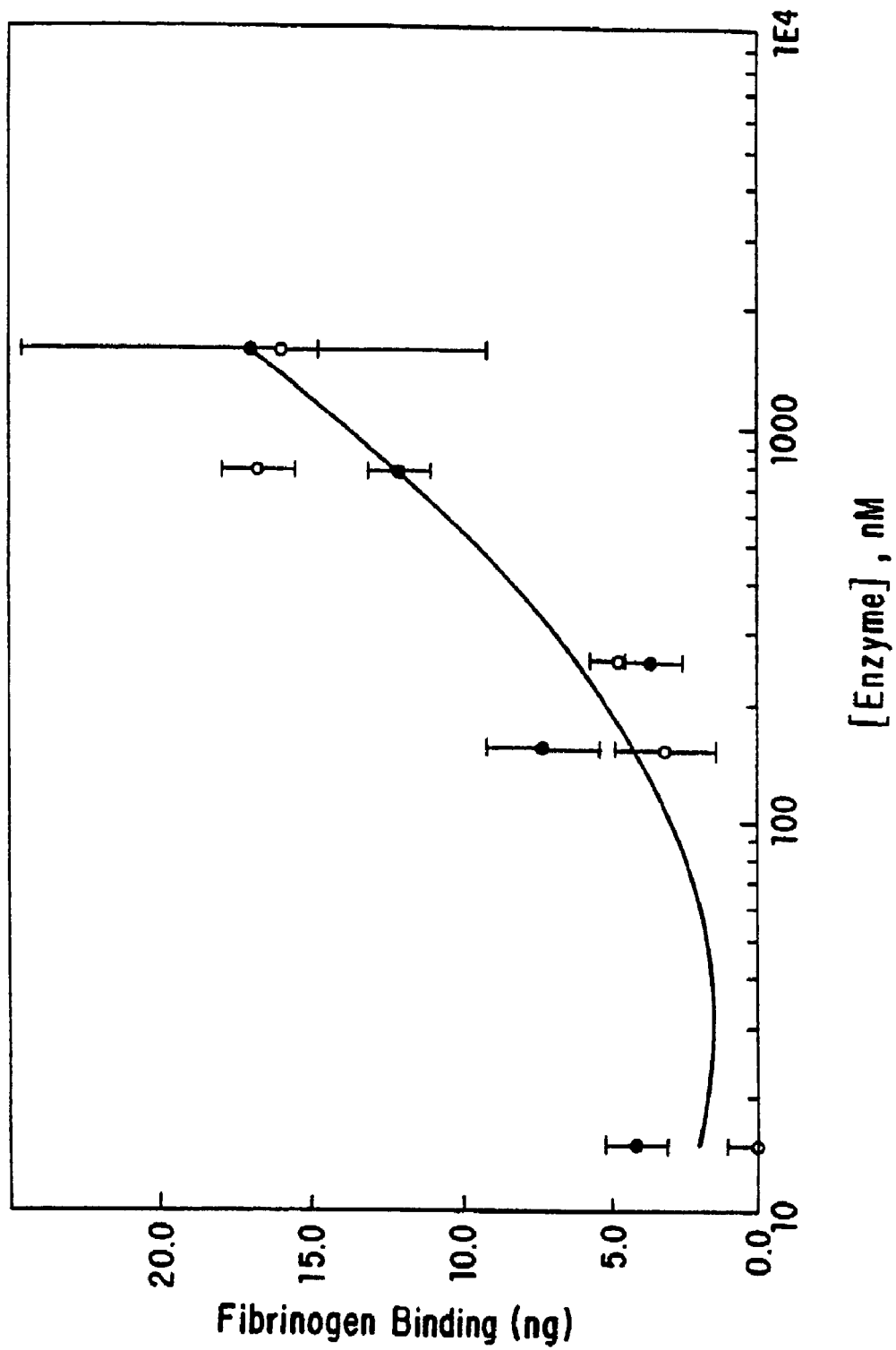
FIG. 4. Concentration-dependent binding of t-PA and S—NO-t-PA to fibrinogen-coated wells.

The binding of t-PA to fibrin(ogen) accounts for the relative "fibrin-specificity" of the enzyme as compared to certain other plasminogen activators (Loscalzo et al., New Engl. J. Med. 319(14):925–931 (1989); Vaughan et al., Trends Cardiovasc. Med. January/February;1050–1738 (1991)). The effect of S-nitrosylation on this functional property of the enzyme was therefore assessed. The binding isotherms for t-PA and its S-nitrosylated derivatives were not significantly different from each other by two-way ANOVA. Therefore, these data were subjected to a single best-curve-fit binding isotherm (FIG. 4). From a Scatchard analysis, the estimated apparent $D_D$ of S—NO-t-PA for surface-bound fibrinogen is 450 nm, which falls well within the reported range for t-PA (Ranby, M. Biochim. Biophysica Acta 704: 461–469 (1982)).

2. Measurement of Enzymatic Activity

The amidolytic activities of t-PA and its S-nitrosylated derivative were measured using the relatively specific chromogenic substrate, S2288. Substrate hydrolysis was measured spectrophotometrically at 405 nm with a Gilford Response UV/Vis Spectrophotometer (CIBA-Corning, Oberlin, Ohio). Activity was measured at 25° C. in TBS using substrate concentrations varying from 0.1–2.0 mM and t-PA at a concentration of 100 nM. Kinetic parameters were determined from initial rates by double reciprocal plot analysis. The assessment of inhibition of t-PA and S—NO-t-PA enzymatic activity by PAI-1 was made at an enzyme concentration of 10 nM and a molar ratio of t-PA to active PAI-1 of 1.0. The degree of inhibition was determined relative to the initial rates in the absence of the inhibitor.

In the coupled enzyme assay, t-PA and S—NO-t-PA activities were assayed using the native substrate S2251. In selected experiments, fibrinogen stimulation of enzymatic activity was assessed at a fibrinogen concentrations of 1 mg./ml. Substrate hydrolysis was measured spectrophotometrically with a Dynatech MR 5000 Card Reader (Dynatech, Chantilly, Va.) in TBS, pH 7.4, at 25° C. Initial reaction velocity was determined from the slope of the plot of absorbance (at 405 nm)/time vs. time (Randy, M. Biochim. Biophysica Acta 704:461–469 (1982)) using glu-plasminogen concentrations ranging from 0.1–10 μM at an S2251 concentrations of 0.8 mM. Kinetic parameters were determined from initial rates by double reciprocal plot analysis.

a. Comparison of t-PA and S—NO-t-PA

The amidolytic activity of t-PA and S——NO-t-PA were first compared against the chromogenic substrate S2288. From a double reciprocal plot analysis it is evident that the kinetic parameters ($K_m$ and $V_{max}$) and the catalytic efficiency ($K_{cm}/K_m$) of these molecules are essentially identical, as shown in FIG. 5a. The values of these kinetic constants are provided in Table 2.

The effect of S-nitrosylation on the ability of t-PA to activate its physiologic substrate, plasminogen, was assessed in the coupled enzyme assay in the presence and absence of fibrinogen. As seen in the Lineweaver-Burke plot (FIG. 5b) and from the derived kinetic parameters (Table 2), S—NO-t-PA has a $K_m$ for substrate similar to "wild type" t-PA. However, S—NO-t-PA has a slightly, but significantly, greater $V_{max}$ yielding a catalytic efficiency that is 23% greater than that of native t-PA.

3. Discussion

Both fibrin and fibrinogen increase the rate of activation of plasminogen by t-PA. The enhanced enzymatic activity of t-PA is the result of its ability to bind directly fibrin(ogen), which brings about a conformational change either in t-PA or plasminogen that promotes the interaction of t-PA with its substrate (Loscalzo et al., New Engl. J. Med. 319(14): 925–931 (1989)).

Figure 6:
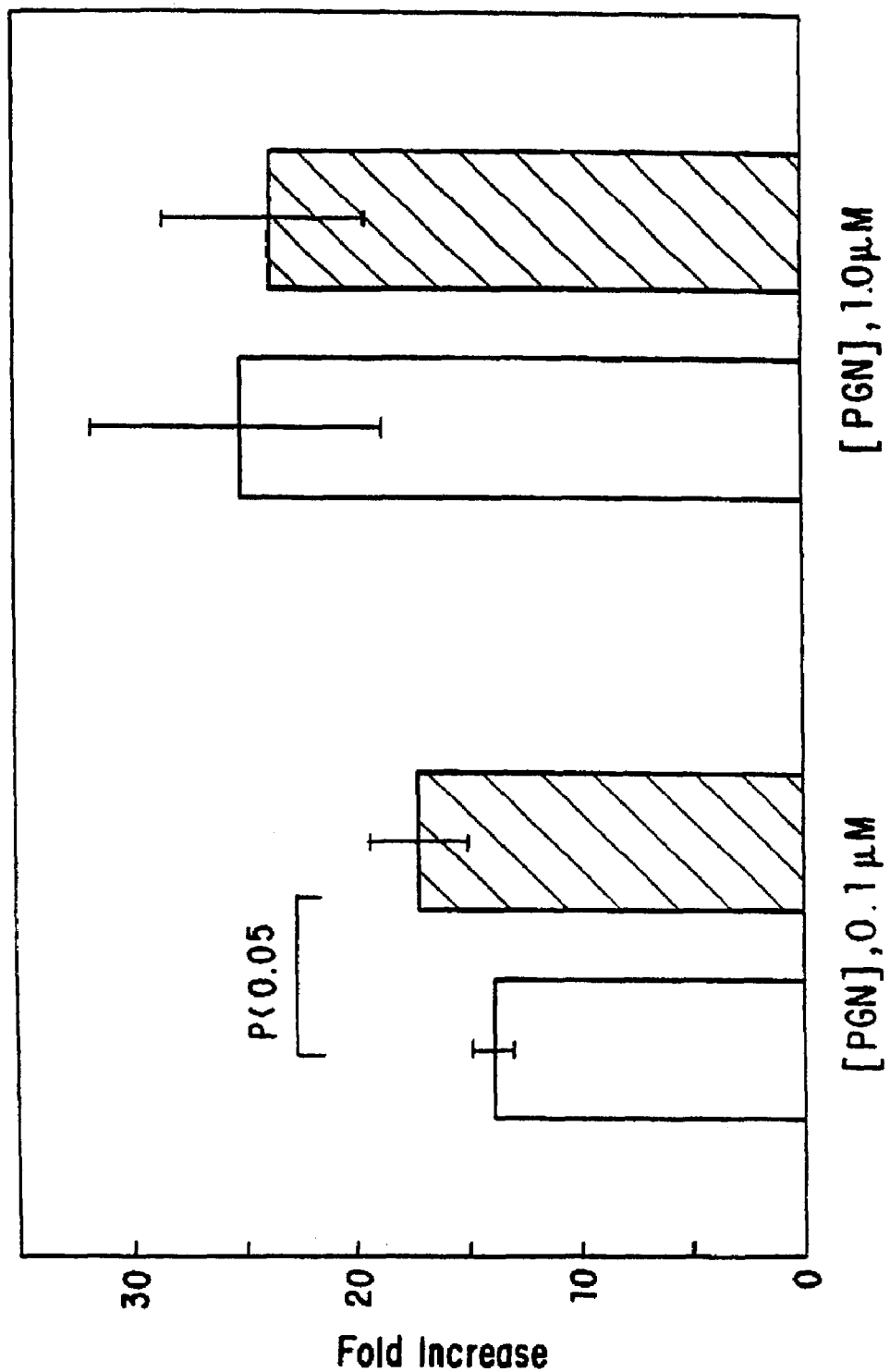
FIG. 6. Fibrinogen stimulation of enzymatic activity of t-PA (clear bars) and S—NO-t-PA (hatched bars), compared in the coupled enzyme assay at concentrations of 0.1 μM and 1.0 μM of plasminogen.

The consequences of S-nitrosylation on these important functional properties of t-PA were therefore studied in a comparative analysis with t-PA in the coupled enzyme assay. The results, summarized in FIG. 6, indicate that S—NO-t-PA binds to fibrinogen; that as a result of this binding its enzymatic activity is enhanced; and that in the presence of physiologic (1 μM) plasminogen concentrations, the degree of stimulation is equivalent to that of "wild type" t-PA. At lower plasminogen concentrations (0.1 μM), fibrinogen stimulation of S—NO-t-PA was 3.5-fold greater than t-PA (1

μM) (p<0.05). Absolute rates of plasminogen activation were again slightly greater for S0-NO-t-PA (vida supra).

t-PA is rapidly inhibited by its cognate plasma serpin, PA1–1 (Loscalzo et al., New Engl. J. Med. 319(14):925–931 (1989); Vaughan et al., Trends Cardiovasc. Med. January/February: 1050–1738 (1991)). By serving as a pseudo-substrate, PAI-1 reacts stoichiometrically with t-PA to form an inactive complex. PAI-1 was equally effective at inhibiting the hydrolytic activity of t-PA and S—NO-t-PA in the direct chromogenic assay with S2288 (n——3; PNS). Thus, S-nitrosylation of t-PA does not appear to alter its interaction with PAI-1.

B. Platelet Inhibition

1. Preparation of Platelets

Venous blood, anticoagulated with 1-mM trisodium citrate, was obtained from volunteers who had not consumed acetylsalicylic acid for at least ten days. Platelet-rich plasma (PRP) was prepared by centrifugation at 150 g for ten minutes at 25° C. Platelet counts were determined with a Coulter counter (model ZM; Coulter Electronics, Hialeah, Fla.).

2. Platelet Gel-Filtration and Aggregation

Platelets were gel-filtered on a 4.times. 10 cm column of Sepharose 2B in Tyrode's Hepes buffer as described previously (Hawiger et al., Nature 2831:195–198 (1980), herein incorporated by reference). Platelets were typically suspended at a concentration of 1.5.times.10.sup.8/ml and were used within 30 minutes of preparation. Platelet aggregation was monitored using a standard nephelometric technique (Born, et al., J. Physiol. 168:178–195 (1963), herein incorporated by reference), in which 0.3-ml aliquots of gel-filtered platelets were incubated at 37° C. and stirred at 1000 rpm in a PAP-4 aggregometer (Biodata, Hatboro, Pa.). Gel-filtered platelets were preincubated with t-PA or S—NO-t-PA for up to 45 minutes and aggregations induced with 5 μM ADP or 0.025 U/ml thrombin.

Aggregations were quantified by measuring the maximal rate or extent of light transmittance and expressed as a normalized value relative to control aggregations.

3. Cyclic Nucleotide Assays

The antiplatelet actions of S-nitrosothiols are mediated by cyclic GMP. Measurements of cGMP were performed by radioimmunoassay. Gel-filtered platelets were pre-incubated for 180 seconds with S—NO-t-PA (9 μM), and related controls. Reactions were terminated by the addition of 10% trichloracetic acid. Acetylation of samples with acetic anhydride was used to increase the sensitivity of the assay.

Figure 7:
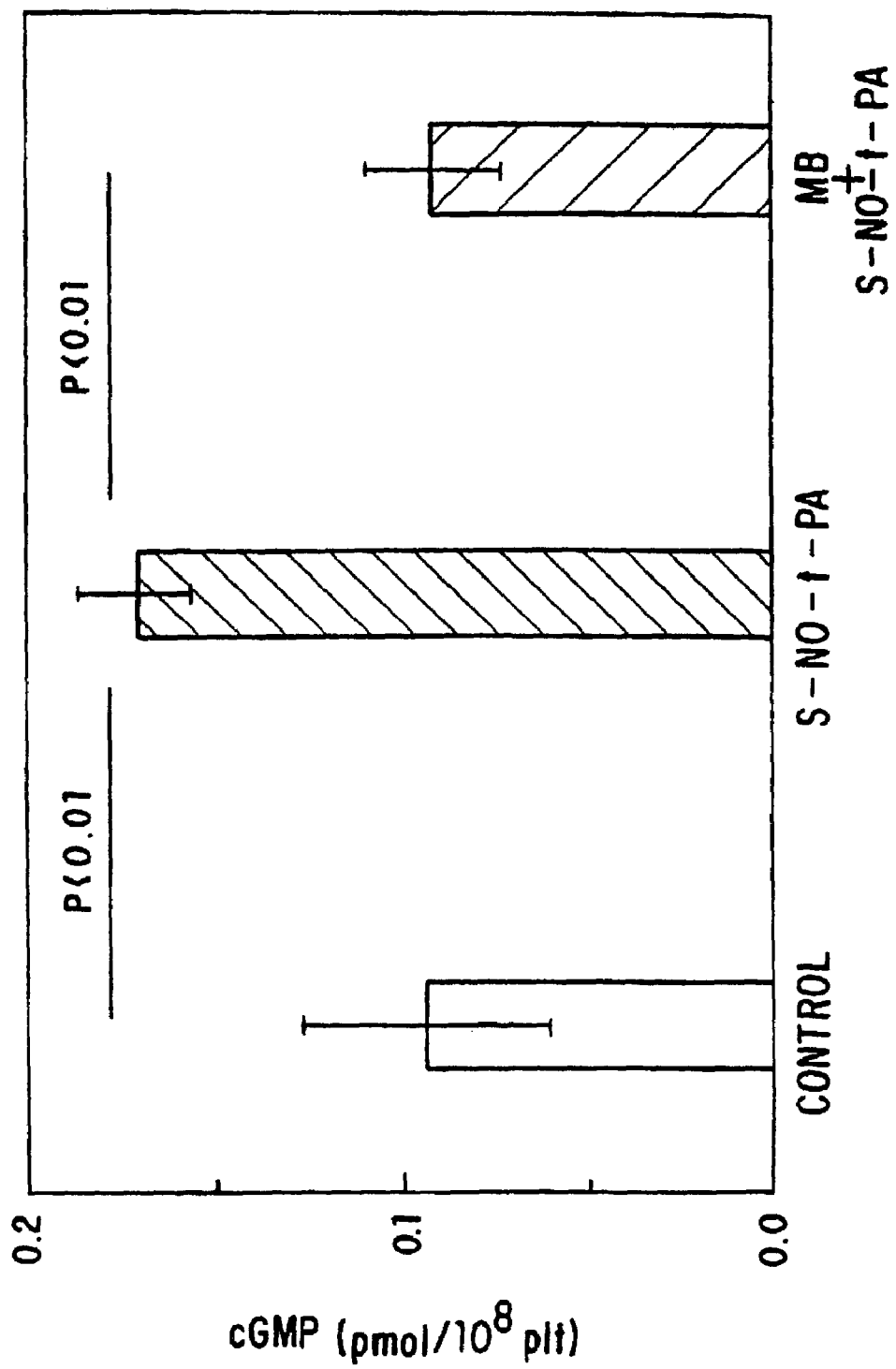
FIG. 7. Increases in intracellular platelet cyclic GMP, caused by S—NO-t-PA.

S—NO-t-PA incubated with platelets for 180 seconds, induced an 85% increase in intracellular cyclic GMP above basal levels in the presence of t-PA (p<0.01). The elevation in intracellular platelet cGMP induced by S—NO-t-PA was entirely prevented by preincubation of platelets with the guanylate cyclase inhibitor methylene blue (10 μM for ten minutes (n=3) (FIG. 7).

4. Discussion

The effects of S—NO-t-PA were studied in a gel-filtered platelet preparation. In these experiments, $NO_x$ generated for $NaNO_2$ had no significant effect on the extent of platelet aggregation (tracing not shown). Mean results for inhibition by S—NO-t-PA are presented in Table 4.

Figure 8A:
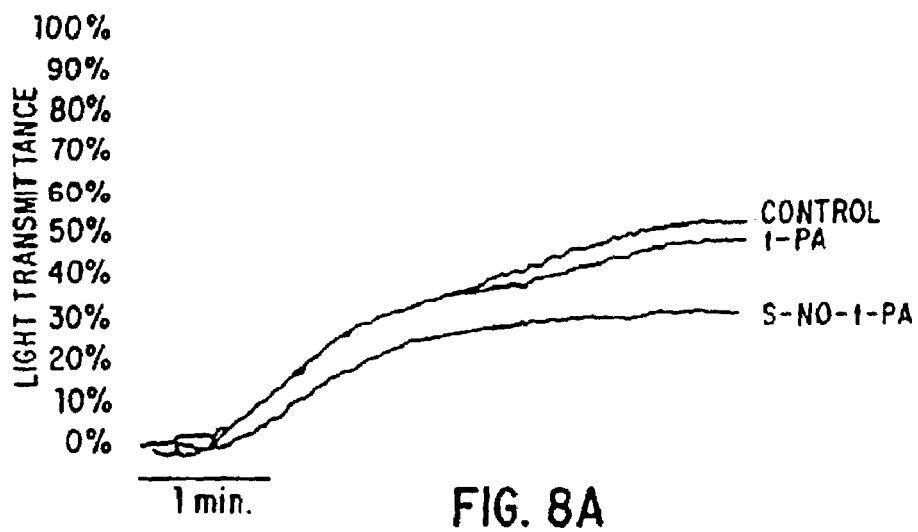
FIG. 8. Inhibition of platelet aggregation by S—NO-t-PA.
Figure 8B:
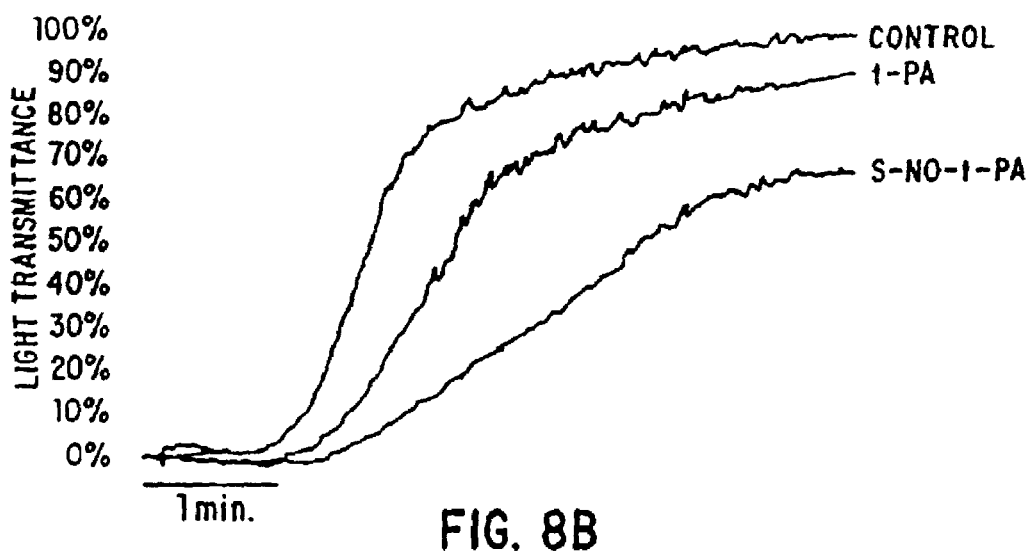
Figure 8C:
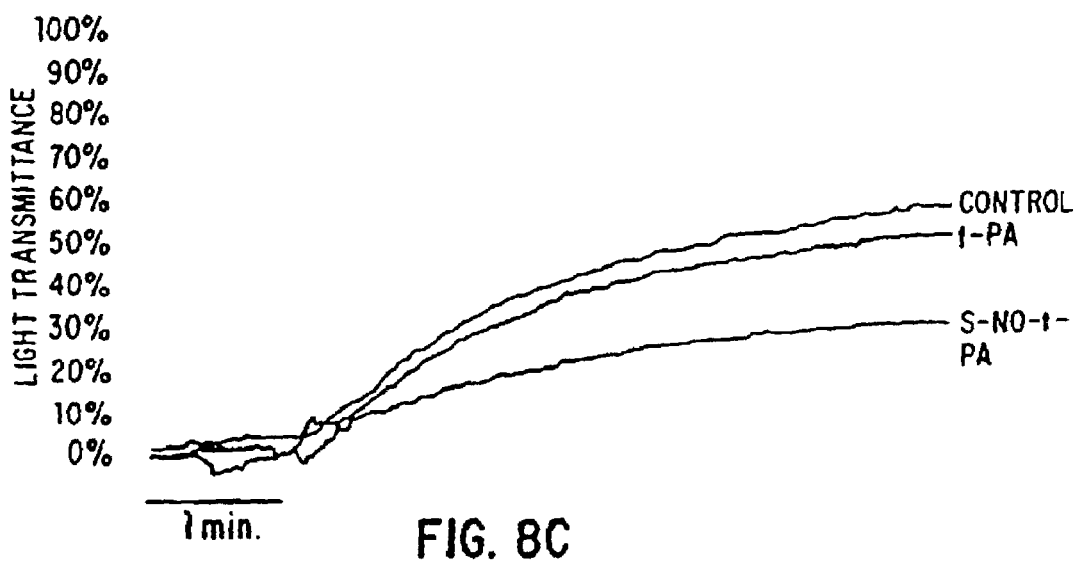

FIG. 8 illustrates platelet inhibition induced by S—NO-t-PA (333 nM) synthesized with EDRF. In these experiments, t-PA was exposed to endothelial cells stimulated to secrete EDRF for 15 minutes after which the formation for S—NO-t-PA was verified by method for Saville (Saville, B. Analyst 83:670–672 (1958)). S—NO-t-PA was then preincubated with platelets for ten minutes prior to induction of aggregation with 5 μM ADP. In the absence of t-PA, effluent from endothelial cells stimulated to secrete EDRF had no significant effect on platelet aggregation. S—NO-t-PA inhibited platelet aggregation to 5 μM ADP in a dose-dependent manner, with 50±16% (mean ±S.D.) inhibition in rate and extent of aggregation observed at 1.4 μM S—NO-t-PA (n=4; p<0.001 vs. control). Inhibition of platelet aggregation induced by ADP (5 μM) or thrombin (0.024 U/ml) was demonstrable at concentrations of S—NO-t-PA in the pharmacologic range of 15–150 nM, as shown in the illustrative tracings of FIGS. 8(a) and (b) and in Table 4. In further support of the potential biological relevance for RS—NOs, and the comparable bioactivity of S—NO-t-PA irrespective of its method of synthesis, inhibition of platelet aggregation by S—NO-t-PA (333 nM) synthesized with authentic EDRF is illustrated in FIG. 8(c).

C. Vasodilation

1. Preparation of Blood Vessels

New Zealand White female rabbits weighing 3–4 kg were anesthetized with 30 mg/kg IV sodium pentobarbital. Descending thoracic aortae were isolated and placed immediately in a cold physiologic salt solution (Kreb's) (mM): NaCl, 118; CKl, 4.7; $CaCl_2$, 2.5; $MgSO_4$, 1.2; $KH_2PO_4$, 1.2; $NaHCO_3$, 12.5; and D-glucose, 11.0. The vessels were cleaned of adherent connective tissue, and the endothelium removed by gentle rubbing with a cotton tipped applicator inserted into the lumen, after which the vessel was cut into 5 mm rings. The rings were mounted on stirrups and connected to transducers (model FT03C Grass Instruments, Quincy, Mass.) by which changes in isometric tension were recorded.

2. Bioassay

Samples were added to a standard bioassay in which vessel rings were suspended in glass chambers containing seven mil of oxygenated Kreb's buffer, in a standard bioassay (Cook et al., Am. J. Physiol. 28:H804 (1989), herein incorporated by reference). Sustained contractions, to 2 gm tension, were induced with 1 μM epinephrine, after which the effects of t-PA and S—NO-t-PA were tested. In certain experiments the guanylate cyclase inhibitor, methylene blue, was preincubated with vessel rings for 15 minutes prior to initiation of contractions.

3. Vascular Relaxations

Figure 9A:
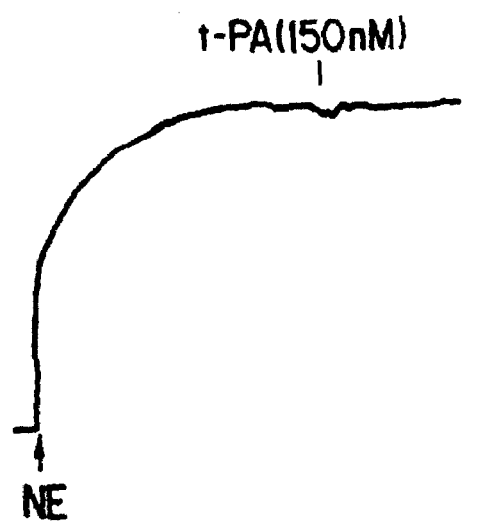
FIG. 9. Comparison of S—NO-t-PA induced vasorelaxation caused by (a) t-PA (150 nM), (b) S—NO-t-PA (150 nM), and (c) S—NO-t-PA (150 nM).
Figure 9B:
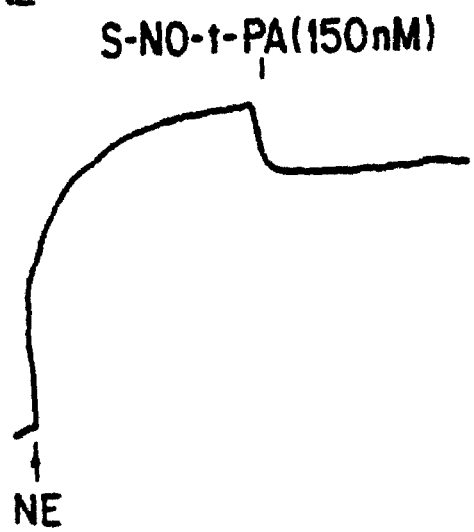
Figure 9C:
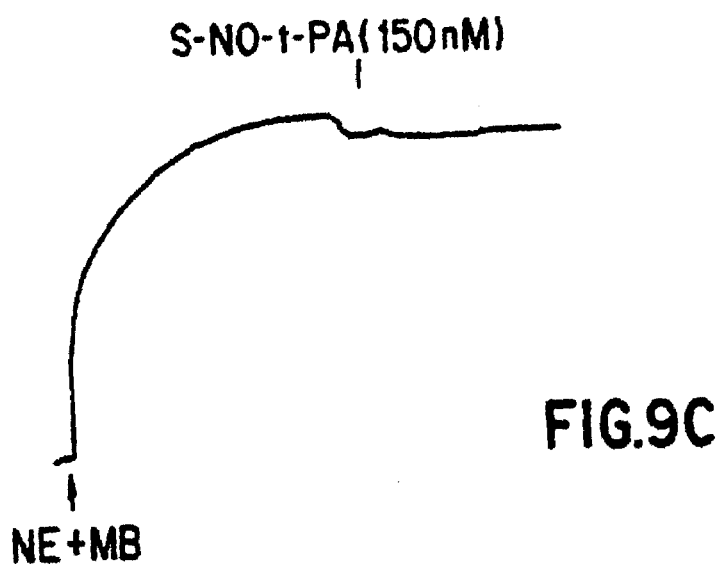

As shown in the illustrative tracings of FIG. 9, S—NO-t-PA, at pharmacologic concentrations, induces relaxations that are unmatched by equimolar amounts of the reactant protein-thiol or NO alone. Furthermore, consistent with the mechanism of other nitro(so)-vasodilators, relaxations were attenuated by the guanylate cyclase inhibitor, methylene blue. Table 3 depicts the effect of S—NO-t-PA on vessel relaxation for several such experiments.

TABLE 2

Kinetic Parameters of S2288 Hydrolysis and GLU-Plasminogen (S2251) Activation By t-PA and S-NO-t-PA

|  | $K_m$ (μM) | $k_{cat}$ (sec$^{-1}$) | $k_{cat}/K_m$ (sec$^{-1}$ - μM$^{-1}$) |
|---|---|---|---|
| S2288 | | | |
| t-PA | 280 | 0.52 | 0.0019 |
| S-NO-t-PA | 295 | 0.52 | 0.0019 |
| S2251 | | | |
| t-PA | 3.5 | 0.200 | 0.056 |
| S-NO-t-PA | 3.8 | 0.262 | 0.069 |

TABLE 3

Vessel Relaxation

| | | % Relaxation |
|---|---|---|
| t-PA | (150 nM) | 2.5 ± 4 |
| NO | (150 nM) | 1.0 ± 1.7 |
| S-NO-t-PA | (150 nM) | 20 ± 7* |

Mean results (±S.D.; n=4) of vessel relaxation induced by S—NO-T-PA, and the comparable relaxation induced by equivalent concentrations of NO (generated from acidified NaNO$_2$) a t-PA. * Relaxations to S—NO-t-PA were significantly greater than those induced by NaNO$_2$ or t-PA, as shown in this table for equal concentrations.

TABLE 4

Platelet Inhibition
% Normalized Extent Aggregation

| | | ADP (5 µM) | Thrombin (0.024 U/ml) |
|---|---|---|---|
| t-PA | (150 µM) | 1.06 × 0.24 | 0.90 ± 0.15 |
| S-NO-t-PA | (150 µM) | 0.77 × 0.28** | 0.73 ± 0.28* |

Mean results (±S.D.; n=13–17) of platelet inhibition mediated by S—NO-t-PA to both AD-induced platelet aggregation. NO generated from NaNO$_2$ (150 nM) had no significant effect on platelet inhibition in these experiments (0.98±0.11, n=5). *p<0.025 compared with t-PA; ** p <0.01 compared with t-PA.

Statistics

Determination of statistical significance was analyzed using a nonpaired t-test or two-way analysis of variance (ANOVA) followed by a Newman-Keul's comparison.

Example 7

Demonstration of Platelet Inhibitory and Vasodilatory Effect of S-Nitroso-BSA

A. Platelet Inhibition

The effect of S-nitroso-BSA on platelet aggregation was studied, using a gel-filtered platelet preparation, as previously described (Hawiger et al., Nature 2831:195 (1980)) and suspended at 150,000 platelets/ul in HEPES buffer, pH 7.35. S—NO-BSA was incubated with platelets for ten minutes at 37° C. in a PAP-4 aggregometer (BioData, Hatboro, Pa.), after which aggregations were induced with 5 µM ADP. Aggregations were quantified by measuring the extent of change of light transmittance and expressed as a normalized value relative to control aggregations.

In control experiments, neither NaNO$_2$ at concentrations up to 15 µM nor the effluent from cells stimulated to secrete EDRF in the absence of BSA had any significant effect on either vessel tone or platelet aggregation. All non-nitrosylated proteins studied had no significant effect on platelet aggregation at any concentration tested.

Dose-dependent inhibition of ADP-induced platelet aggregation was observed over the range of 150 nM to 15 µM S-nitroso-protein. A nitrosylated protein plasma fraction was even more potent, manifesting inhibition at estimated —S—NO concentrations of 150 pM. S-nitroso-proteins synthesized with acidified NaNO$_2$, with NO gas, or be exposure to bovine aortic endothelial cells stimulated to secrete EDRF were essentially equipotent, as shown for S-nitroso-BSA in FIG. 10. Furthermore, the platelet inhibitory effect of S-nitroso-BSA (1.4 µM) was confirmed both in platelet-rich plasma and in whole blood (using impedance aggregometry in this latter case) (Chong et al., Drug Met. and Disp. 18:61 (1990) herein incorporated by reference).

Figure 10:
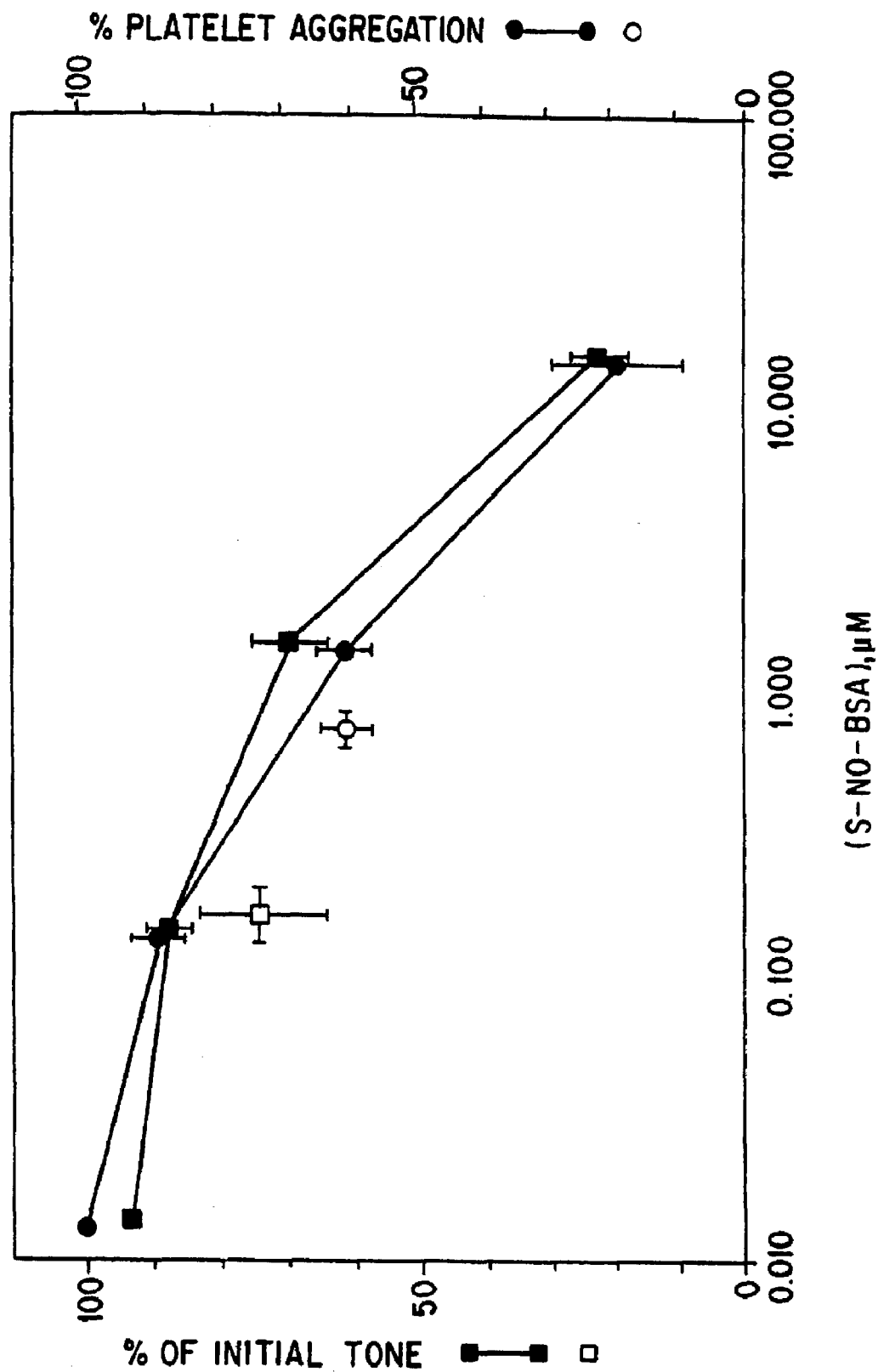
FIG. 10. Dose-dependent relaxation of vascular smooth muscle and inhibition of platelet aggregation caused by S-nitroso-BSA (S—NO-BSA).
Figure 11A:
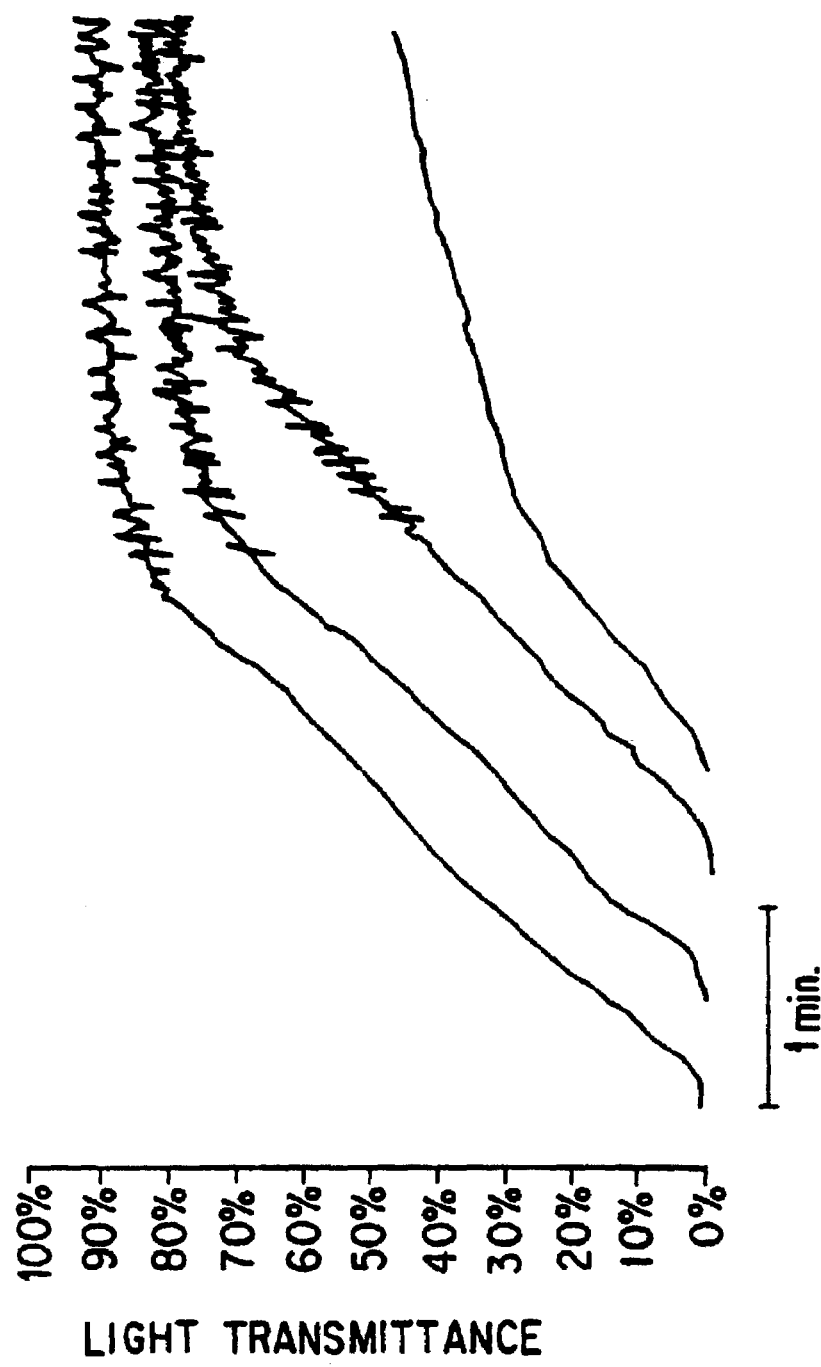

Representative mean data and illustrative aggregation tracings for S-nitroso-BSA are provided in FIGS. 10 and 11a, respectively. Carboxyamidation of protein thiols with iodoacetamide or pretreatment of platelets with the guanylate cyclase inhibitor methylene blue abolished the antiplatelet effects of S-nitroso-proteins (FIG. 11a). In addition, the half-life of the antiplatelet effects correlated with that for vascular smooth muscle relaxation.

B. Vasodilation

1. Methods

The vasodilatory actions of S-nitroso-BSA were examined in a standard bioassay containing endothelium-denuded rabbit aortic strips in Kreb's buffer, pH 7.5, at 37°, as described in Example 6.

2. Results

Dose-dependent relaxations were observed over the range of 15 nM to 15 µM S-nitroso-proteins, and representative mean data for S-nitroso-BSA are provided in FIG. 10. S-nitroso-proteins synthesized with acidified NaNO$_2$, with NO gas, or by exposure to bovine aortic endothelial cells stimulated to secrete EDRF were essentially equipotent; this is again exemplified for S-nitroso-BSA in FIG. 10. The relaxation response to S-nitroso-BSA proteins differed from that generally ascribed to EDRF, authentic NO, and the relatively labile low molecular weight biological S-nitrosothiols, all of which are characterized by rapid, transient relaxations. In marked contrast, S-nitroso-BSA induced a less rapid, but much more persistent, relaxation response (FIG. 11b), thus confirming that it acts as a long-acting vasodilator.

Furthermore, BSA incubated with NO synthase in the presence of cofactors required for enzyme activity (calmodulin, NADPH, Ca$^{++}$) showed an L-arginine-dependent ability to induce persistent vasorelaxation characteristic of S-nitroso-proteins.

The half-life of S-nitroso-BSA as determined in the bioassay corresponded with chemical measurements of half-life and is approximately twenty-four hours. This half-life is significantly longer than the half-lives of low molecular weight S-nitrosothiols and suggests that the temporal profile of the relaxation response for S-nitrosothiols correlates with the lability of the S—NO bond.

Blockade of protein thiols by carboxyamidation with iodoacetamide prevented S-nitrosothiol formation as determined chemically, and rendered the proteins exposed to NO or EDRF biologically inactive (FIG. 11b). Consonant with the mechanism of other nitro(so)-vasodilators (Ignarro, L. J. Circ. Res. 65:1 (1989)), relaxations were abolished by methylene blue, an inhibitor of guanylate cyclase (FIG. 11a). This mechanism was confirmed by showing that S-nitroso-BSA (18 µM) induces 3.5-fold increases (n=2) in cyclic GMP over basal levels relative to BSA alone in cultured RFL-6 lung fibroblasts containing a soluble guanylate cyclase exquisitely sensitive to NO (Forstermann et al., Mol. Pharmacol. 38:7 (1990)). Stimulation of guanylate cyclase by S-nitroso-BSA was attenuated by methylene blue.

FIG. 10 demonstrates the dose-dependent relaxation of vascular smooth muscle and inhibition of platelet aggregation with S-nitroso-BSA (S—NO-BSA). Dose-effect curves for vessel relaxation (■-■) and platelet inhibition (●-●)

were generated with S—NO-BSA synthesized with equimolar NO generated from acidified $NaNO_2$ as described in the text and then neutralized to pH 7.4. Data are presented as mean±SEM (n=6–18). The open symbols represent experiments, in the vessel (□) and platelet (○) bioassays, in which S—NO-BSA was synthesized by exposure of BSA to bovine aortic endothelial cells stimulated to secrete EDRF. These data are presented as mean±SEM (n=3–8), with the X-axis error bars indicating the variance in the concentration of S—NO-BSA generated from EDRF and the Y-axis error bars indicating the variance in the bioassay response.

In vessel experiments, relaxations to S—NO-BSA are expressed as-percent of tone induced by 1.0 µM norepinephrine.

Figure 12:
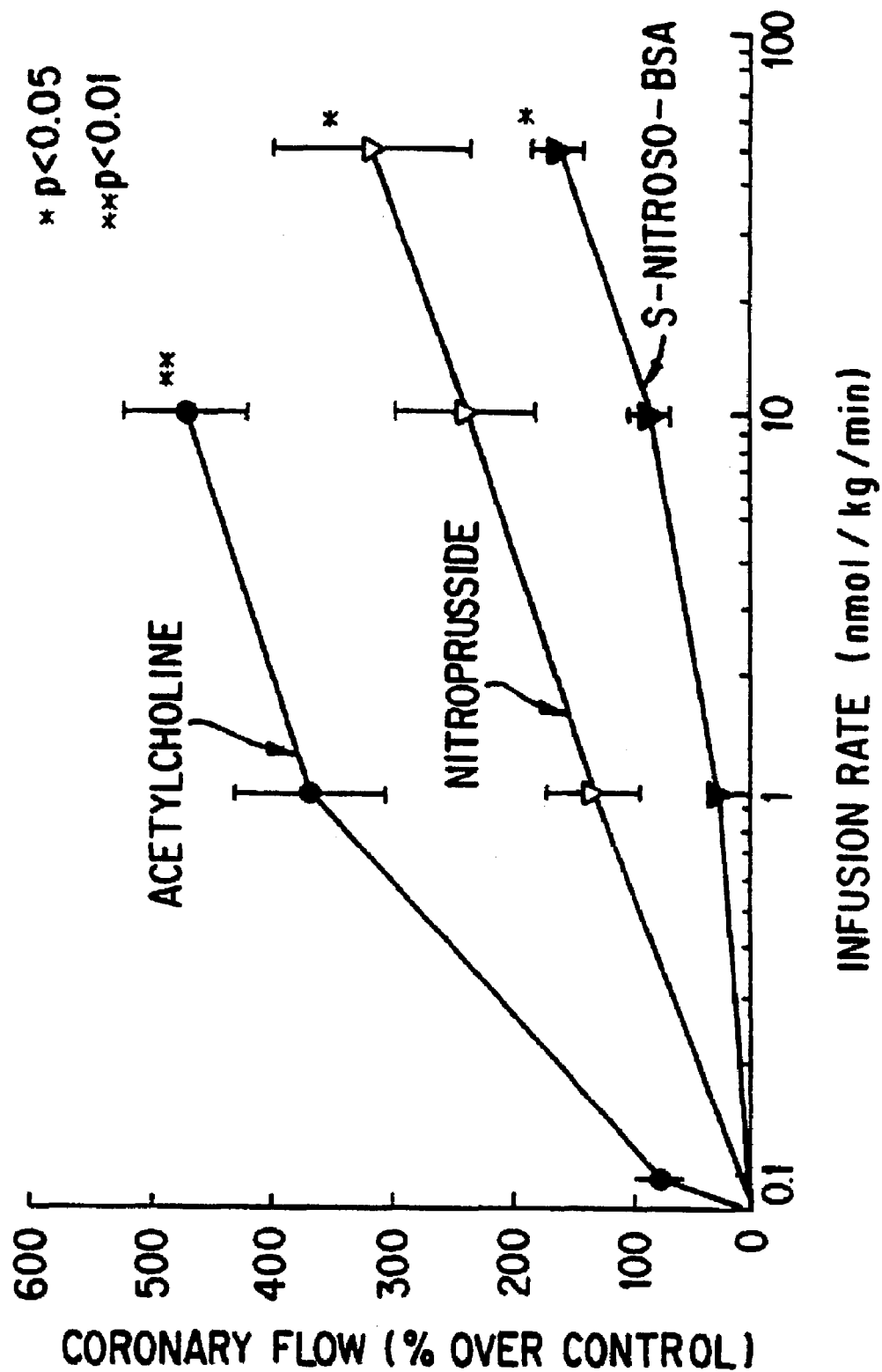
FIG. 12. Coronary blood flow in anesthetized dogs, following infusion of S-nitroso-BSA.
Figure 13:
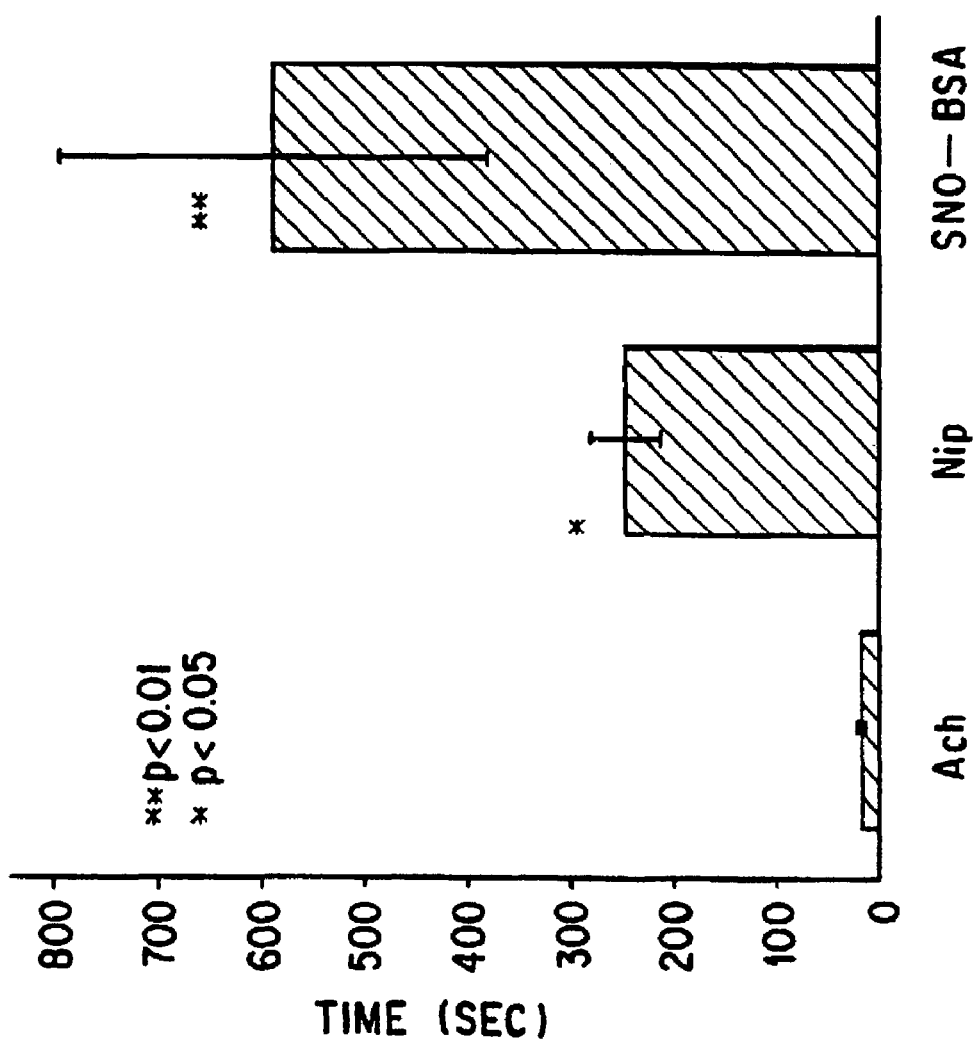
FIG. 13. Duration of increased coronary blood flow, following infusion of S-nitroso-BSA.
Figure 14:
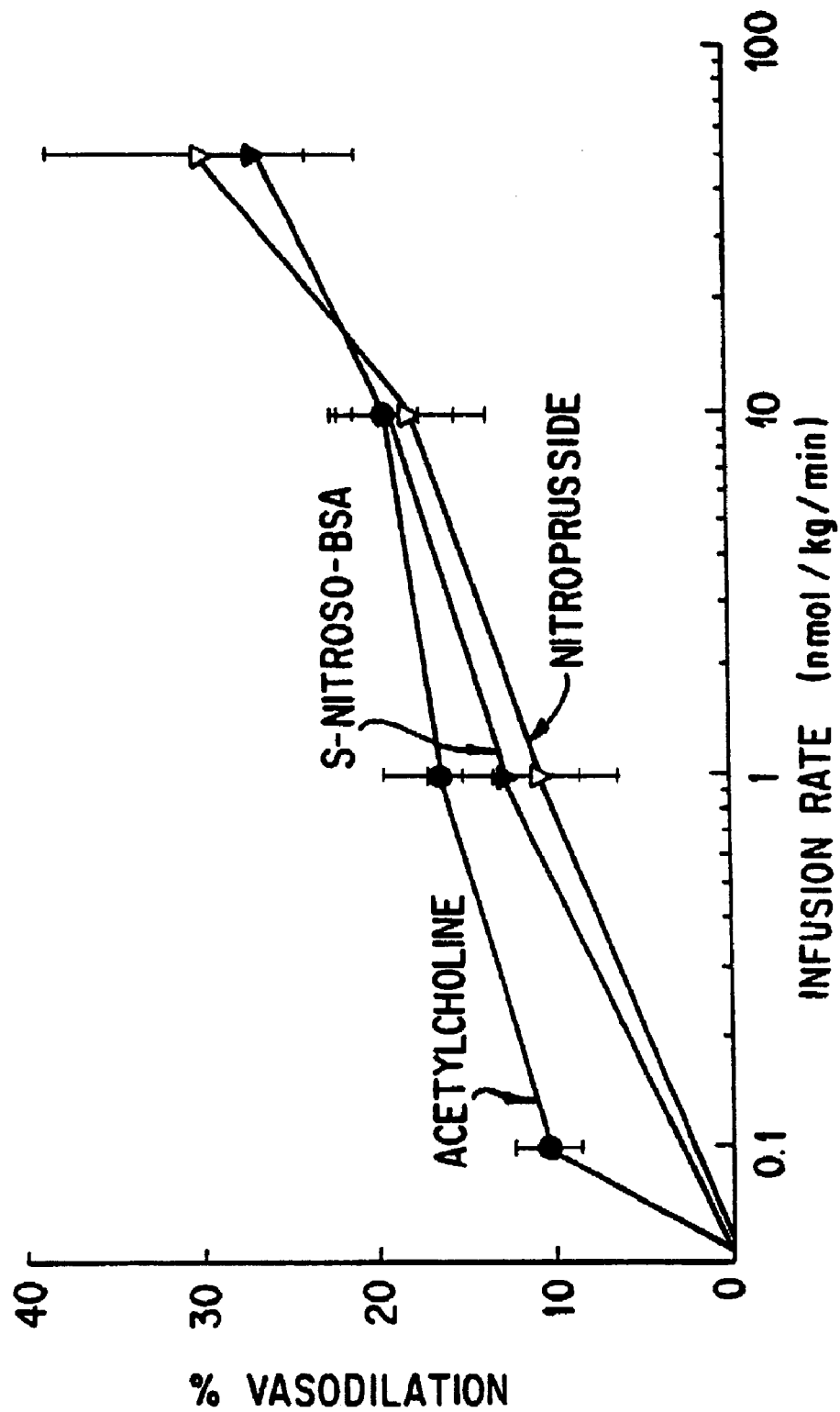
FIG. 14. Coronary vasodilation, following infusion of S-nitroso-BSA.

Infusion of S—NO-BSA into anesthetized dogs, according to standard methods known in the art, resulted in prolonged decreases in blood pressure, unmatched by low molecular weight S-nitrosothiols. In addition, this compound increased coronary flow, thus preserving myocardial blood flow. In a canine model of subtotal coronary artery occlusion, S—NO-BSA inhibited platelet-dependent cyclic thrombus formation and significantly prolonged bleeding times. These extremely potent, but reversible anti-platelet properties in vivo are unmatched by classic nitrates. As well, the improvement in coronary blood flow contrasts markedly with the clinically used nitroso-compound, nitroprusside, which has deleterious effects on coronary flow. As shown in FIGS. 12–14, the constellation of anti-platelet effect, long duration of action, and increased coronary blood flow, is unmatched by other nitroso-compounds. Thus, S-nitrosoproteins have very unique hemodynamic and bioactive profiles.

Example 8

Demonstration of the Vasodilatory Effect of S-Nitroso-Cathepsin

The effect of S—NO-cathepsin was studied according to the methods described in Example 7a. Results obtained demonstrated that S—NO-cathepsin, at a concentration of 150 nM-1.5 µM, inhibits platelet aggregation.

The effect of S—NO-cathepsin on vasodilation was studied according to the methods described in Example 7b. As shown in the illustrative tracings of FIG. 12, S—NO-cathepsin, at a concentration of 150 nM–1.5 µM induces vessel relaxation which is unmatched by equimolar amounts of non-nitrosylated cathepsin.

Example 9

Demonstration of the Platelet Inhibitory and Vasodilatory Effect of S-Nitroso-Lipoprotein The effect of S—NO-LDL on platelet aggregation was studied according to the methods described in Example 7a. Aggregations were quantified by measuring the extent of change of light transmittance, and expressed as a normalized value relative to control aggregations. As shown the illustrative tracings of FIG. 13, inhibition of platelet aggregation is demonstrable at a concentration of 1 µM S—NO-LDL.

The effect of S—NO-LDL on vasodilation was studied according to the methods described in Example 7b. As shown in FIG. 14, S—NO-LDL induces vessel relaxation which is unmatched by equimolar amounts of non-nitrosylated LDL.

Example 10

Figure 15:
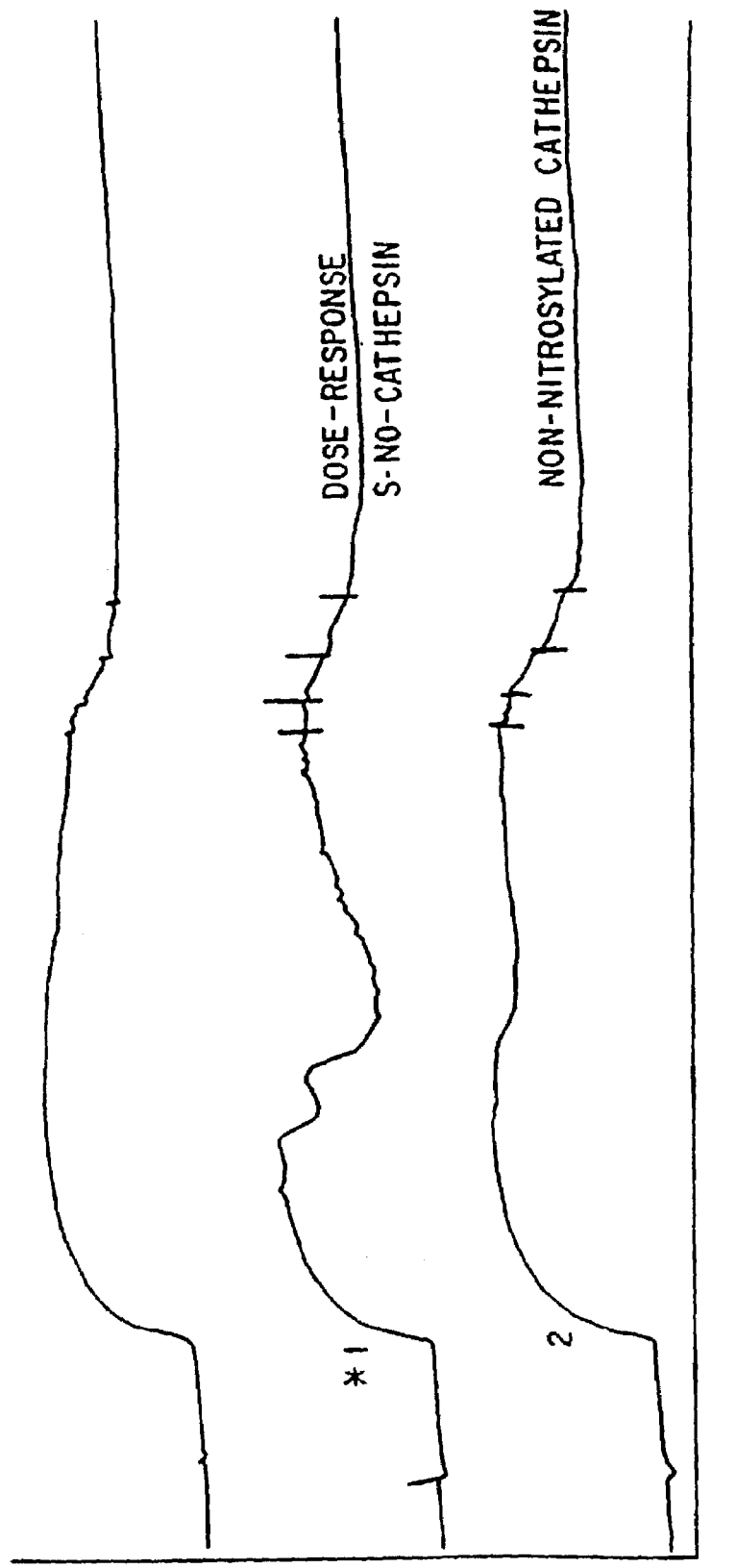
FIG. 15. Dose-dependent vasodilatory response caused by S-nitroso-cathepsin.
Figure 16:
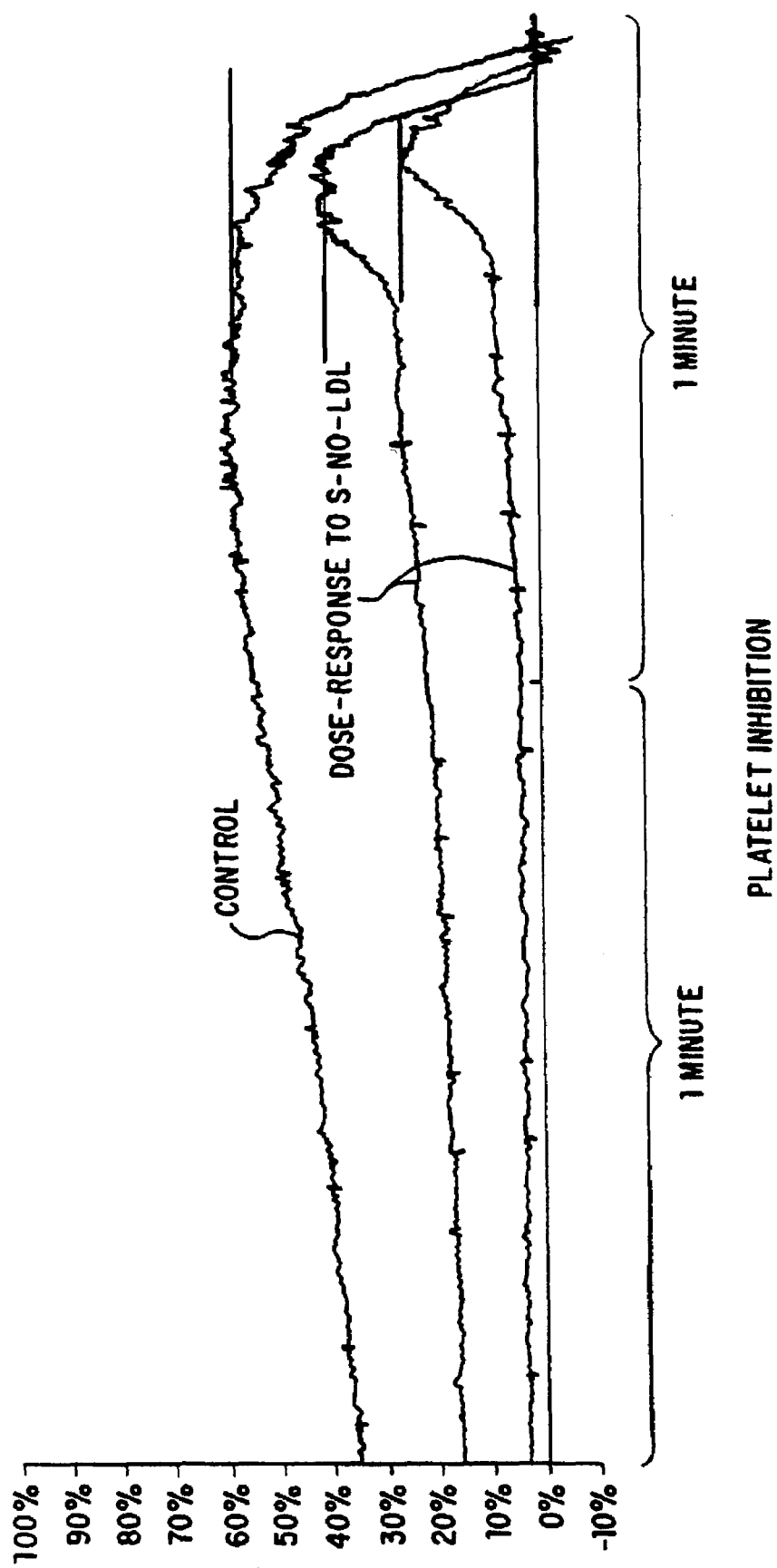
FIG. 16. Tracings of dose-dependent inhibition of platelet aggregation caused by S-nitroso-LDL.

Demonstration of the Platelet Inhibitory and Vasodilatory Effect of S-Nitroso-Immunoglobulin The effect of S—NO-Ig on platelet aggregation was studied according to the methods described in Example 7a. Aggregations were quantified by measuring the extent of change of light transmittance, and expressed as a normalized value relative to control aggregations. As shown in FIG. 15, inhibition of platelet aggregation is demonstrable at concentrations of S—NO-Ig in the pharmacologic range of 150 nM–1.5 µM.

The effect of S—NO-Ig on vasodilation was studied according to the methods described in Example 7b. As shown in FIG. 15, S—NO-Ig, at concentrations in the range of 150 nM–1.5 µM, induces relaxation which is unmatched by equimolar amounts of immunoglobulin alone.

Example 11

Relaxation of Airway Smooth Muscle Caused by S-Nitroso-BSA

1. Materials

Glutathione, L-cysteine, DL-homocysteine, D-penicillin, hemoglobin (bovine), methylene blue and Medium 199 sets were purchased from Sigma Chemical Co., St. Louis, Mo. N-acetylcysteine was obtained from Aldrich Chemical Co., Milwaukee, Wis. Captopril was kindly provided by Dr. Victor Dzau. Sodium nitrite, histamine and methacholine were purchased from Fisher Scientific, Fairlawn, N. J. Leukotriene $D_4$ was purchased from Anaquest, BOC Inc., Madison, Wis. Antibiotic/antimycotic mixture (10,000 U/ml penicillin G sodium, 10,000 mg/ml, streptomycin sulfate, 25 mg/ml amphotericin B) was purchased from Gibco laboratories, Grand Island, N.Y. Radioimmunoassay kits for the determination of cyclic GMP were purchased from New England Nuclear, Boston, Mass.

2. Preparation of Airways

Male Hartley guinea pigs (500–600 g) were anesthetized by inhalation of enflurane to achieve a surgical plane of anesthesia. The trachea were excised and placed in Kreb's-Hanseleit buffer (mM); NaCl 118, KCl 5.4, $NaH_2PO_4$ 1.01, glucose 11.1, $NaHCO_3$ 25.0, $MgSO_4$ 0.69, CaCl 2.32, pH 7.4. The airways were then dissected free from surrounding fat and connective tissue and cut into rings 2–4 mm in diameter. The trachea rings were placed in sterile Medium 199 containing 1% antibiotic/antimycotic mixture in an atmosphere of 5% $CO_2$, 45% $O_2$, 55% $N_2$ and kept for up to 48 hours in tissue culture. The experiments were also performed on human airways isolated by the same method.

3. Bioassay

Trachea rings were mounted on stirrups and connected to transducers (model FTO3C Grass), by which changes in isometric tension were measured. Rings were then suspended in 10 cc of oxygenated (95% $O_2$, 5% $CO_2$) buffer. Airway rings were equilibrated for 60 minutes under a load of 1 gm and then primed twice by exposure to 100 µM methacholine. The rings were contracted with various agonists at concentrations determined to generate 50% (±16% S.D.) of maximum tone, after which the effect of S—NO-BSA was assessed. In selected experiments, relaxation responses were determined in the presence of hemoglobin, or after rings had been preexposed to methylene blue for 30 minutes.

4. Results

Figure 17:
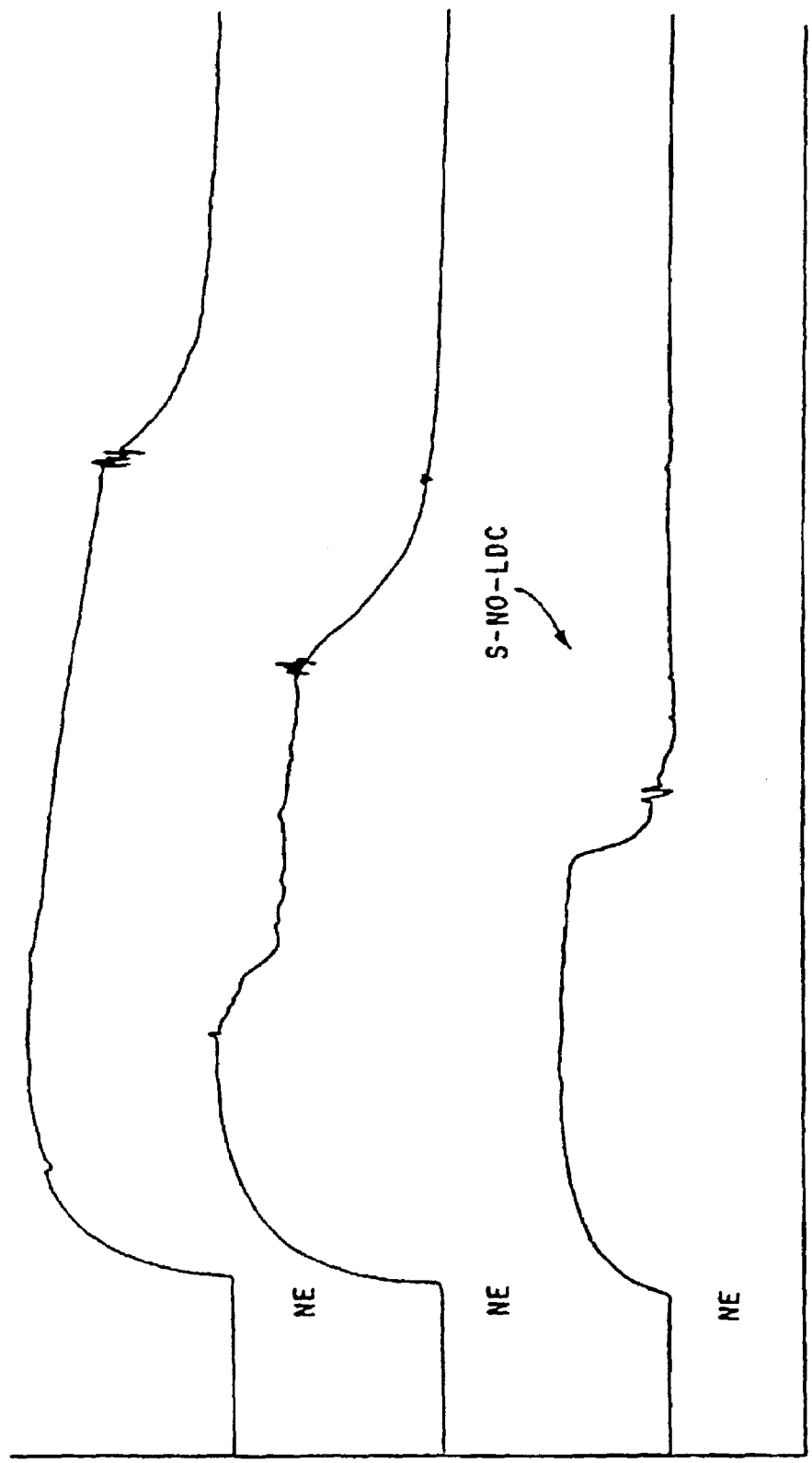
FIG. 17. Representative tracings of vessel relaxation caused by S-nitroso-LDL.
Figure 18:
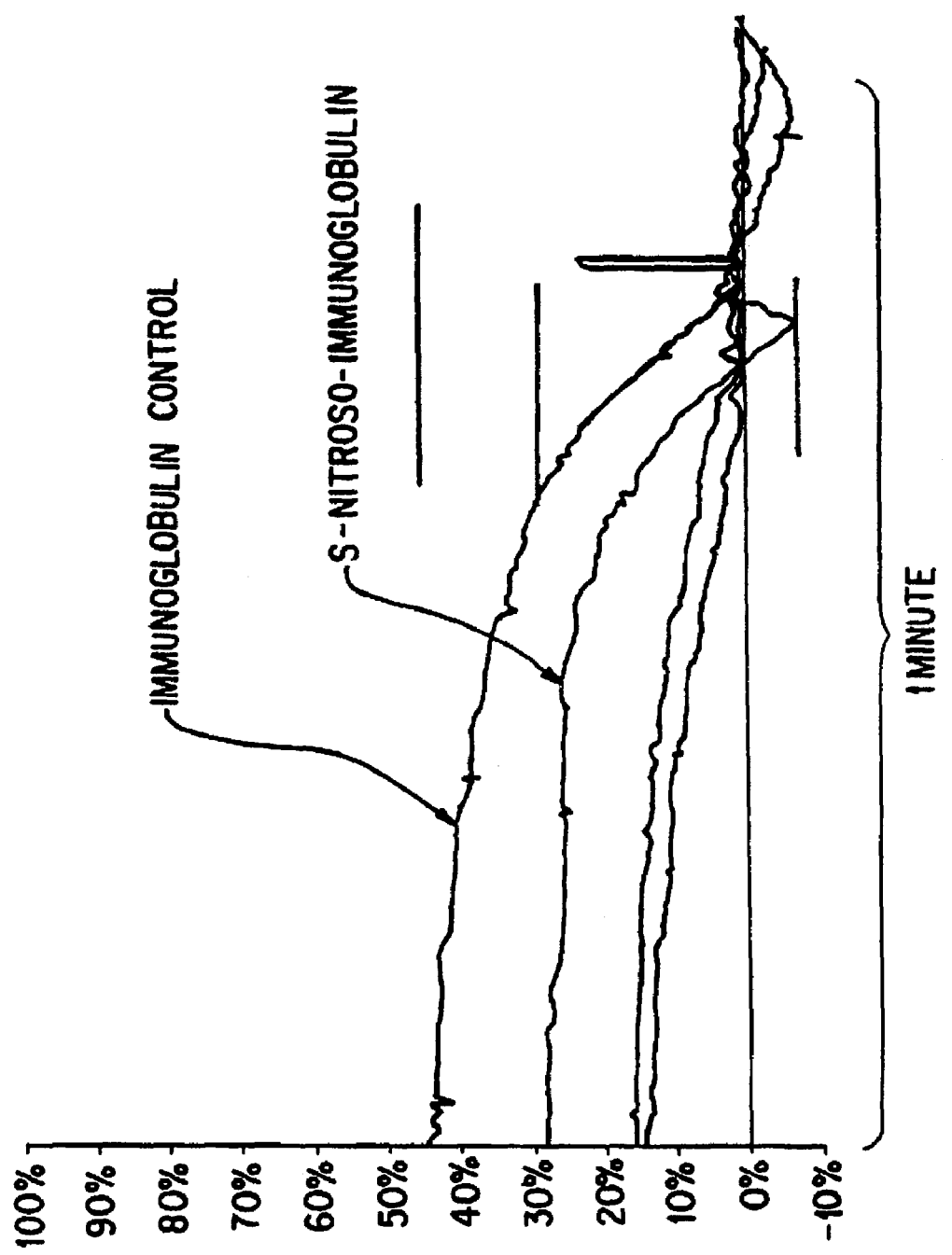
FIG. 18. Tracings of dose-dependent inhibition of platelet aggregation caused by S-nitroso-immunoglobulin.
Figure 19:
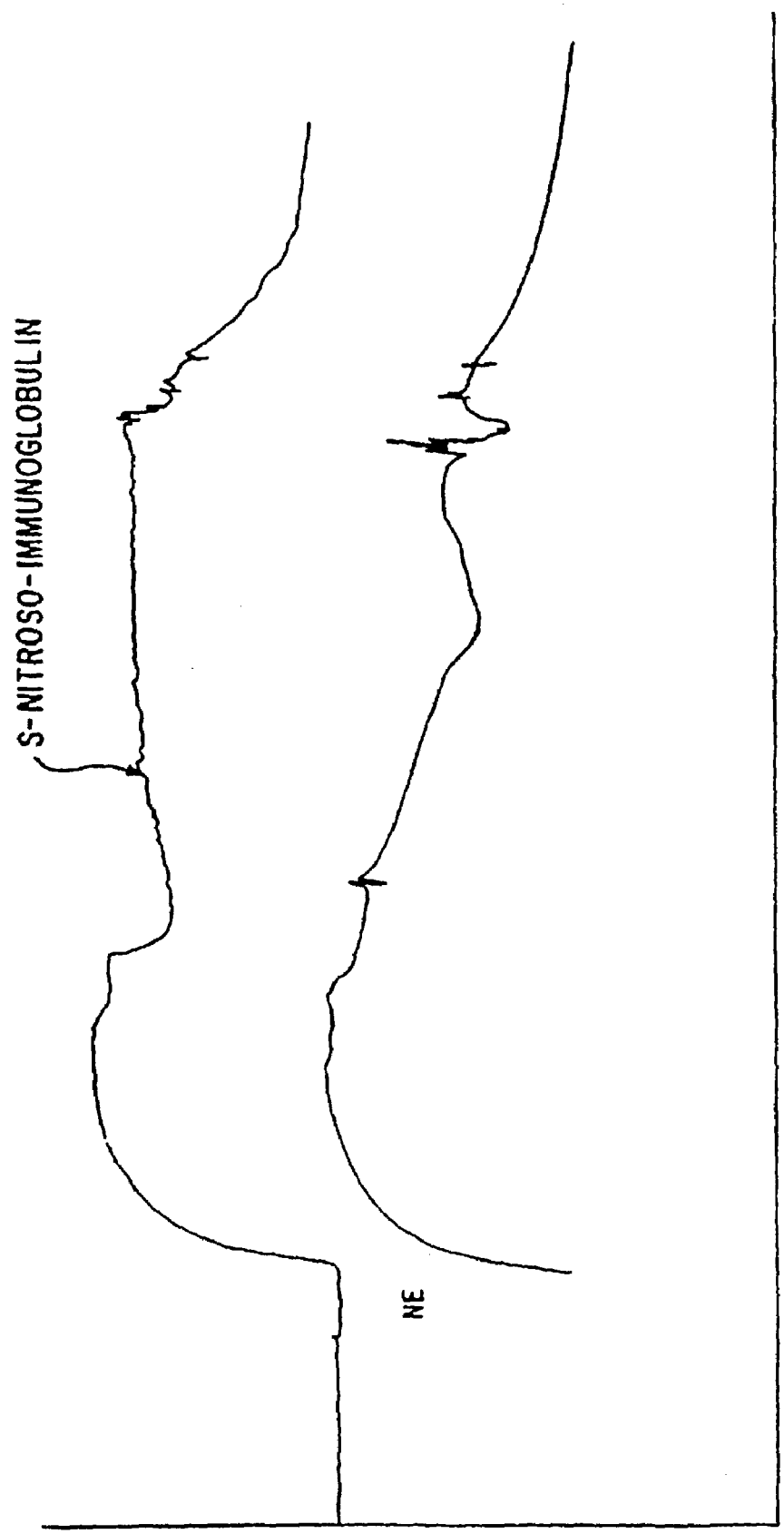
FIG. 19. Representative tracings of vessel relaxation caused by S-nitroso-immunoglobulin.
Figure 20:
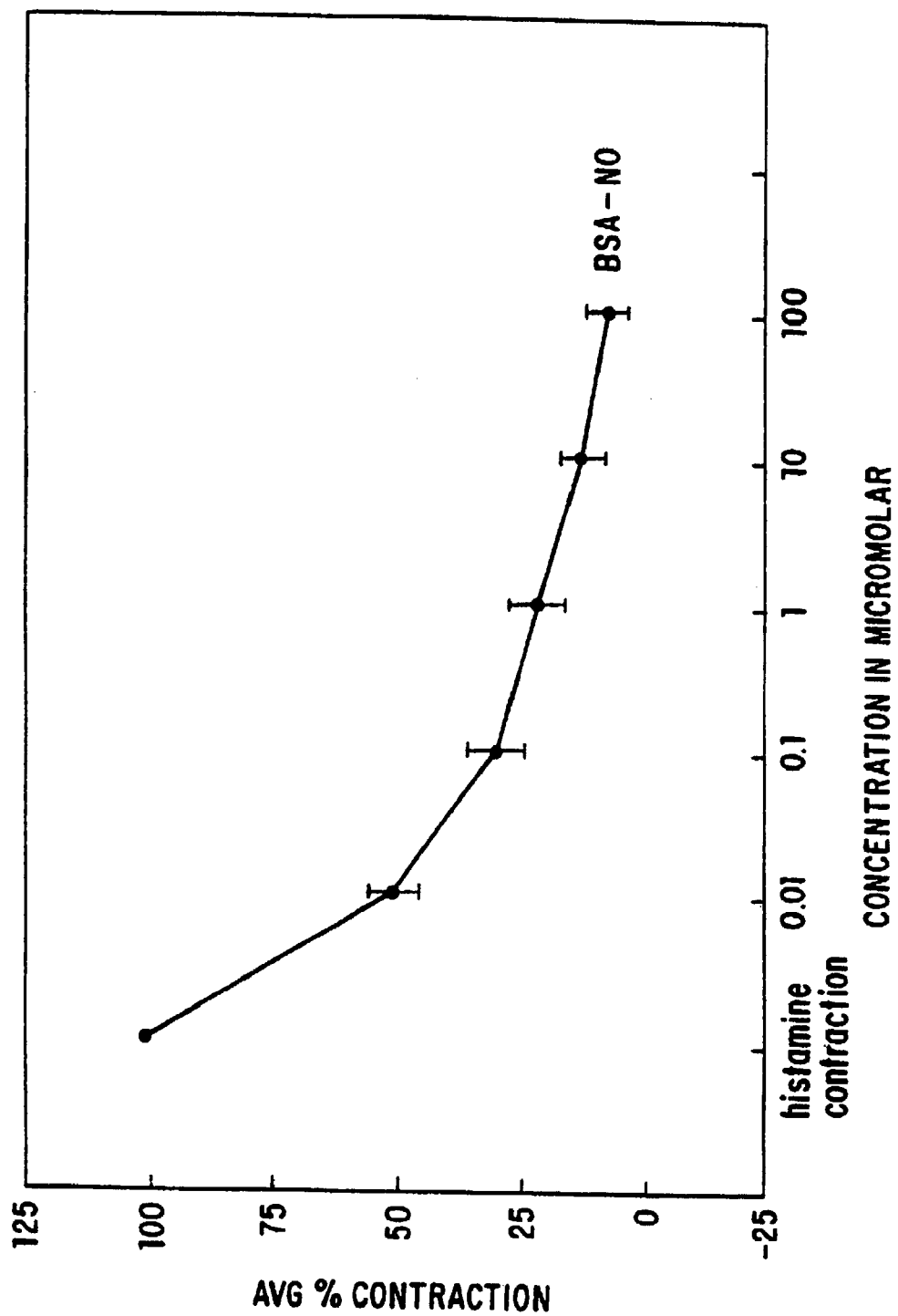
FIG. 20. Concentration-dependent relaxation of airway smooth muscle caused by S—NO-BSA.

As shown in FIG. 17, S—NO-BSA is a potent airway smooth muscle relaxant, producing 50% relaxation at a concentration of 0.01 µM and over 75% relaxation at a concentration of 10 µM.

Example 12

Inhibition of Enzymatic Activity of Cathepsin B by Nitrosylation

The enzymatic activity of S—NO-cathepsin B was measured against the chromogenic substrate, S2251 at pH 5, in sodium acetate buffer. S-nitrosylation resulted in a loss of enzymatic activity.

Example 13

Nitrosylation of Aromatic Amino Acids

1. Methods a. Preparation of Nitroso-Tyrosine 50 mmol of L-tyrosine (Sigma Chemical company; St. Louis, Mo.) were dissolved into 0.5 ml of distilled water. 250 mmol of Na$^{15}$NO$_2$ (sodium N-[$^{15}$]nitrite: MSD Isotopes, Merck Scientific; Rahway, N. J.) were dissolved into 0.5 mL of 1 N HCL (Fisher Scientific; Fair Lawn, N.J.) and transferred immediately to the aqueous tyrosine solution with agitation by Vortex stirrer. Solution was capped and allowed to sit at room temperature for 30 minutes.

NMR measurements were made as follows:

(a) $^{15}$N-NMR: D$_2$O was added and measurements were taken immediately;

(b) $^1$H-NMR: After $^{15}$N-NMR was completed, solution was removed and placed into a small round-bottom flask and water was removed in vacuo. D$_2$O was added to the dry off-white solid (this time as a solvent) and measurements were run immediately;

(c) Infrared Spectroscopy: Fourier Transform Infrared Spectroscopy (FTIR) samples were prepared through removal of water (as in (b)) and subsequent creation of a Nujol Mull using mineral oil.

(d) Ultraviolet and Visible Spectroscopy (UV-Vis): Samples for UV-Vis examination were used as per above prep without further modification. Samples were referenced to distilled water.

b. Nitrosylation of Phenylalanine, Tyrosine, and L-Boc-Tyr (Et)-OH 50 mmol of L-phenylalanine, L-tyrosine (Sigma Chemical Company; St. Louis, Mo.), or L-boc-tyr(Et)-OH (Bachem Bioscientific Incorporated; Philadelphia, Pa.) were dissolved into 0.5 ml of distilled water. 250 mmol of Na$^{15}$NO$_2$ (sodium N-[15]nitrite) were dissolved into 0.5 ml of 1 N HCl (aq.) and transferred immediately to the aqueous amino acid solution with agitation by Vortex stirrer. Solution was capped and allowed to sit at room temperature for 30 minutes. $^{15}$N-NMR and $^1$H-NMR were performed as per nitroso-tyrosine above. Standard reference of tyrosine for FTIR was prepared as a Nujol Mull of pure crystalline L-tyrosine.

c. Nitrosylation of Tryptophan 1.7 mM of tryptophan were reacted with equimolar NaNO$_2$ in 0.5 N HCl for time periods of 5, 10, 15 and 60 minutes at 25° C.

2. Results a. 15N-NMR Data

Figures 21A, 21B:
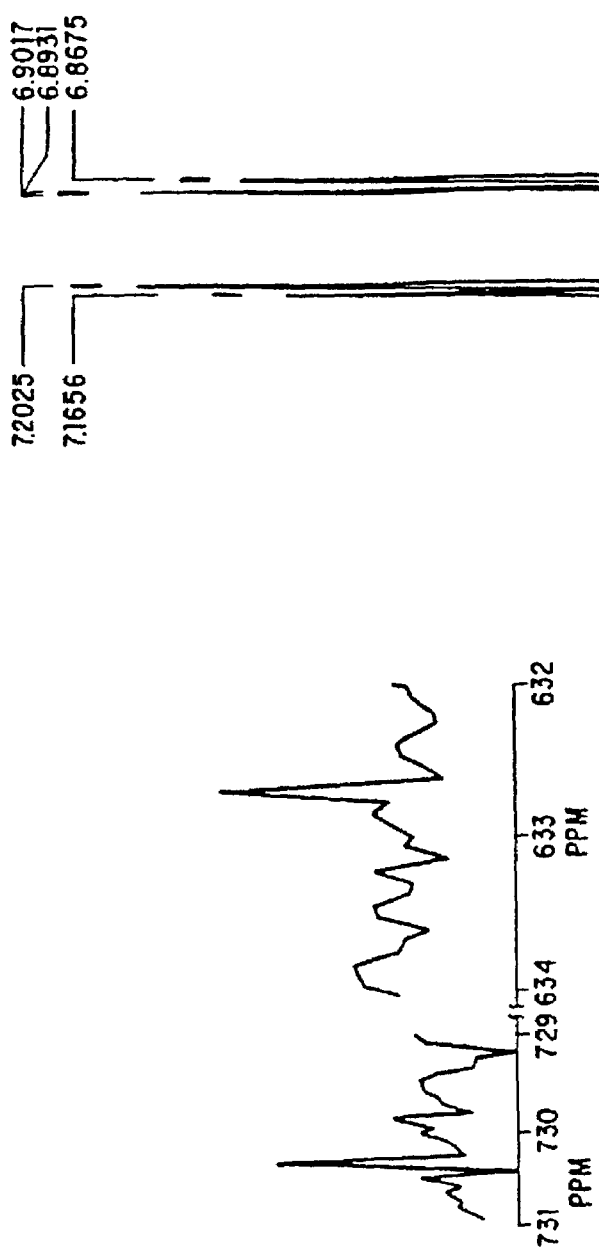
FIG. 21. Nitrosylation of L-tyrosine.

All NMR [$^{15}$N and $^1$H] were run on two Bruker AM500 MgHz spectrometers. Nitrosylation of tyrosine at pH 0.3 gives signals at approximately 730 ppm and 630 ppm relative to saturated sodium N-[15]nitrite aqueous solution referenced at 587 ppm ($^{15}$15 NO$_2$) (FIG. 21a.). A signal at 353 ppm (aqueous NO.sup.12) was also observed. Nitrosylation of phenylalanine under the same conditions gave the signal at approximately 630 ppm but not the 730 ppm signal despite repeated attempts (FIG. 22). Nitrosylation of phenylalanine also yielded signals at 587 ppm (excess, unprotonated nitrite) and 353 ppm. Nitrosylation of O-blocked tyrosine model, boc-tyr(Et)-OH, also yielded a signal at approximately 630 ppm; and others at 587 ppm and 353 ppm. Small signals in the range 450–495 ppm were observed for the tyrosine models, phe and boc-tyr(Et)-OH.

b. 1H-NMR Data

To further characterize the nitrosylation of the phenolic functionality of L-tyr to the exclusion of C-nitrosylation, proton-NMR was performed on nitrosylated tyrosine; modification of L-tyr at the phenolic-OH would not appear in proton-NMR because of proton exchange with the deuterated solvent (D$_2$O). Examination of the spectra showed the classic doublet of doublets at low field, which is characteristic of para-disubstituted benzene, thus excluding aromatic proton substitution (FIG. 21b). This, and other values in the spectra were characteristic of unmodified L-tyr.

c. FTIR Data

Figure 21C:
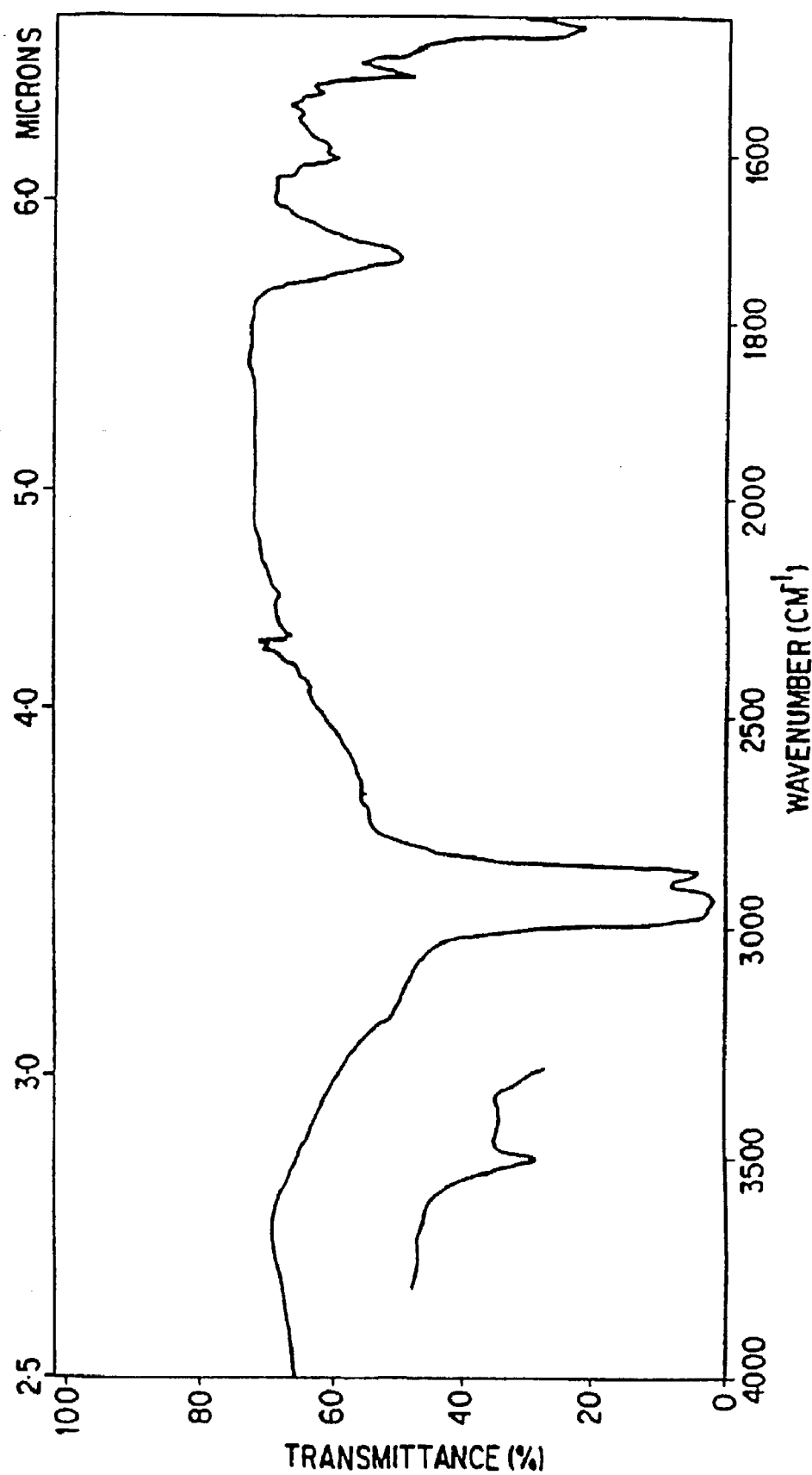
Figure 21D:
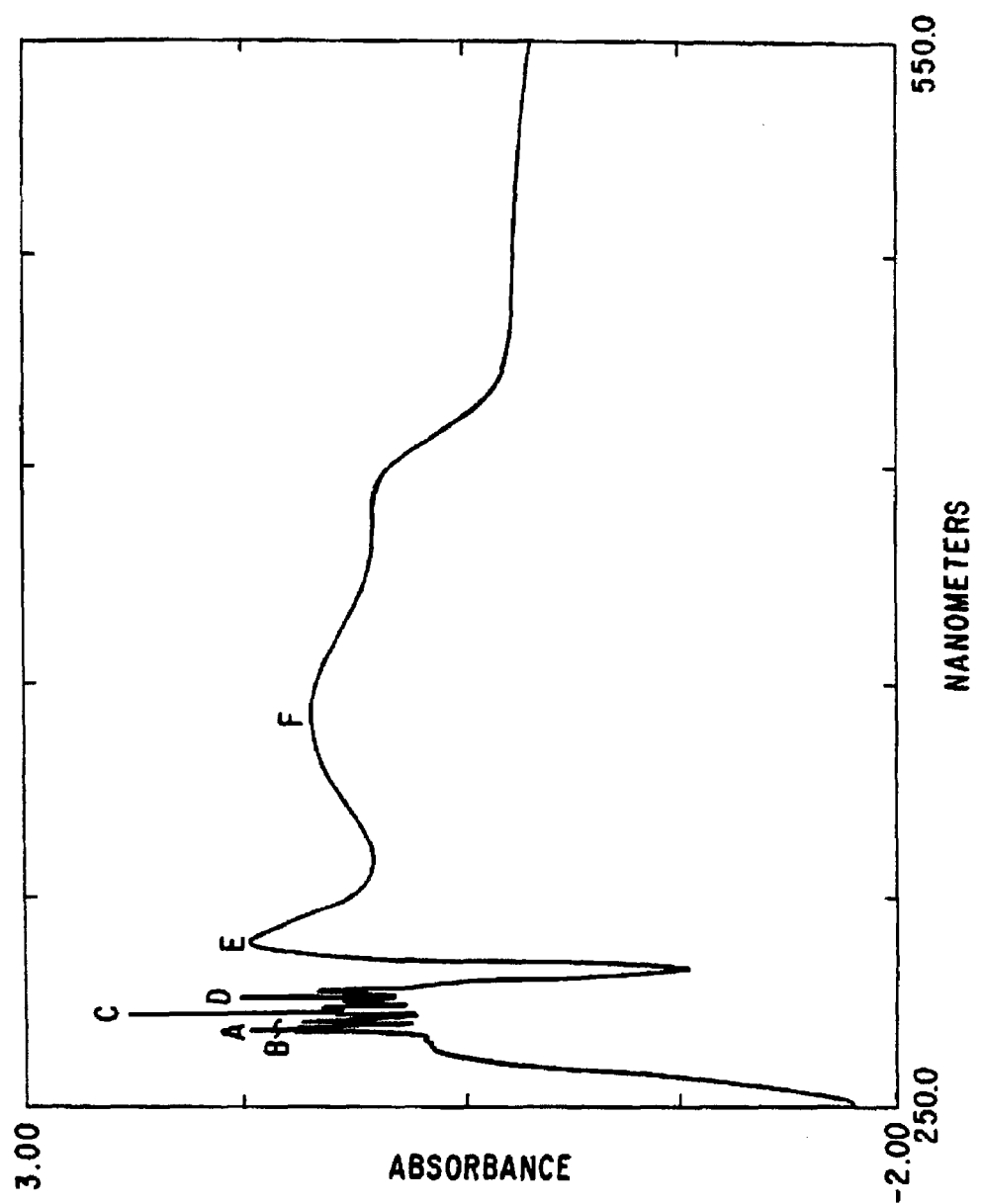

All FTIR were run on a Nicolet 5ZDX FT-IR Spectrometer. FTIR of a Nujol Mull of L-tyrosine showed a very characteristic and well-documented alcoholic stretch in the spectra due to the phenolic-OH (FIG. 1d. inlaid). This spectrum lacked any signal(s) at the 1680–1610 cm$^{-1}$, range that coincides with the O—N=O stretch (not shown). FTIR of nitrosylated L-tyrosine showed no evidence of alcoholic-OH stretches and contained two small bands in the range of 1680–1610 cm$^{-1}$ that could possibly account for the expected O—N=O stretch (Wade, L. G., Organic Chemistry (1st Ed.) Prentice-Hall Inc., Englewood Cliffs, N.J.: 1987. p. 1334) (FIG. 21c.).

d. UV-Vis Data

All UV-Vis spectroscopy was performed using a Gilford Response UV-Vis Spectrophotometer (CIBA-Corning, Oberlin, Ohio). Treatment of L-tyrosine with aqueous sodium nitrite at pH 0.3 (0.5N HCl) resulted in a yellow solution with an absorption maximum at 361 nm. This result is similar to, but differs from previously reported results with nitrosated L-tyrosine. Ortho-ring substituted L-nitro-tyrosine (Sigma) absorbs at 356 nm at pH 0.3.

Treatment of phenylalanine with sodium nitrite at pH 0.3 gives a rapidly changing UV spectrum with a peak increasing in wavelength from 318 nm at 5 min. to a maximum unchanging peak at 527 nm by 30 min.

FIG. 23(a–e) demonstrates time-dependent nitrosylation of tryptophan. The data is suggestive of nitrosylation of both the aromatic ring and amino groups.

Example 14

Nitrosylation of BSA

BSA, at 200 mg/ml, was loaded at a ratio of 20:1 with NO in 0.5 N HCl for 30 minutes at room temperature. As shown in FIG. 24, the 726 ppm peak indicates O-nitrosation of the tyrosine residues on BSA. FIG. 24 also provides evidence for the nitrosation of several other functional groups on BSA. The data are also suggestive of ring nitrosation and amine nitrosation (600 ppm peak) as well.

Time-dependent NO loading of BSA was performed by exposing BSA (200 mg/ml) in phosphate-buffer (10 mM, pH 7.4) to NO gas-bubbled into the BSA solution, for 1, 5 and 30 minute time periods. FIG. 25 provides UV spectrum data which indicates NO loading of BSA.

Example 15

Nitrosylation of t-PA; NO Loading t-PA at 10 mg/ml was exposed 10:1 to excess $NaNO_2$ in 0.5 N HCl. FIG. 26 shows NO-loading of t-PA.

Example 16

Vasodilatory Effect of NO-Loaded BSA

BSA was loaded with NO according to the method described in Example 14. Vasodilatory effect was studied in a rabbit aorta bioassay, according to the methods described in Example 6C. As shown in FIG. 27, increasing concentrations of NO resulted in an increase in vessel relaxation induced by the resultant NO-BSA.

Example 17

Guanylate Cyclase Inhibitors Do Not Inhibit S-nitroso-protein-Induced Relaxation in Human Airways The effect of guanylate cyclase inhibitors upon S-nitroso-protein-induced airway relaxation and cGMP increase was assessed, using the previously described bioassay and cyclic nucleotide assay procedures. The bronchodilatory effect of S-nitroso-albumin was examined in human airways (5–12 mm outer diameter). Concentration-response relationships for rings contracted with methacholine (7 μM) resulted in IC50 values of 22 μM, approximately two orders of magnitude greater than theophylline.

S-nitroso-albumin (100 μM) induced increases over control airway cGMP levels. However, S-nitroso-albumin-induced airway relaxation was not significantly inhibited by methylene blue ($10^{-4}$) or LY83583 ($5 \times 10^{-5}$). Similarly, hemoglobin (100 μM) had little effect on S-nitroso-albumin-induced relaxation (P=NS).

These results demonstrate that the mechanism by which S-nitroso-protein cause airway relaxation is not due solely to increases in cGMP. Thus, S-nitroso-proteins cause airway relaxation through both an increase in cyclic GMP, as well as a cGMP-independent pathway. In doing so, they provide a means for achieving combination therapy by maximizing the synergistic effect of two separate mechanisms.

Example 18

S-Nitroso-Proteins Resist Decomposition in the Presence of Redox Metals

The stability of S-nitroso-albumin in the presence of oxygen and redox metals was assessed. When subjected to conditions consisting of 95% $O_2$, pH 7.4, the half life of this compound was shown to be on the order of hours, and significantly greater than that of NO, or NO., which, under similar conditions, are on the order of seconds.

In addition, S-nitroso-protein stability was assessed in the presence of various redox metals or chelating agents. S-nitroso-albumin was resistant to decomposition when $Cu^+$, $Fe^{2+}$, or $Cu^{2+}$ (50 μM) or defuroxamine or EDTA (10 μM) were added. Thus, these experiments demonstrate that, unlike NO., S-nitroso-proteins are not rapidly inactivated in the presence of oxygen, nor do they decompose in the presence of redox metals.

Example 19

S-Nitrosylation of Hemoglobin Increases Hemoglobin-Oxygen Binding

Additional experiments were conducted to evaluate the reaction between S-nitrosothiols and hemoglobin. S-nitrosylation of hemoglobin was accomplished by reacting 12.5 μM hemoglobin with 12.5 μM S-nitroso-N-acetylcysteine (also known as SNOAC) for 5 and 20 minute intervals (pH 6.9). S-nitrosylation was verified, using standard methods for detection of S-nitrosothiols (Saville, Analyst 83:670–672 (1958)). The Saville method, which assays free $NO_x$ in solution, involves a diazotization reaction with sulfanilamide and subsequent coupling with the chromophore N-(1-naphthyl)ethylenediamine. The specificity for S-nitrosothiols derives from assay determinations performed in the presence and absence of $HgCl_2$, the latter reagent catalyzing the hydrolysis of the S—NO bond. Confirmatory evidence for S-nitrosothiol bond formation was obtained by spectrophotometry, demonstrated by the absorption maximum of 540 nm, as shown in FIG. 28. This was demonstrated using $NO^+$ equivalents in the form of SNOAC.

As demonstrated by FIG. 29, the UV spectrum of hemoglobin incubated with SNOAC shows no reaction at the redox metal (iron-binding site) of hemoglobin, over 15 minutes. For the purposes of comparison, equimolar concentrations of hemoglobin and $NaNO_2$ were reacted in 0.5 N HCl, to form nitrosyl-hemoglobin, and the UV spectrum was obtained. As shown in FIG. 30, NO reacted instantaneously with the redox metal site on hemoglobin. The fact that the S-nitrosothiol did not react with the redox metal site of hemoglobin, but with its thiol group instead, indicates that the reactive NO species donated by the S-nitrosothiol is nitrosonium or nitroxyl.

S-nitrosylation of hemoglobin does not result in the formation of methemoglobin and consequent impairment in hemoglobin-oxygen binding. Furthermore, an additional experiment demonstrated that S-nitrosylation of hemoglobin causes a leftward shift in the hemoglobin-oxygen association curve, indicating an increase in oxygen binding. Thus, the reaction between S-nitrosothiols and hemoglobin not only eliminates the inhibition of oxygen binding which occurs from the reaction with uncharged NO and generation of methemoglobin, but it actually increases oxygen binding.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of modulating the delivery of carbon monoxide or nitric oxide bound to hemoglobin to a bodily tissue in a patient in need thereof comprising administering to the patient a therapeutically effective amount of a pharmaceutical composition comprising a nitrosated and/or nitrosylated heme protein, wherein the heme protein is nitrosated and/or nitrosylated at one or more thiol groups in the heme protein.

2. The method of claim 1, wherein the pharmaceutical composition further comprises at least one of a nonionic surfactant, a phospholipid, an emulsifier, and a fatty acid.

3. The method of claim 1, wherein the heme protein is hemoglobin.

4. The method of claim 3, wherein the hemoglobin is a human hemoglobin.

5. The method of claim 3, wherein the hemoglobin is bovine hemoglobin.

* * * * *